United States Patent
Bregman et al.

(10) Patent No.: US 9,334,269 B2
(45) Date of Patent: May 10, 2016

(54) CARBOXAMIDES AS INHIBITORS OF VOLTAGE-GATED SODIUM CHANNELS

(75) Inventors: Howard Bregman, Melrose, MA (US); John L. Buchanan, Newton, MA (US); Nagasree Chakka, Lexington, MA (US); Erin F. Dimauro, Cambridge, MA (US); Bingfan Du, Cambridge, MA (US); Hanh Nho Nguyen, Arlington, MA (US); Xiao Mei Zheng, Natick, MA (US)

(73) Assignee: AMGEN INC., Thousand Oaks, CA (US)

( * ) Notice: Subject to any disclaimer, the term of this patent is extended or adjusted under 35 U.S.C. 154(b) by 51 days.

(21) Appl. No.: 13/575,912

(22) PCT Filed: Feb. 16, 2011

(86) PCT No.: PCT/US2011/025092
§ 371 (c)(1),
(2), (4) Date: Jul. 27, 2012

(87) PCT Pub. No.: WO2011/103196
PCT Pub. Date: Aug. 25, 2011

(65) Prior Publication Data
US 2013/0131035 A1 May 23, 2013

Related U.S. Application Data

(60) Provisional application No. 61/305,235, filed on Feb. 17, 2010.

(51) Int. Cl.
| | |
|---|---|
| *C07D 471/10* | (2006.01) |
| *C07D 401/04* | (2006.01) |
| *C07D 403/04* | (2006.01) |
| *C07D 251/48* | (2006.01) |
| *C07D 213/74* | (2006.01) |
| *C07D 239/48* | (2006.01) |

(52) U.S. Cl.
CPC ............ *C07D 471/10* (2013.01); *C07D 213/74* (2013.01); *C07D 239/48* (2013.01); *C07D 251/48* (2013.01); *C07D 401/04* (2013.01); *C07D 403/04* (2013.01)

(58) Field of Classification Search
USPC ............... 514/210.2, 245, 275; 544/209, 323; 546/268.1
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 7,173,028 B2 | 2/2007 | Dahmann et al. | |
| 2009/0298823 A1* | 12/2009 | Song .................... | C07D 239/48 514/234.2 |

FOREIGN PATENT DOCUMENTS

| | | |
|---|---|---|
| WO | 02083653 A1 | 10/2002 |
| WO | 2005012294 A1 | 2/2005 |
| WO | 2006050476 A2 | 5/2006 |
| WO | 2008076779 A2 | 6/2008 |
| WO | 2008104754 A1 | 9/2008 |
| WO | 2009131687 A2 | 10/2009 |
| WO | 2010022055 A2 | 2/2010 |
| WO | 2010065721 A1 | 6/2010 |
| WO | WO 2010/144338 | * 12/2010 |

OTHER PUBLICATIONS

Wang (Are Voltage-gated sodium channels on the dorsal root ganglion involved in the development of neuropathic pain?, Molecular Pain, Jul. 2011, pp. 1-9).*
Goldin, A. L, "Resurgence of sodium channel research," *Ann Rev Physiol* 63:871-894, 2001.
Wood, J. N. and, Boorman, J. "Voltage-gated sodium channel blockers; target validation and therapeutic potential," *Curr. Top Med. Chem.* 5:529-537, 2005.
Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006.
Yang Y., Wang Y., Li S, et al., "Mutations in SCN9A, encoding a sodium channel alpha subunit, in patients with primary erythermalgia," J. Med. Genet. 41:171-174, 2004.
Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338.
An SCN9A channelopathy causes congenital inability to experience pain, *Nature* 444:894-898, 2006.
Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007.
Morinville et al., *J Comp Neurol.*, 504:680-689 (2007).
Ettinger and Argoff, *Neurotherapeutics*, 4:75-83 (2007).
Waxman, *Nature Neurosci.* 7 :932-941 (2006).
Do and Bean, *Neuron* 39 :109-120 (2003).
Puopolo et al., *J. Neurosci.* 27 :645-656 (2007).
Hamann M., et. al., *Exp. Neurol.* 184(2):830-838, 2003.
McKinney B. C, et. al., *Genes Brain Behav.* 7(6):629-638, 2008.
Woodruff-Pak D. S., et. al., *Behav. Neurosci.* 120(2):229-240, 2006.
Haufe V., et. al., *J Mol. Cell Cardiol.* 42(3):469-477, 2007.
Johannessen L. C., *CNS Drugs* 22(1)27-47, 2008.
Kim D. Y., et. al., *Nat. Cell. Biol.* 9(7):755-764, 2007.
Gillet L., et. al.,*J Biol Chem* 2009, Jan. 28 (epub).

\* cited by examiner

*Primary Examiner* — Kathrien Cruz
(74) *Attorney, Agent, or Firm* — Elsa D. Lemoine

(57) ABSTRACT

The present invention provides compounds that are inhibitors of voltage-gated sodium channels (Nav), in particular Nav 1.7, and are therefore useful for the treatment of diseases treatable by inhibition of these channels, in particular, chronic pain disorders. Also provided are pharmaceutical compositions containing such compounds and processes for preparing such compounds.

6 Claims, No Drawings

CARBOXAMIDES AS INHIBITORS OF VOLTAGE-GATED SODIUM CHANNELS

CROSS-REFERENCES TO RELATED APPLICATIONS

This application is a 35 U.S.C. §371 national application from PCT/US2011/025092, filed Feb. 16, 2011, which claims the benefit of U.S. Provisional Application No. 61/305,235, filed Feb. 17, 2010.

FIELD OF THE INVENTION

The present invention provides compounds that are inhibitors of voltage-gated sodium channels (Nav), in particular Nav 1.7, and are therefore useful for the treatment of diseases treatable by inhibition of these channels, in particular, chronic pain disorders. Also provided are pharmaceutical compositions containing such compounds and processes for preparing such compounds.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3rd Ed. 2001). There are nine different isoforms of voltage-gated sodium channel (Nav1.1-Nav1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential," *Curr. Top Med. Chem.* 5:529-537, 2005). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav1.7 (SCN9A) is required to sense pain. Rare genetic forms of severe chronic pain, Primary Erythromelalgia and Paroxysmal Extreme Pain Disorder, result from mutations that increase the activity of Nav1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," *J. Med. Genet.* 41:171-174, 2004; Drenth J. P. H., to Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav1.7 via mutations that truncate the protein and destroy function (Cox J. J., Reimann F, Nicholas A. K., et al. "An SCN9A channel-opathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav1.7 governs one or more control points critical for pain perception. Accordingly, a therapeutic agent that inhibits Nav1.7 should effectively treat chronic pain in humans. The present invention fulfils this and related needs.

SUMMARY OF THE INVENTION

In one aspect, provided herein are compounds of Formula (I):

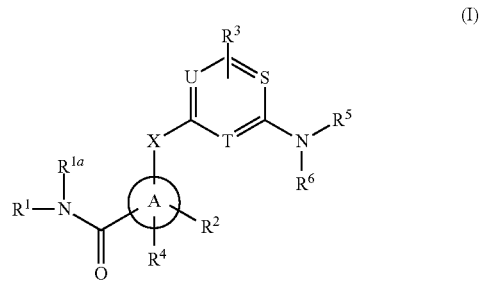

where:
X is —NH—, —NMe-, —O— or —S—;
S, T and U are independently —CH— or —N-provided at least one of S, T and U is —N—;
A is aryl or heteroaryl;
$R^1$ is hydrogen, alkyl, haloalkyl, substituted alkyl, acyloxyalkyl, cycloalkyl, heterocyclyl, aryl, heteroaryl, cycloalkylalkyl, heterocyclylalkyl, aralkyl, or heteroaralkyl wherein the ring in cycloalkyl, heterocyclyl, aryl, heteroaryl, cycloalkylalkyl, heterocyclylalkyl, aralkyl, or heteroaralkyl is optionally substituted with one to three substitutents independently selected from alkyl, halo, haloalkyl, alkoxy, hydroxyl, or haloalkoxy;
$R^{1a}$ is hydrogen or alkyl;
$R^2$ is hydrogen, alkyl, substituted alkyl, aryl, heteroaryl, cycloalkyl, halo, haloalkyl, haloalkoxy, alkoxy, alkoxyalkoxy, hydroxyl, carboxy, alkoxycarbonyl, cyano, amino, monosubstituted or disubstitued amino, sulfonyl, or alkoxyalkyl;
$R^3$ is hydrogen, halo, alkyl, alkoxy, cyano, or haloalkyl;
$R^4$ is hydrogen, alkyl, substituted alkyl, halo, alkoxy, hydroxy, carboxy, —CONH$_2$, —CONMe$_2$, cycloalkyl, or dialkylamino;
$R^5$ is hydrogen, alkyl, substituted alkyl, aryl, or heteroaryl;
$R^6$ is aryl, heteroaryl, heteroaralkyl, heterocyclyl, heterocyclylalkyl, cycloalkyl, or aralkyl wherein one or two carbon atoms in the alkyl chain in aralkyl are optionally replaced by —N—, —O—, or —CO— provided that —N—, —O—, or —CO— are not on adjacent atoms; or R⁵ and R⁶ together with the nitrogen atom to which they are attached form ring B having the formula:

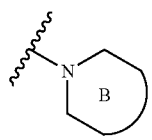

wherein ring B is a heteroaryl, heterocyclyl, bridged heterocyclyl, or spiroheterocyclyl ring, and wherein each aforementioned ring in R⁵, R⁶ and ring B is substituted with $R^a$, $R^b$ or $R^c$ where $R^a$ is hydrogen, alkyl, halo, haloalkyl, haloalkoxy, alkylthio, haloalkylthio, cyano, hydroxy, alkoxy, amino, monosubstituted amino, disubstituted amino, sulfonyl, thio, acyl, carboxy, alkoxycarbonyl, hydroxyalkyl, alkoxyalkyl, aminoalkyl, hydroxyalkoxy, hydroxyalkoxyalkyl, alkoxyalkoxy, aminoalkoxy, aminosulfonyl, aminocarbonyl, or acylamino and $R^b$ and $R^c$ are independently selected from hydrogen, alkyl, substituted alkyl, substituted alkynyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, sulfonylamino, aryl, heteroaryl, cycloalkyl, cycloalkenyl, heterocyclyl, aralkyl, heteroaralkyl, heterocyclylalkyl, aryloxy, heteroaryloxy, cycloalkoxy, aryloxyalkyl, aralkyloxy, aralkyloxyalkyl, aralkylthio, heteroaralkyloxy, heterocyclylalkyloxy, cycloalkylalkyloxy or cycloalkylalkyloxyalkyl where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, cyanoalkyl, alkylthio, cyano, hydroxy, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, cycloalkyl, cycloalkenyl, phenyl, phenxoy, heteroaryl, heterocyclyl, heterocyclylalkyl, aralkyl, aralkyloxy or heteroaralkyl and where the aromatic or alicyclic ring in $R^d$, $R^e$ or $R^f$ is optionally substituted with one to three substituents independently selected from alkyl, halo, haloalkyl, haloalkyloxy, hydroxyl, alkoxy, acetylamino, alkylsulfonyl, or cyano; or a pharmaceutically acceptable salt thereof; provided that when U, S and T are each —N—, then A is phenyl and R³ is hydrogen; and further provided that the compound is not 3-((4-((3S)-3-benzyl-1-piperidinyl)-1,3,5-triazin-2-yl)amino)-N-methylbenzamide; 3-((4-((3R)-3-benzyl-1-piperidinyl)-1,3,5-triazin-2-yl)amino)-N-methylbenzamide; or N-methyl-3-((4-(4-(4-morpholinylcarbonyl)-1-piperidinyl)-1,3,5-triazin-2-yl)amino)benzamide.

In another aspect, provided herein are compounds of Formula (I):

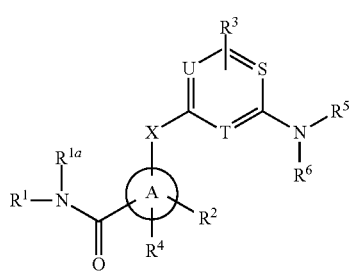

(I)

where:
X is —NH—, —NMe-, —O— or —S—;
S, T and U are independently —CR³— or —N—;
A is aryl or heteroaryl;
R¹ is hydrogen, alkyl, haloalkyl, substituted alkyl, acyloxyalkyl, cycloalkyl, heterocyclyl, aryl, heteroaryl, cycloalkylalkyl, heterocyclylalkyl, aralkyl, or heteroaralkyl wherein the ring in cycloalkyl, heterocyclyl, aryl, heteroaryl, cycloalkylalkyl, heterocyclylalkyl, aralkyl, or heteroaralkyl is optionally substituted with one to three substituents independently selected from alkyl, halo, haloalkyl, alkoxy, hydroxyl, or haloalkoxy;
$R^{1a}$ is hydrogen or alkyl;
R² is hydrogen, alkyl, substituted alkyl, aryl, heteroaryl, cycloalkyl, halo, haloalkyl, haloalkoxy, alkoxy, alkoxyalkoxy, hydroxyl, carboxy, alkoxycarbonyl, cyano, amino, monosubstituted or disubstitued amino, sulfonyl, or alkoxyalkyl;
each R³ is independently hydrogen, halo, alkyl, alkoxy, cyano, or haloalkyl;
R⁴ is hydrogen, alkyl, substituted alkyl, halo, alkoxy, hydroxy, carboxy, —CONH₂, —CONMe₂, cycloalkyl, or dialkylamino;
R⁵ is hydrogen, alkyl, substituted alkyl, aryl, or heteroaryl;
R⁶ is aryl, heteroaryl, heteroaralkyl, heterocyclyl, heterocyclylalkyl, cycloalkyl, or aralkyl wherein one or two carbon atoms in the alkyl chain in aralkyl are optionally replaced by —N—, —O—, or —CO— provided that —N—, —O—, or —CO— are not on adjacent atoms; or
R⁵ and R⁶ together with the nitrogen atom to which they are attached form ring B having the formula:

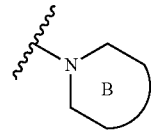

wherein ring B is a heteroaryl, heterocyclyl, bridged heterocyclyl, or spiroheterocyclyl ring, and wherein each aforementioned ring in R⁵, R⁶ and ring B is substituted with $R^a$, $R^b$ or $R^c$ where $R^a$ is hydrogen, alkyl, halo, haloalkyl, haloalkoxy, alkylthio, haloalkylthio, cyano, hydroxy, alkoxy, amino, monosubstituted amino, disubstituted amino, sulfonyl, thio, acyl, carboxy, alkoxycarbonyl, hydroxyalkyl, alkoxyalkyl, aminoalkyl, hydroxyalkoxy, hydroxyalkoxyalkyl, alkoxyalkoxy, aminoalkoxy, aminosulfonyl, aminocarbonyl, or acylamino and $R^b$ and $R^c$ are independently selected from hydrogen, alkyl, substituted alkyl, substituted alkynyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, sulfonylamino, aryl, heteroaryl, cycloalkyl, cycloalkenyl, heterocyclyl, aralkyl, heteroaralkyl, heterocyclylalkyl, aryloxy, heteroaryloxy, cycloalkoxy, aryloxyalkyl, aralkyloxy, aralkyloxyalkyl, aralkylthio, heteroaralkyloxy, heterocyclylalkyloxy, cycloalkylalkyloxy or cycloalkylalkyloxyalkyl where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, cyanoalkyl, alkylthio, cyano, hydroxy, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, cycloalkyl, cycloalkenyl, phenyl, phenxoy, heteroaryl, heterocyclyl, heterocyclylalkyl, aralkyl, aralkyloxy or heteroaralkyl and where the aromatic or alicyclic ring in $R^d$, $R^e$ or $R^f$ is optionally substituted with one to three substituents independently selected from alkyl, halo, haloalkyl, haloalkyloxy, hydroxyl, alkoxy, acetylamino, alkylsulfonyl, or cyano; or a pharmaceutically acceptable salt thereof; provided that when U, S and T are each —N—, then A is phenyl and $R^3$ is hydrogen; and further provided that the compound is not 3-((4-((3S)-3-benzyl-1-piperidinyl)-1,3,5-triazin-2-yl)amino)-N-methyl-benzamide; 3-((4-((3R)-3-benzyl-1-piperidinyl)-1,3,5-triazin-2-yl)amino)-N-methylbenzamide; or N-methyl-3-((4-(4-(4-morpholinylcarbonyl)-1-piperidinyl)-1,3,5-triazin-2-yl)amino)benzamide.

In a particular aspect of the compounds of Formula (I), S, T and U are independently —CH— or —N—; provided at least one of S, T and U is —N—

In a particular aspect of the compounds of Formula (I), X is —NH—.

In another particular aspect of the compounds of Formula (I), S, T and U are —N—.

In another particular aspect of the compounds of Formula (I), S and T are —N— and U is —CH—.

In another particular aspect of the compounds of Formula (I), T and U are —N— and S is —CH—.

In another particular aspect of the compounds of Formula (I), T is —N— and S and U are —CH—.

In any of the above-mentioned aspects, $R^1$ can be alkyl.

In any of the above-mentioned aspects, $R^1$ can be haloalkyl.

In any of the above-mentioned aspects, $R^1$ can be cycloalkyl.

In any of the above-mentioned aspects, $R^1$ can be alkyl substituted with alkoxy.

In any of the above-mentioned aspects, A can be phenyl, $R^4$ can be hydrogen or halo, and $R^2$ can be hydrogen, alkyl, hydroxy, alkoxy, halo, haloalkyl, or dialkylamino.

In any of the above-mentioned aspects, A can be phenyl, $R^4$ can be hydrogen, and $R^2$ can be alkyl, halo, haloalkyl, haloalkoxy, alkoxy or hydroxyl and the $R^2$ group can be ortho to the $R^1R^{1a}NCO$— and para to the X group and the $R^1R^{1a}NCO$— group can be meta to the X group.

In another particular aspect of the compounds of Formula (I), —$NR^5R^6$ is

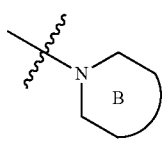

wherein ring B is piperidin-1-yl, piperazin-1-yl, or 3,6-dihydro-1(2H)-pyridinyl, each ring substituted at the 4-position with $R^b$ where $R^b$ is phenyl or heteroaryl, each ring optionally substituted with $R^d$ or $R^e$.

In another particular aspect of the compounds of Formula (I), —$NR^5R^6$ is

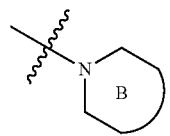

wherein ring B is azetidinyl or piperidin-1-yl or wherein azetidin-1-yl is substituted at the 3-position of the ring and piperidin-1-yl is substituted at the 4-position of piperidin-1-yl ring, with $R^b$ where $R^b$ is aryloxy, aralkyloxy or aryloxyalkyl optionally substituted with $R^d$, $R^e$, or $R^f$.

In another particular aspect of the compounds of Formula (I), $R^{1a}$ and $R^3$ can be hydrogen.

In another particular aspect of the compounds of Formula (I), the compound is:
3-((4-(3-(4-chlorophenoxy)-1-azetidinyl)-1,3,5-triazin-2-yl)amino)-N-methyl-benzamide;
2-fluoro-N-methyl-5-((4-(4-(4-phenyl-1,3-thiazol-2-yl)-1-piperidinyl)-1,3,5-triazin-2-yl)amino)benzamide;
5-((4-(3-(4-chlorophenoxy)-1-azetidinyl)-1,3,5-triazin-2-yl)amino)-2-fluoro-N-methyl-benzamide;
N-methyl-3-((4-(3-((4-(trifluoromethyl)phenoxy)methyl)-1-azetidinyl)-1,3,5-triazin-2-yl)amino)benzamide;
2-fluoro-N-methyl-5-((4-(3-(4-(trifluoromethyl)phenoxy)-1-azetidinyl)-1,3,5-triazin-2-yl)amino)benzamide;
3-((2-(3-(4-chlorophenoxy)-1-azetidinyl)-4-pyrimidinyl)amino)-N-methylbenzamide;
3-((4-(3-(4-chloro-3-methylphenoxy)-1-azetidinyl)-1,3,5-triazin-2-yl)amino)-N-methylbenzamide;
2-chloro-N-methyl-5-((4-(6-(2,2,2-trifluoroethoxy)-3,4-dihydro-2(1H)-isoquinolinyl)-1,3,5-triazin-2-yl)amino)benzamide;
3-((4-(3-(4-fluorophenoxy)-1-azetidinyl)-2-pyrimidinyl)amino)-N-methylbenzamide;
3-((4-(3-(4-chloro-3-fluorophenoxy)-1-azetidinyl)-1,3,5-triazin-2-yl)amino)-N-methylbenzamide;
N-methyl-3-((4-((3-(4-(trifluoromethoxy)phenoxy)propyl)amino)-1,3,5-triazin-2-yl)-amino)benzamide;
5-((4-(3-(4-chloro-2-fluorophenoxy)-1-azetidinyl)-1,3,5-triazin-2-yl)amino)-2-fluoro-N-methylbenzamide;
3-((4-(3-(3-chloro-4-fluorophenoxy)-1-azetidinyl)-1,3,5-triazin-2-yl)amino)-N-methylbenzamide;
3-((4-(3-(4-fluoro-2-methylphenoxy)-1-azetidinyl)-1,3,5-triazin-2-yl)amino)-N-methylbenzamide;
3-((4-(3-(3-ethylphenoxy)-1-azetidinyl)-1,3,5-triazin-2-yl)amino)-N-methylbenzamide;
3-((4-(3-(2,5-dichlorophenoxy)-1-azetidinyl)-1,3,5-triazin-2-yl)amino)-N-methyl-benzamide;
3-((4-(3-(4-chloro-2-methylphenoxy)-1-azetidinyl)-1,3,5-triazin-2-yl)amino)-N-methylbenzamide;
3-((4-(3-(4-chloro-2-fluorophenoxy)-1-azetidinyl)-1,3,5-triazin-2-yl)amino)-N-methylbenzamide;
3-((4-(3-(2,3-dihydro-1H-inden-5-yloxy)-1-azetidinyl)-1,3,5-triazin-2-yl)amino)-N-methylbenzamide;
N-methyl-3-((4-(4-(3-(trifluoromethoxy)phenyl)-1-piperazinyl)-1,3,5-triazin-2-yl)-amino)benzamide;
N-methyl-3-((4-(4-(4-phenyl-1,3-thiazol-2-yl)-1-piperidinyl)-1,3,5-triazin-2-yl)-amino)benzamide;
3-((4-(3-(3-chlorophenoxy)-1-azetidinyl)-1,3,5-triazin-2-yl)amino)-N-methyl-benzamide;
N-methyl-3-((4-(4-(2-phenyl-1,3-thiazol-4-yl)-1-piperidinyl)-1,3,5-triazin-2-yl)-amino)benzamide;
2-chloro-N-methyl-5-((4-(4-(4-phenyl-1,3-thiazol-2-yl)-1-piperidinyl)-1,3,5-triazin-2-yl)-amino)benzamide;

3-((4-(3-(4-chlorophenoxy)-1-azetidinyl)-1,3,5-triazin-2-yl)
  amino)-N-(2-methoxy-ethyl)benzamide;
3-((4-(3-(2-chlorophenoxy)-1-azetidinyl)-1,3,5-triazin-2-yl)
  amino)-N-methyl-benzamide;
3-((4-(3-(4-chlorophenoxy)-1-azetidinyl)-2-pyrimidinyl)
  amino)-N-methylbenzamide;
3-((4-(3-(2-chloro-4-methylphenoxy)-1-azetidinyl)-1,3,5-
  triazin-2-yl)amino)-N-methylbenzamide;
N-methyl-3-((4-(3-phenoxy-1-azetidinyl)-1,3,5-triazin-2-
  yl)amino)benzamide;
N-methyl-3-((4-(4-(4-methylphenyl)-1-piperazinyl)-1,3,5-
  triazin-2-yl)amino)-benzamide;
N-methyl-3-((4-(3-(4-(trifluoromethyl)phenoxy)-1-azetidi-
  nyl)-1,3,5-triazin-2-yl)-amino)benzamide;
3-((4-(4-((4-chlorophenyl)carbonyl)-1-piperidinyl)-1,3,5-
  triazin-2-yl)amino)-N-methylbenzamide;
3-((4-(3-(4-chlorophenoxy)-1-azetidinyl)-1,3,5-triazin-2-yl)
  amino)-5-fluoro-N-methylbenzamide;
3-((4-(3-(4-fluorophenoxy)-1-azetidinyl)-1,3,5-triazin-2-yl)
  amino)-N-(2-methoxy-ethyl)benzamide;
3-((4-(3-((4-chlorophenoxy)methyl)-1-azetidinyl)-1,3,5-tri-
  azin-2-yl)amino)-N-methylbenzamide;
N-methyl-3-((4-(6-(2,2,2-trifluoroethoxy)-3,4-dihydro-2
  (1H)-isoquinolinyl)-1,3,5-triazin-2-yl)amino)benzamide;
N-methyl-3-((4-(3-(4-(1-methylethyl)phenoxy)-1-azetidi-
  nyl)-1,3,5-triazin-2-yl)amino)benzamide;
N-methyl-3-((4-(4-(3-(trifluoromethyl)phenyl)-1-piperazi-
  nyl)-1,3,5-triazin-2-yl)amino)benzamide;
3-((4-(4-(3-methoxyphenyl)-1-piperazinyl)-1,3,5-triazin-2-
  yl)amino)-N-methyl-benzamide; or
N-methyl-3-((4-(4-phenoxy-1-piperidinyl)-1,3,5-triazin-2-
  yl)amino)benzamide, or a pharmaceutically acceptable
  salt thereof.

In another particular aspect of the compounds of Formula
(I), the compound is:
3-(4-(3-(2,4-dichlorophenoxy)azetidin-1-yl)pyrimidin-2-
  ylamino)-N-methylbenzamide;
3-(4-(3-(3,4-dichlorophenoxy)azetidin-1-yl)pyrimidin-2-
  ylamino)-N-methylbenzamide;
N-methyl-3-((4-(3-(4-methylphenoxy)-1-azetidinyl)-2-pyri-
  midinyl)amino)benzamide;
N-methyl-3-((4-(3-(4-(trifluoromethyl)phenoxy)-1-azetidi-
  nyl)-2-pyrimidinyl)amino)benzamide;
3-((4-(3-(4-methoxyphenoxy)-1-azetidinyl)-2-pyrimidinyl)
  amino)-N-methylbenzamide;
3-((4-(3-(3,4-difluorophenoxy)-1-azetidinyl)-2-pyrimidi-
  nyl)amino)-N-methylbenzamide;
3-((4-(3-(3-chloro-4-fluorophenoxy)-1-azetidinyl)-2-pyrim-
  idinyl)amino)-N-methylbenzamide;
3-((4-(3-(4-fluoro-3-methylphenoxy)-1-azetidinyl)-2-pyri-
  midinyl)amino)-N-methylbenzamide;
3-((4-(3-(2,4-difluorophenoxy)-1-azetidinyl)-2-pyrimidi-
  nyl)amino)-N-methylbenzamide;
3-((4-(3-(2-chloro-4-fluorophenoxy)-1-azetidinyl)-2-pyrim-
  idinyl)amino)-N-methylbenzamide;
3-((4-(3-(4-fluoro-2-methylphenoxy)-1-azetidinyl)-2-pyri-
  midinyl)amino)-N-methylbenzamide;
3-((4-(3-(4-chloro-3-fluorophenoxy)-1-azetidinyl)-2-pyrim-
  idinyl)amino)-N-methylbenzamide;
3-((4-(3-(4-chloro-3-methylphenoxy)-1-azetidinyl)-2-pyri-
  midinyl)amino)-N-methylbenzamide;
3-((4-(3-(4-chloro-2-fluorophenoxy)-1-azetidinyl)-2-pyrim-
  idinyl)amino)-N-methylbenzamide;
3-((4-(3-(4-chloro-2-methylphenoxy)-1-azetidinyl)-2-pyri-
  midinyl)amino)-N-methylbenzamide;
3-((4-(3-((4-chlorophenoxy)methyl)-1-azetidinyl)-2-pyrim-
  idinyl)amino)-N-methylbenzamide;
N-methyl-3-((4-(3-(4-methylphenoxy)methyl)-1-azetidi-
  nyl)-2-pyrimidinyl)amino)benzamide;
3-(4-(3-(4-chloro-2-fluorophenoxy)azetidin-1-yl)-1,3,5-tri-
  azin-2-ylamino)-N-methylbenzamide;
3-(4-(3-(4-chloro-2-fluorophenoxy)azetidin-1-yl)-1,3,5-tri-
  azin-2-ylamino)-N-ethylbenzamide;
3-(4-(3-(4-chloro-2-fluorophenoxy)azetidin-1-yl)-1,3,5-tri-
  azin-2-ylamino)-5-fluoro-N-methylbenzamide;
3-(4-(3-(4-chloro-2-fluorophenoxy)azetidin-1-yl)pyridin-2-
  ylamino)-N-methylbenzamide;
3-((2-(3-(4-fluorophenoxy)-1-azetidinyl)-4-pyridinyl)
  amino)-N-methylbenzamide;
3-((6-(3-(4-chloro-2-fluorophenoxy)-1-azetidinyl)-2-pyridi-
  nyl)amino)-N-methylbenzamide;
5-((6-(3-(4-chloro-2-fluorophenoxy)-1-azetidinyl)-2-pyridi-
  nyl)amino)-2-fluoro-N-methylbenzamide;
2-chloro-5-((6-(3-(4-chloro-2-fluorophenoxy)-1-azetidi-
  nyl)-2-pyridinyl)amino)-N-methylbenzamide;
3-((6-(3-(4-chloro-2-fluorophenoxy)-1-azetidinyl)-4-pyrim-
  idinyl)amino)-N-methylbenzamide;
3-((2-(3-(4-chloro-2-fluorophenoxy)-1-azetidinyl)-4-pyridi-
  nyl)amino)-N-methylbenzamide;
3-((6-(3-(4-chloro-2-fluorophenoxy)-1-azetidinyl)-5-fluoro-
  4-pyrimidinyl)amino)-N-methylbenzamide;
N-methyl-3-((2-((3-(4-(trifluoromethoxy)phenoxy)propyl)
  amino)-4-pyrimidinyl)amino)benzamide;
N,2-dimethyl-3-((4-(4-((4-(trifluoromethoxy)benzyl)oxy)-
  1-piperidinyl)-1,3,5-triazin-2-yl)amino)benzamide;
3-((4-(3-(4-chloro-2-fluorophenoxy)-1-azetidinyl)-1,3,5-tri-
  azin-2-yl)oxy)-N-methylbenzamide;
3-((3-(3-(4-fluorophenoxy)-1-azetidinyl)phenyl)amino)-N-
  methylbenzamide;
3-((3-(3-(4-chloro-2-fluorophenoxy)-1-azetidinyl)phenyl)
  amino)-N-methylbenzamide;
3-((5-fluoro-2-(3-(4-fluorophenoxy)-1-azetidinyl)-4-pyrim-
  idinyl)amino)-N-methylbenzamide;
N-methyl-3-((4-(6-(2,2,2-trifluoroethoxy)-3,4-dihydro-2
  (1H)-isoquinolinyl)-2-pyrimidinyl)amino)benzamide;
3-((2-(3-(4-chloro-2-fluorophenoxy)-1-azetidinyl)-4-pyrim-
  idinyl)amino)-N-methylbenzamide; or
3-((2-(3-(4-chloro-2-fluorophenoxy)-1-azetidinyl)-5-fluoro-
  4-pyrimidinyl)amino)-N-methylbenzamide; or a pharma-
  ceutically acceptable salt thereof.

In another aspect, provided is a pharmaceutical composition comprising a compound of Formula (I) or a pharmaceutically acceptable salt thereof and a pharmaceutically acceptable excipient.

In still another aspect, provided is a method of treating a disease by inhibition of voltage-gated sodium channel in a patient which method comprises administering to the patient a therapeutically effective amount of a compound of Formula (I):

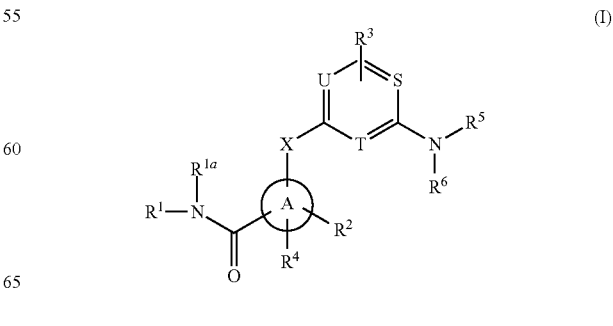

where:
X is —NH—, —NMe-, —O—, or —S—;
S, T and U are independently —CR³— or —N—;
A is aryl or heteroaryl;
R¹ is hydrogen, alkyl, haloalkyl, substituted alkyl, acyloxyalkyl, cycloalkyl, heterocyclyl, aryl, heteroaryl, cycloalkylalkyl, heterocyclylalkyl, aralkyl, or heteroaralkyl wherein the ring in cycloalkyl, heterocyclyl, aryl, heteroaryl, cycloalkylalkyl, heterocyclylalkyl, aralkyl, or heteroaralkyl is optionally substituted with one to three substitutents independently selected from alkyl, halo, haloalkyl, alkoxy, hydroxyl, or haloalkoxy;
$R^{1a}$ is hydrogen or alkyl;
$R^2$ is hydrogen, alkyl, substituted alkyl, aryl, heteroaryl, cycloalkyl, halo, haloalkyl, haloalkoxy, alkoxy, alkoxyalkoxy, hydroxyl, carboxy, alkoxycarbonyl, cyano, amino, monosubstituted or disubstitued amino, sulfonyl, or alkoxyalkyl;
each $R^3$ is independently hydrogen, halo, alkyl, alkoxy, cyano, or haloalkyl;
$R^4$ is hydrogen, alkyl, substituted alkyl, halo, alkoxy, hydroxy, carboxy, —CONH₂, —CONMe₂, cycloalkyl, or dialkylamino;
$R^5$ is hydrogen, alkyl, substituted alkyl, aryl, or heteroaryl;
$R^6$ is aryl, heteroaryl, heteroaralkyl, heterocyclyl, heterocyclylalkyl, cycloalkyl, or aralkyl wherein one or two carbon atoms in the alkyl chain in aralkyl are optionally replaced by —N—, —O—, or —CO— provided that —N—, —O—, or —CO— are not on adjacent atoms; or
$R^5$ and $R^6$ together with the nitrogen atom to which they are attached form ring B having the formula:

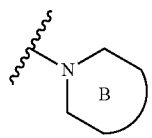

wherein ring B is a heteroaryl, heterocyclyl, bridged heterocyclyl, or spiroheterocyclyl ring, and
wherein each aforementioned ring in $R^5$, $R^6$ and ring B is substituted with $R^a$, $R^b$ or $R^c$ where $R^a$ is hydrogen, alkyl, halo, haloalkyl, haloalkoxy, alkylthio, haloalkylthio, cyano, hydroxy, alkoxy, amino, monosubstituted amino, disubstituted amino, sulfonyl, thio, acyl, carboxy, alkoxycarbonyl, hydroxyalkyl, alkoxyalkyl, aminoalkyl, hydroxyalkoxy, hydroxyalkoxyalkyl, alkoxyalkoxy, aminoalkoxy, aminosulfonyl, aminocarbonyl, or acylamino and $R^b$ and $R^c$ are independently selected from hydrogen, alkyl, substituted alkyl, substituted alkynyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, sulfonylamino, aryl, heteroaryl, cycloalkyl, cycloalkenyl, heterocyclyl, aralkyl, heteroaralkyl, heterocyclylalkyl, aryloxy, heteroaryloxy, cycloalkoxy, aryloxyalkyl, aralkyloxy, aralkyloxyalkyl, aralkylthio, heteroaralkyloxy, heterocyclylalkyloxy, cycloalkylalkyloxy or cycloalkylalkyloxyalkyl where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, cyanoalkyl, alkylthio, cyano, hydroxy, alkoxy, amino, mono-substituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, cycloalkyl, cycloalkenyl, phenyl, phenxoy, heteroaryl, heterocyclyl, heterocyclylalkyl, aralkyl, aralkyloxy or heteroaralkyl and where the aromatic or alicyclic ring in $R^d$, $R^e$ or $R^f$ is optionally substituted with one to three substituents independently selected from alkyl, halo, haloalkyl, haloalkyloxy, hydroxyl, alkoxy, acetylamino, alkylsulfonyl, or cyano; or a pharmaceutically acceptable salt thereof.

In one embodiment of the method, the disease is chronic pain. In another aspect, the embodiment is chronic pain associated with, but are not limited to, post-herpetic neuralgia (shingles), osteoarthritis, painful diabetic neuropathy, complex regional pain syndrome (CRPS), cancer- or chemotherapy-induced pain, chronic back pain, phantom limb pain, trigeminal neuralgia, HIV-induced neuropathy, cluster headache disorders, and migraine, Primary Erythromelalgia, and Paroxysmal Extreme Pain Disorder. Other potential indications for Nav1.7 inhibitors include but are not limited to depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, Jan. 28 (epub)).

In another aspect this invention is directed to use of the compounds of Formula (I) as a medicament. In one aspect, the medicament is used in the treatment of chronic pain. In another aspect, the embodiment is chronic pain associated with, but are not limited to, post-herpetic neuralgia (shingles), osteoarthritis, painful diabetic neuropathy, complex regional pain syndrome (CRPS), cancer- or chemotherapy-induced pain, chronic back pain, phantom limb pain, trigeminal neuralgia, HIV-induced neuropathy, cluster headache disorders, and migraine, Primary Erythromelalgia, and Paroxysmal Extreme Pain Disorder. Other potential indications include but are not limited to depression, bipolar and other CNS disorders, multiple sclerosis, Parkinson's disease, restless legs syndrome, ataxia, tremor, muscle weakness, dystonia, tetanus, anxiety, depression, learning and memory, cognition, cardiac arrhythmia and fibrillation, contractility, congestive heart failure, sick sinus syndrome, schizophrenia, neuroprotection after stroke, drug and alcohol abuse, Alzheimer's, and cancer.

In another aspect this invention is directed compounds of Formula (I) for use in the treatment of chronic pain. In another aspect, the embodiment is chronic pain associated with, but not limited to, post-herpetic neuralgia (shingles), osteoarthritis, painful diabetic neuropathy, complex regional pain syndrome (CRPS), cancer- or chemotherapy-induced pain, chronic back pain, phantom limb pain, trigeminal neuralgia, HIV-induced neuropathy, cluster headache disorders, and migraine, Primary Erythromelalgia, and Paroxysmal Extreme Pain Disorder. Other potential indications include but are not limited to depression, bipolar and other CNS disorders, multiple sclerosis, Parkinson's disease, restless legs syndrome, ataxia, tremor, muscle weakness, dystonia, tetanus, anxiety, depression, learning and memory, cognition, cardiac arrhythmia and fibrillation, contractility, congestive heart failure, sick sinus syndrome, schizophrenia, neuroprotection after stroke, drug and alcohol abuse, Alzheimer's, and cancer.

DETAILED DESCRIPTION OF THE INVENTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alicyclic" means a non-aromatic ring, e.g., cycloalkyl or heterocyclyl ring.

"Alkylene" means a linear saturated divalent hydrocarbon radical of one to six carbon atoms or a branched saturated divalent hydrocarbon radical of three to six carbon atoms unless otherwise stated, e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means an —NH$_2$ group.

"Alkylamino" means an —NHR radical where R is alkyl as defined above, e.g., methylamino, ethylamino, propylamino, or 2-propylamino, and the like.

"Alkoxy" means an —OR radical where R is alkyl as defined above, e.g., methoxy, ethoxy, propoxy, or 2-propoxy, n-, iso-, or tert-butoxy, and the like.

"Alkoxycarbonyl" means a —C(O)OR radical where R is alkyl as defined above, e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" or "alkoxyalkoxy" means an —OR radical where R is alkoxyalkyl as defined above, e.g., methoxyethoxy, 2-ethoxyethoxy, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, each as defined above, and R' is selected from hydrogen, alkyl, hydroxyalkyl, alkoxyalkyl, aryl, aralkyl, heteroaryl, heteroaralkyl, or haloalkyl, each as defined herein, e.g., aminomethyl, methylaminoethyl, 2-ethylamino-2-methylethyl, 1,3-diaminopropyl, dimethylaminomethyl, diethylaminoethyl, acetylaminopropyl, and the like.

"Aminoalkoxy" means an —OR radical where R is aminoalkyl as defined above, e.g., 2-aminoethoxy, 2-dimethylaminopropoxy, and the like.

"Aminocarbonyl" means a —CONRR' radical where R is independently hydrogen, alkyl, hydroxyalkyl, alkoxyalkyl, or aminoalkyl, each as defined herein and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —CONH$_2$, methylaminocarbonyl, 2-dimethylaminocarbonyl, and the like.

"Aminosulfonyl" means a —SO$_2$NRR' radical where R is independently hydrogen, alkyl, hydroxyalkyl, alkoxyalkyl, or aminoalkyl, each as defined herein and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —SO$_2$NH$_2$, methylaminosulfonyl, 2-dimethylaminosulfonyl, and the like.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetyl, propionyl, benzoyl, pyridinylcarbonyl, and the like. When R is alkyl, the radical is also referred to herein as alkylcarbonyl.

"Acyloxyalkyl" means an -alkyleneOCOR radical where R is alkyl as defined above.

"Acylamino" means an —NHCOR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetylamino, propionylamino, and the like.

"Aryl" means a monovalent monocyclic or bicyclic aromatic hydrocarbon radical of 6 to 10 ring atoms e.g., phenyl or naphthyl.

"Aralkyl" means an -(alkylene)-R radical where R is aryl as defined above.

"Aryloxy" means an —OR radical where R is aryl as defined above, e.g., phenoxy, naphthyloxy.

"Aryloxyalkyl" means an -alkylene-OR radical where R is aryl as defined above, e.g., phenoxymethyl, phenoxyethyl, and the like.

"Aralkyloxy" means an —OR radical where R is aralkyl as defined above.

"Aralkyloxyalkyl" means an -(alkylene)-OR radical where R is aralkyl as defined above.

"Aralkylthio" means a —SR radical where R is aralkyl as defined above.

"Bridged heterocyclyl" means a saturated or unsaturated monovalent bicyclic group of 5 to 10 ring atoms in which one or two ring atoms are heteroatom selected from N, O, or S(O)$_n$, where n is an integer from 0 to 2, the remaining ring atoms being C, where some of the rings are created by one or more bridges. Representative examples include, but are not limited to:

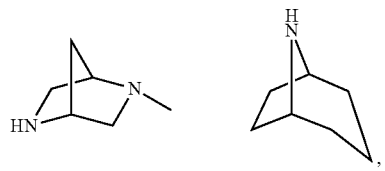

and the like.

"Cycloalkyl" means a cyclic, saturated, monovalent hydrocarbon radical of three to ten carbon atoms, e.g., cyclopropyl, cyclobutyl, cyclopentyl, or cyclohexyl, and the like. The cycloalkyl ring can optionally be fused to phenyl or monocyclic heteroaryl ring as defined herein. When the cycloalkyl ring is referred to herein as "fused cycloalkyl", it means that the cycloalkyl ring is fused to phenyl or monocyclic heteroaryl ring. When the cycloalkyl ring is referred to herein as "monocyclic cycloalkyl", it means that the cycloalkyl ring is not fused to phenyl or monocyclic heteroaryl ring.

"Cycloalkylalkyl" means an -(alkylene)-R radical where R is cycloalkyl as defined above; e.g., cyclopropylmethyl, cyclobutylmethyl, cyclopentylethyl, or cyclohexylmethyl, and the like.

"Cycloalkoxy" means an —OR radical where R is cycloalkyl as defined above, e.g., cyclopropoxy, cyclobutoxy, and the like.

"Cycloalkylalkyloxy" means an —OR radical where R is cycloalkylalkyl as defined above.

"Cycloalkylalkyloxyalkyl" means an -(alkylene)-OR radical where R is cycloalkylalkyl as defined above.

"Cycloalkenyl" means a cyclic unsaturated monovalent hydrocarbon radical of three to ten carbon atoms containing one or two double bond(s), e.g., cyclopropenyl, cyclobutenyl, cyclopentenyl, or cyclohexenyl, and the like.

"Carboxy" means —COOH.

"Cyanoalkyl" means alkyl radical as defined above where one of the hydrogen atoms in the alkyl chain is replaced by cyano.

"Disubstituted amino" means an —NRR' radical where R and R' are independently alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., dimethylamino, phenylmethylamino, and the like. When R and R' are alkyl, the group is referred to herein as dialkylamino "Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Haloalkylthio" means a —SR radical where R is haloalkyl as defined above, e.g., —SCF$_3$, —SCH$_2$CF$_3$, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, or 1-(hydroxymethyl)-2-hydroxyethyl.

"Hydroxyalkoxy" or "hydroxyalkyloxy" means a —OR radical where R is hydroxyalkyl as defined above.

"Hydroxyalkoxyalkyl" or "hydroxyalkyloxyalkyl" means a -(alkylene)-OR radical where R is hydroxyalkyl as defined above.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, tetrahydroisoquinolinyl, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl. It will be apparent to a person skilled in the art, that when ring B in Formula (I) is heterocyclyl, there is at least one nitrogen atom present in the heterocyclyl ring.

"Heterocyclylalkyl" means an -(alkylene)-R radical where R is heterocyclyl ring as defined above e.g., tetraydrofuranylmethyl, piperazinylmethyl, morpholinylethyl, and the like.

"Heterocyclylalkyloxy" means an —OR radical where R is heterocyclylalkyl as defined above.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. It will be apparent to a person skilled in the art, that when ring B in Formula (I) is heteroaryl, there is at least one nitrogen atom present in the heteroaryl ring.

"Heteroaralkyl" means an -(alkylene)-R radical where R is heteroaryl as defined above.

"Heteraryloxy" means an —OR radical where R is heteroaryl as defined above, e.g., pyridinyloxy, thiophenyloxy, and the like.

"Heteroaralkyloxy" means an —OR radical where R is heteroaralkyl as defined above.

"Monosubstituted amino" means an —NHR radical where R is alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., methylamino, 2-phenylamino, hydroxyethylamino, and the like. When R is alkyl, the group is referred to herein as monoalkylamino.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present invention can also exist as cocrystals.

The compounds of the present invention may have asymmetric centers. Compounds of the present invention containing an asymmetrically substituted atom may be isolated in optically active, racemic forms or other mixtures of isomers. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this invention. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this invention.

"Oxo" or "carbonyl" means an =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Sulfonyl" means a —SO$_2$R radical where R is alkyl, haloalkyl, aryl, aralkyl, heteroaryl, heteroaralkyl, heterocyclyl, heterocyclylalkyl, each as defined herein, e.g., methylsulfonyl, phenylsulfonyl, benzylsulfonyl, pyridinylsulfonyl, and the like. When R is alkyl, it is also referred to herein as alkylsulfonyl.

"Sulfonylamino" means an —NHSO$_2$R radical where R is alkyl, haloalkyl, aryl, aralkyl, heteroaryl, heteroaralkyl, heterocyclyl, heterocyclylalkyl, each as defined herein.

"Spiroheterocyclyl" means a bicyclic compound ring of 6 to 14, preferably 6 to 12 carbon ring atoms where the rings are connected through one carbon atom and in which one or two ring atoms are heteroatom selected from N, O, or S(O)$_n$, where n is an integer from 0 to 2, the remaining ring atoms being C. The spiroheterocyclyl ring optionally contains one or two oxo group within the ring and is optionally substituted with phenyl or monocyclic heteroaryl ring. Representative examples include, but are not limited to,

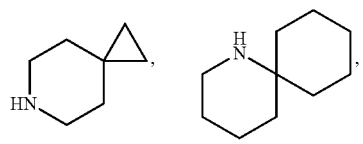

and the like. It will be apparent to a person skilled in the art, that when ring B in Formula (I) is spiroheterocyclyl, there is at least one nitrogen atom present in the spiroheterocyclyl ring.

"Substituted alkyl" means a linear saturated monovalent hydrocarbon radical of one to six carbon atoms or a branched saturated monovalent hydrocarbon radical of three to six carbon atoms where one or two hydrogen atoms in the alkyl chain are independently replaced by hydroxyl, halo, alkoxy, amino, monosubstituted amino, disubstituted amino, cyano, sulfonyl, aminocarbonyl, aminosulfonyl, —NHCONH$_2$, carboxy, acyl, acylamino, phenyl, or alkoxycarbonyl, each group as defined herein.

"Substituted alkynyl" means a linear saturated monovalent hydrocarbon radical of two to six carbon atoms or a branched monovalent hydrocarbon radical of three to six carbon atoms containing a triple bond where one or two hydrogen atoms in the alkynyl chain are independently replaced by phenyl, hydroxyl, alkoxy, amino, monosubstituted amino, disubstituted amino, cyano, sulfonyl, aminocarbonyl, aminosulfonyl, —NHCONH$_2$, carboxy, acyl, acylamino, or alkoxycarbonyl, each group as defined herein.

"Thio" means a —SR radical where R is alkyl, aryl, aralkyl, heteroaryl, heteroaralkyl, heterocyclyl, heterocyclylalkyl, each as defined herein, e.g., methylthio, phenylthio, benzylthio, pyridinylthio, and the like. When R is alkyl, it is also referred to herein as alkylthio.

The phrase in the definition of ring B in the claims and in the specification of this Application " . . . ring B is a heteroaryl, heterocyclyl, bridged heterocylcyl, or spiroheterocyclyl ring, each ring substituted with R$^a$, R$^b$ or R$^c$ . . . " and similar phrases used for others groups in the claims and in the specification with respect to the compound of Formula (I) means that the rings can be unsubstituted, mono-, di-, or trisubstituted unless indicated otherwise.

"Treating" or "treatment" of a disease includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

Representative compounds of the Invention are set forth is Table 1 below.

TABLE 1

| Compound Number | Name | Mass Spec. | hNav1.7 IC$_{50}$ (μM) (AVG) |
|---|---|---|---|
| 1 | 3-((4-(3-(4-fluoro-2-methylphenoxy)-1-azetidinyl)-2-pyrimidinyl)amino)-N-methylbenzamide | 408 | 0.08 |
| 2 | 3-((4-(3-(4-chlorophenoxy)-1-azetidinyl)-1,3,5-triazin-2-yl)amino)-N-methylbenzamide | 411 | 0.15 |
| 3 | 2-fluoro-N-methyl-5-((4-(4-(4-phenyl-1,3-thiazol-2-yl)-1-piperidinyl)-1,3,5-triazin-2-yl)amino)benzamide | 490.2 | 0.17 |
| 4 | 5-((4-(3-(4-chlorophenoxy)-1-azetidinyl)-1,3,5-triazin-2-yl)amino)-2-fluoro-N-methylbenzamide | 429 | 0.19 |
| 5 | N-methyl-3-((4-(3-((4-(trifluoromethyl)phenoxy)methyl)-1-azetidinyl)-1,3,5-triazin-2-yl)amino)benzamide | 459.2 | 0.20 |
| 6 | 2-fluoro-N-methyl-5-((4-(3-(4-(trifluoromethyl)phenoxy)-1-azetidinyl)-1,3,5-triazin-2-yl)amino)benzamide | 462 | 0.21 |
| 7 | 3-((2-(3-(4-chlorophenoxy)-1-azetidinyl)-4-pyrimidinyl)amino)-N-methylbenzamide | 410.0 | 0.21 |
| 8 | 3-((4-(3-(4-chloro-3-methylphenoxy)-1-azetidinyl)-1,3,5-triazin-2-yl)amino)-N-methylbenzamide | 425 | 0.23 |
| 9 | 2-chloro-N-methyl-5-((4-(6-(2,2,2-trifluoroethoxy)-3,4-dihydro-2(1H)-isoquinolinyl)-1,3,5-triazin-2-yl)amino)benzamide | 493.2 | 0.23 |
| 10 | 3-((4-(3-(4-fluorophenoxy)-1-azetidinyl)-2-pyrimidinyl)amino)-N-methylbenzamide | 394.0 | 0.25 |
| 11 | 3-((4-(3-(4-chloro-3-fluorophenoxy)-1-azetidinyl)-1,3,5-triazin-2-yl)amino)-N-methylbenzamide | 429 | 0.25 |
| 12 | 3-((4-(3-(4-chloro-2-methylphenoxy)-1-azetidinyl)-2-pyrimidinyl)amino)-N-methylbenzamide | 424 | 0.26 |
| 13 | N-methyl-3-((4-((3-(4-(trifluoromethoxy)phenoxy)propyl)amino)-1,3,5-triazin-2-yl)amino)benzamide | 463.2 | 0.27 |
| 14 | 5-((4-(3-(4-chloro-2-fluorophenoxy)-1-azetidinyl)-1,3,5-triazin-2-yl)amino)-2-fluoro-N-methylbenzamide | 447.2 | 0.28 |
| 15 | 3-((4-(3-(3-chloro-4-fluorophenoxy)-1-azetidinyl)-1,3,5-triazin-2-yl)amino)-N-methylbenzamide | 429 | 0.28 |
| 16 | 3-((4-(3-(4-fluoro-2-methylphenoxy)-1-azetidinyl)-1,3,5-triazin-2-yl)amino)-N-methylbenzamide | 409 | 0.29 |
| 17 | 3-((4-(3-(3-ethylphenoxy)-1-azetidinyl)-1,3,5-triazin-2-yl)amino)-N-methylbenzamide | 405 | 0.30 |
| 18 | 3-((4-(3-(2,5-dichlorophenoxy)-1-azetidinyl)-1,3,5-triazin-2-yl)amino)-N-methylbenzamide | 445 | 0.31 |

TABLE 1-continued

| Compound Number | Name | Mass Spec. | hNav1.7 IC$_{50}$ (μM) (AVG) |
|---|---|---|---|
| 19 | 3-((4-(3-(4-chloro-3-methylphenoxy)-1-azetidinyl)-2-pyrimidinyl)amino)-N-methylbenzamide | 424 | 0.31 |
| 20 | 3-((4-(3-(4-chloro-2-methylphenoxy)-1-azetidinyl)-1,3,5-triazin-2-yl)amino)-N-methylbenzamide | 425 | 0.32 |
| 21 | 3-((4-(3-(4-chloro-2-fluorophenoxy)-1-azetidinyl)-1,3,5-triazin-2-yl)amino)-N-methylbenzamide | 429 | 0.33 |
| 22 | 3-((4-(3-(2,3-dihydro-1H-inden-5-yloxy)-1-azetidinyl)-1,3,5-triazin-2-yl)amino)-N-methylbenzamide | 417 | 0.35 |
| 23 | N-methyl-3-((4-(4-(3-(trifluoromethoxy)phenyl)-1-piperazinyl)-1,3,5-triazin-2-yl)amino)benzamide | 474.2 | 0.35 |
| 24 | N-phenyl-3-((4-(4-(4-phenyl-1,3-thiazol-2-yl)-1-piperidinyl)-1,3,5-triazin-2-yl)amino)benzamide | 472 | 0.38 |
| 25 | 3-((4-(3-(3-chlorophenoxy)-1-azetidinyl)-1,3,5-triazin-2-yl)amino)-N-methylbenzamide | 411 | 0.38 |
| 26 | N-methyl-3-((4-(4-(2-phenyl-1,3-thiazol-4-yl)-1-piperidinyl)-1,3,5-triazin-2-yl)amino)benzamide | 472.2 | 0.39 |
| 27 | 2-chloro-N-methyl-5-((4-(4-(4-phenyl-1,3-thiazol-2-yl)-1-piperidinyl)-1,3,5-triazin-2-yl)amino)benzamide | 506.2 | 0.40 |
| 28 | 3-((4-(3-(4-chlorophenoxy)-1-azetidinyl)-1,3,5-triazin-2-yl)amino)-N-(2-methoxyethyl)benzamide | 455.1 | 0.40 |
| 29 | 3-((4-(3-(2-chlorophenoxy)-1-azetidinyl)-1,3,5-triazin-2-yl)amino)-N-methylbenzamide | 411 | 0.42 |
| 30 | 3-((4-(3-(4-chlorophenoxy)-1-azetidinyl)-2-pyrimidinyl)amino)-N-methylbenzamide | 410.0 | 0.43 |
| 31 | 3-((4-(3-(4-methoxyphenoxy)-1-azetidinyl)-2-pyrimidinyl)amino)-N-methylbenzamide | 406 | 0.43 |
| 32 | 3-((4-(3-(2-chloro-4-methylphenoxy)-1-azetidinyl)-1,3,5-triazin-2-yl)amino)-N-methylbenzamide | 425 | 0.44 |
| 33 | N-methyl-3-((4-(3-phenoxy-1-azetidinyl)-1,3,5-triazin-2-yl)amino)benzamide | 377 | 0.45 |
| 34 | N-methyl-3-((4-(4-(4-methylphenyl)-1-piperazinyl)-1,3,5-triazin-2-yl)amino)benzamide | 404 | 0.47 |
| 35 | N-methyl-3-((4-(3-(4-(trifluoromethyl)phenoxy)-1-azetidinyl)-1,3,5-triazin-2-yl)amino)benzamide | 445 | 0.47 |
| 36 | 3-((4-(4-((4-chlorophenyl)carbonyl)-1-piperidinyl)-1,3,5-triazin-2-yl)amino)-N-methylbenzamide | 451 | 0.49 |
| 37 | 3-((4-(3-(4-chlorophenoxy)-1-azetidinyl)-1,3,5-triazin-2-yl)amino)-5-fluoro-N-methylbenzamide | 429 | 0.49 |
| 38 | 3-((4-(3-(4-fluorophenoxy)-1-azetidinyl)-1,3,5-triazin-2-yl)amino)-N-(2-methoxyethyl)benzamide | 439 | 0.50 |
| 39 | 3-((4-(3-(3,4-dichlorophenoxy)-1-azetidinyl)-1,3,5-triazin-2-yl)amino)-N-methylbenzamide | 445 | 0.50 |
| 40 | 3-((4-(3-((4-chlorophenoxy)methyl)-1-azetidinyl)-1,3,5-triazin-2-yl)amino)-N-methylbenzamide | 425 | 0.50 |
| 41 | N-methyl-3-((4-(6-(2,2,2-trifluoroethoxy)-3,4-dihydro-2(1H)-isoquinolinyl)-1,3,5-triazin-2-yl)amino)benzamide | 459.2 | 0.52 |
| 42 | N-methyl-3-((4-(3-(4-(1-methylethyl)phenoxy)-1-azetidinyl)-1,3,5-triazin-2-yl)amino)benzamide | 419 | 0.57 |
| 43 | N-methyl-3-((4-(4-(3-(trifluoromethyl)phenyl)-1-piperazinyl)-1,3,5-triazin-2-yl)amino)benzamide | 458 | 0.60 |
| 44 | 3-((4-(4-(3-methoxyphenyl)-1-piperazinyl)-1,3,5-triazin-2-yl)amino)-N-methylbenzamide | 420 | 0.61 |
| 45 | N-methyl-3-((4-(4-phenoxy-1-piperidinyl)-1,3,5-triazin-2-yl)amino)benzamide | 405.2 | 0.63 |
| 46 | N-methyl-3-((4-(4-(2-phenyl-1,3-thiazol-4-yl)-3,6-dihydro-1(2H)-pyridinyl)-1,3,5-triazin-2-yl)amino)benzamide | 470 | 0.63 |
| 47 | 3-((4-(3-((4-chlorophenoxy)methyl)-1-azetidinyl)-1,3,5-triazin-2-yl)amino)-N-(2-methoxyethyl)benzamide | 469.2 | 0.64 |
| 48 | 3-((4-(4-(3-fluorophenoxy)-1-piperidinyl)-1,3,5-triazin-2-yl)amino)-N-methylbenzamide | 423.2 | 0.65 |
| 49 | N-methyl-3-((4-(3-(3-methylphenoxy)-1-azetidinyl)-1,3,5-triazin-2-yl)amino)benzamide | 391 | 0.65 |
| 50 | 5-((4-(3-(4-chlorophenoxy)-1-azetidinyl)-1,3,5-triazin-2-yl)amino)-2-(dimethylamino)-N-methylbenzamide | 454.2 | 0.65 |
| 51 | 3-((4-(3-(2,4-dichlorophenoxy)-1-azetidinyl)-1,3,5-triazin-2-yl)amino)-N-methylbenzamide | 445 | 0.65 |
| 52 | N-methyl-3-((4-(4-(4-phenyl-1,3-thiazol-2-yl)-3,6-dihydro-1(2H)-pyridinyl)-1,3,5-triazin-2-yl)amino)benzamide | 470 | 0.66 |
| 53 | 3-((4-(4-(3,4-dimethylphenyl)-1-piperazinyl)-1,3,5-triazin-2-yl)amino)-N-methylbenzamide | 418 | 0.69 |
| 54 | 3-((4-(3-(2-chloro-4-fluorophenoxy)-1-azetidinyl)-1,3,5-triazin-2-yl)amino)-N-methylbenzamide | 429 | 0.72 |
| 55 | 3-((4-(3-(4-chloro-3-fluorophenoxy)-1-azetidinyl)-2-pyrimidinyl)amino)-N-methylbenzamide | 428 | 0.74 |
| 56 | 3-((6-(3-(4-fluorophenoxy)-1-azetidinyl)-2-pyridinyl)amino)-N-methylbenzamide | 393.2 | 0.75 |
| 57 | 2-fluoro-5-((4-(3-(4-fluorophenoxy)-1-azetidinyl)-1,3,5-triazin-2-yl)amino)-N-methylbenzamide | 413.1 | 0.76 |
| 58 | N-methyl-3-((4-(4-(4-(trifluoromethoxy)phenoxy)-1-piperidinyl)-1,3,5-triazin-2-yl)amino)benzamide | 489.2 | 0.76 |
| 59 | 3-((4-(3-(3,4-dichlorophenoxy)-1-azetidinyl)-2-pyrimidinyl)amino)-N-methylbenzamide | 444 | 0.78 |
| 60 | 3-((4-(4-(3-fluorophenyl)-1-piperazinyl)-1,3,5-triazin-2-yl)amino)-N-methylbenzamide | 408 | 0.79 |
| 61 | 3-((4-(3-(4-fluorophenoxy)-1-azetidinyl)-1,3,5-triazin-2-yl)amino)-N-methylbenzamide | 395 | 0.81 |
| 62 | N-methyl-3-((4-(3-(3-(trifluoromethyl)phenoxy)-1-azetidinyl)-1,3,5-triazin-2-yl)amino)benzamide | 445 | 0.82 |
| 63 | 3-((4-(3-(2,6-dichlorophenoxy)-1-azetidinyl)-1,3,5-triazin-2-yl)amino)-N-methylbenzamide | 445 | 0.82 |
| 64 | 2-fluoro-N-methyl-5-((4-((3-(4-(trifluoromethoxy)phenoxy)propyl)amino)-1,3,5-triazin-2-yl)amino)benzamide | 481 | 0.83 |
| 65 | N-methyl-3-((4-(4-phenyl-1-piperidinyl)-1,3,5-triazin-2-yl)amino)benzamide | 389.2 | 0.84 |
| 66 | 3-((4-(3-(2-chloro-5-methylphenoxy)-1-azetidinyl)-1,3,5-triazin-2-yl)amino)-N-methylbenzamide | 425 | 0.84 |
| 67 | N-methyl-3-((4-(3-((4-(trifluoromethoxy)phenoxy)methyl)-1-azetidinyl)-1,3,5-triazin-2-yl)amino)benzamide | 475 | 0.85 |
| 68 | 3-((4-(4-(3-fluoro-4-(trifluoromethoxy)phenoxy)-1-piperidinyl)-1,3,5-triazin-2-yl)amino)-N-methylbenzamide | 507.2 | 0.86 |
| 69 | 3-((4-(4-(3-chlorophenyl)-1-piperazinyl)-1,3,5-triazin-2-yl)amino)-N-methylbenzamide | 424 | 0.87 |

TABLE 1-continued

| Compound Number | Name | Mass Spec. | hNav1.7 IC$_{50}$ (μM) (AVG) |
|---|---|---|---|
| 70 | 5-((4-(3-((4-chlorophenoxy)methyl)-1-azetidinyl)-1,3,5-triazin-2-yl)amino)-2-fluoro-N-methylbenzamide | 443 | 0.89 |
| 71 | 3-((2-(3-(4-fluorophenoxy)-1-azetidinyl)-4-pyrimidinyl)amino)-N-methylbenzamide | 394.0 | 0.90 |
| 72 | 3-((4-(5-cyano-3,4-dihydro-2(1H)-isoquinolinyl)-1,3,5-triazin-2-yl)amino)-N-methylbenzamide | 386 | 0.90 |
| 73 | 3-((4-(3-((4-chloro-2-methylphenoxy)methyl)-1-azetidinyl)-1,3,5-triazin-2-yl)amino)-N-methylbenzamide | 439 | 0.90 |
| 74 | N-methyl-3-((4-(4-(4-(trifluoromethyl)phenyl)-1-piperazinyl)-1,3,5-triazin-2-yl)amino)benzamide | 458 | 0.96 |
| 75 | 2-chloro-N-methyl-5-((4-((3-(4-(trifluoromethoxy)phenoxy)propyl)amino)-1,3,5-triazin-2-yl)amino)benzamide | 497.2 | 0.96 |
| 76 | N-methyl-3-((4-(4-(6-methyl-2-pyridinyl)-1-piperazinyl)-1,3,5-triazin-2-yl)amino)benzamide | 405 | 0.97 |
| 77 | N-methyl-3-((4-(6-(3,3,3-trifluoropropoxy)-3,4-dihydro-2(1H)-isoquinolinyl)-1,3,5-triazin-2-yl)amino)benzamide | 473.2 | 0.98 |
| 78 | 3-((4-(3-(3-ethynylphenoxy)-1-azetidinyl)-1,3,5-triazin-2-yl)amino)-N-methylbenzamide | 401 | 0.99 |
| 79 | 2-chloro-5-((4-(3-(4-chloro-2-fluorophenoxy)-1-azetidinyl)-1,3,5-triazin-2-yl)amino)-N-methylbenzamide | 463 | 1.00 |
| 80 | 3-((4-(3-(3-methoxyphenoxy)-1-azetidinyl)-1,3,5-triazin-2-yl)amino)-N-methylbenzamide | 407 | 1.03 |
| 81 | 3-((4-(4-(2,3-dimethylphenyl)-1-piperazinyl)-1,3,5-triazin-2-yl)amino)-N-methylbenzamide | 418 | 1.03 |
| 82 | N-methyl-3-((4-(4-(4-(trifluoromethoxy)phenyl)-1-piperazinyl)-1,3,5-triazin-2-yl)amino)benzamide | 474.2 | 1.06 |
| 83 | N-methyl-3-((4-(3-(4-((trifluoromethyl)sulfanyl)phenoxy)-1-azetidinyl)-1,3,5-triazin-2-yl)amino)benzamide | 477 | 1.06 |
| 84 | 3-((4-(4-(4-chloro-3-fluorophenoxy)-1-piperidinyl)-1,3,5-triazin-2-yl)amino)-N-methylbenzamide | 457.2 | 1.08 |
| 85 | 3-((4-(4-(2-chlorophenoxy)-1-piperidinyl)-1,3,5-triazin-2-yl)amino)-N-methylbenzamide | 439.2 | 1.17 |
| 86 | 3-((4-(3-(3-fluorophenoxy)-1-azetidinyl)-1,3,5-triazin-2-yl)amino)-N-methylbenzamide | 395 | 1.20 |
| 87 | 3-((4-(3-(4-methoxyphenoxy)-1-azetidinyl)-1,3,5-triazin-2-yl)amino)-N-methylbenzamide | 407 | 1.23 |
| 88 | N-methyl-3-((4-(4-(phenylcarbonyl)-1-piperidinyl)-1,3,5-triazin-2-yl)amino)benzamide | 417 | 1.24 |
| 89 | N-methyl-3-((4-(4-(2-methylphenyl)-1-piperazinyl)-1,3,5-triazin-2-yl)amino)benzamide | 404 | 1.26 |
| 90 | 2-chloro-5-((4-(3-((4-chlorophenoxy)methyl)-1-azetidinyl)-1,3,5-triazin-2-yl)amino)-N-methylbenzamide | 459.2 | 1.26 |
| 91 | 3-((4-(3-((4-chloro-3-fluorophenoxy)methyl)-1-azetidinyl)-1,3,5-triazin-2-yl)amino)-N-methylbenzamide | 443.2 | 1.29 |
| 92 | 3-((4-(6-cyclopropyl-3,4-dihydro-2(1H)-isoquinolinyl)-1,3,5-triazin-2-yl)amino)-N-methylbenzamide | 401 | 1.29 |
| 93 | 3-((4-(4-((3,4-difluorophenoxy)methyl)-1-piperidinyl)-1,3,5-triazin-2-yl)amino)-N-methylbenzamide | 455.2 | 1.30 |
| 94 | N-methyl-3-((4-(3-((4-(trifluoromethoxy)benzyl)oxy)-1-azetidinyl)-1,3,5-triazin-2-yl)amino)benzamide | 475 | 1.32 |
| 95 | 3-((4-(4-(2-fluorophenyl)-1-piperazinyl)-1,3,5-triazin-2-yl)amino)-N-methylbenzamide | 408 | 1.35 |
| 96 | 2-chloro-N-methyl-5-((4-(3-((4-(trifluoromethyl)phenoxy)methyl)-1-azetidinyl)-1,3,5-triazin-2-yl)amino)benzamide | 493.2 | 1.39 |
| 97 | 2-chloro-5-((4-(3-(3-chloro-4-fluorophenoxy)-1-azetidinyl)-1,3,5-triazin-2-yl)amino)-N-methylbenzamide | 463 | 1.40 |
| 98 | 3-fluoro-5-((4-(3-(4-fluorophenoxy)-1-azetidinyl)-1,3,5-triazin-2-yl)amino)-N-methylbenzamide | 413 | 1.41 |
| 99 | 3-((4-(4-(4-cyanophenyl)-3,6-dihydro-1(2H)-pyridinyl)-1,3,5-triazin-2-yl)amino)-N-methylbenzamide | 412 | 1.43 |
| 100 | mixture of N-methyl-3-((4-(((1R)-1-methyl-3-phenylpropyl)amino)-1,3,5-triazin-2-yl)amino)benzamide and N-methyl-3-((4-(((1S)-1-methyl-3-phenylpropyl)amino)-1,3,5-triazin-2-yl)amino)benzamide | 377.2 | 1.44 |
| 101 | N-methyl-3-((4-(4-(4-(2,2,2-trifluoroethoxy)phenyl)-1-piperidinyl)-1,3,5-triazin-2-yl)amino)benzamide | 503.2 | 1.44 |
| 102 | N-ethyl-3-((4-(3-(4-fluorophenoxy)-1-azetidinyl)-1,3,5-triazin-2-yl)amino)benzamide | 409.2 | 1.51 |
| 103 | 3-fluoro-N-methyl-5-((4-(4-(4-phenyl-1,3-thiazol-2-yl)-1-piperazinyl)-1,3,5-triazin-2-yl)amino)benzamide | 490.2 | 1.56 |
| 104 | 3-((4-(3-(2,3-dichlorophenoxy)-1-azetidinyl)-1,3,5-triazin-2-yl)amino)-N-methylbenzamide | 445 | 1.57 |
| 105 | 3-((4-(3-((4-chloro-2-fluorophenoxy)methyl)-1-azetidinyl)-1,3,5-triazin-2-yl)amino)-N-methylbenzamide | 443 | 1.58 |
| 106 | 3-((4-(3-(3,4-difluorophenoxy)-1-azetidinyl)-2-pyrimidinyl)amino)-N-methylbenzamide | 412 | 1.60 |
| 107 | 3-((4-(4-(3-chloro-5-(trifluoromethyl)-2-pyridinyl)-1,4-diazepan-1-yl)-1,3,5-triazin-2-yl)amino)-N-methylbenzamide | 507.2 | 1.61 |
| 108 | 3-((4-(4-(5-chloro-2-pyridinyl)-1-piperazinyl)-1,3,5-triazin-2-yl)amino)-N-methylbenzamide | 425 | 1.61 |
| 109 | N-methyl-3-((4-(4-(2-phenylethyl)-1-piperazinyl)-1,3,5-triazin-2-yl)amino)benzamide | 418 | 1.63 |
| 110 | N-methyl-3-((4-(6-(trifluoromethoxy)-3,4-dihydro-2(1H)-isoquinolinyl)-1,3,5-triazin-2-yl)amino)benzamide | 445.2 | 1.67 |
| 111 | N-methyl-3-((4-(3-(3-(trifluoromethoxy)phenoxy)-1-azetidinyl)-1,3,5-triazin-2-yl)amino)benzamide | 461.2 | 1.69 |
| 112 | 3-fluoro-N-methyl-5-((4-(3-((4-(trifluoromethyl)phenoxy)methyl)-1-azetidinyl)-1,3,5-triazin-2-yl)amino)benzamide | 477.2 | 1.78 |
| 113 | 3-((4-(3-((4-chlorobenzyl)oxy)-1-azetidinyl)-1,3,5-triazin-2-yl)amino)-N-methylbenzamide | 425 | 1.82 |
| 114 | N-methyl-3-((4-(4-(3-methylphenyl)-1-piperazinyl)-1,3,5-triazin-2-yl)amino)benzamide | 404 | 1.83 |
| 115 | N-methyl-3-((4-(4-phenyl-1-piperazinyl)-1,3,5-triazin-2-yl)amino)benzamide | 390 | 1.87 |
| 116 | 3-fluoro-N-methyl-5-((4-(4-(6-methyl-2-pyridinyl)-1-piperazinyl)-1,3,5-triazin-2-yl)amino)benzamide | 423 | 2.00 |
| 117 | 3-((4-(4-(3,4-dimethylphenyl)-1-piperidinyl)-1,3,5-triazin-2-yl)amino)-N-methylbenzamide | 417 | 2.00 |
| 118 | N-methyl-3-((4-(4-(4-(trifluoromethyl)phenoxy)-1-piperidinyl)-1,3,5-triazin-2-yl)amino)benzamide | 473.2 | 2.02 |

TABLE 1-continued

| Compound Number | Name | Mass Spec. | hNav1.7 IC$_{50}$ (μM) (AVG) |
|---|---|---|---|
| 119 | N-methyl-3-((4-(4-(3-(trifluoromethoxy)phenoxy)-1-piperidinyl)-1,3,5-triazin-2-yl)amino)benzamide | 489.2 | 2.07 |
| 120 | N-methyl-3-((4-(((1R)-1-methyl-3-phenylpropyl)amino)-1,3,5-triazin-2-yl)amino)benzamide | 447.2 | 2.09 |
| 121 | 3-((4-(3-(3-chloro-4-fluorophenoxy)-1-azetidinyl)-1,3,5-triazin-2-yl)amino)-5-fluoro-N-methylbenzamide | 447.2 | 2.09 |
| 122 | 3-((4-(4-(3-chlorophenoxy)-1-piperidinyl)-1,3,5-triazin-2-yl)amino)-N-methylbenzamide | 439.2 | 2.10 |
| 123 | N-methyl-3-((4-(5-(trifluoromethoxy)-3,4-dihydro-2(1H)-isoquinolinyl)-1,3,5-triazin-2-yl)amino)benzamide | 445.2 | 2.13 |
| 124 | N-methyl-3-((4-(4-(phenylethynyl)-1-piperidinyl)-1,3,5-triazin-2-yl)amino)benzamide | 413.1 | 2.16 |
| 125 | 3-((4-(3-(2,4-difluorophenoxy)-1-azetidinyl)-2-pyrimidinyl)amino)-N-methylbenzamide | 412 | 2.16 |
| 126 | N-methyl-3-((4-(4-((4-(trifluoromethoxy)phenyl)sulfonyl)-1-piperazinyl)-1,3,5-triazin-2-yl)amino)benzamide | 538.2 | 2.29 |
| 127 | 3-((4-(5-ethyl-1,3,4,5-tetrahydro-2H-pyrido[4,3-b]indol-2-yl)-1,3,5-triazin-2-yl)amino)-N-methylbenzamide | 428 | 2.31 |
| 128 | 3-((4-(3-(3-chloro-4-cyanophenoxy)-1-azetidinyl)-1,3,5-triazin-2-yl)amino)-N-methylbenzamide | 436 | 2.31 |
| 129 | 4-chloro-3-((4-(3-(4-fluorophenoxy)-1-azetidinyl)-1,3,5-triazin-2-yl)amino)-N-methylbenzamide | 429 | 2.37 |
| 130 | 3-((4-(6-chloro-3,4-dihydro-2(1H)-isoquinolinyl)-1,3,5-triazin-2-yl)amino)-N-methylbenzamide | 395 | 2.44 |
| 131 | N-methyl-3-((4-(4-((4-(trifluoromethoxy)benzyl)oxy)-1-piperidinyl)-1,3,5-triazin-2-yl)amino)benzamide | 503.2 | 2.49 |
| 132 | 3-((4-(3-((2,4-dichlorophenoxy)methyl)-1-azetidinyl)-1,3,5-triazin-2-yl)amino)-N-methylbenzamide | 461 | 2.55 |
| 133 | 3-((4-(4-(3,4-dimethylphenyl)-3,6-dihydro-1(2H)-pyridinyl)-1,3,5-triazin-2-yl)amino)-N-methylbenzamide | 415 | 2.55 |
| 134 | 3-((4-(3-(3-tert-butylphenoxy)-1-azetidinyl)-1,3,5-triazin-2-yl)amino)-N-methylbenzamide | 433 | 2.58 |
| 135 | N-methyl-3-((4-(4-(4-(trifluoromethoxy)phenyl)-1-piperidinyl)-1,3,5-triazin-2-yl)amino)benzamide | 473.2 | 2.59 |
| 136 | N-methyl-3-((4-(4-(4-(trifluoromethoxy)phenyl)-3,6-dihydro-1(2H)-pyridinyl)-1,3,5-triazin-2-yl)amino)benzamide | 471.2 | 2.72 |
| 137 | N-methyl-3-((4-(5-(2,2,2-trifluoroethoxy)-3,4-dihydro-2(1H)-isoquinolinyl)-1,3,5-triazin-2-yl)amino)benzamide | 459 | 2.73 |
| 138 | 3-((4-(5-methoxy-3,4-dihydro-2(1H)-isoquinolinyl)-1,3,5-triazin-2-yl)amino)-N-methylbenzamide | 391.2 | 2.74 |
| 139 | N-methyl-3-((4-(4-(4-phenyl-1H-pyrazol-1-yl)-1-piperidinyl)-1,3,5-triazin-2-yl)amino)benzamide | 455.2 | 2.74 |
| 140 | N-methyl-3-((4-(4-(3-phenyl-1,2,4-oxadiazol-5-yl)-1-piperidinyl)-1,3,5-triazin-2-yl)amino)benzamide | 457.2 | 2.79 |
| 141 | N-methyl-3-((4-(3-(2-(trifluoromethyl)phenoxy)-1-azetidinyl)-1,3,5-triazin-2-yl)amino)benzamide | 445 | 2.79 |
| 142 | 3-((4-(5-chloro-3,4-dihydro-2(1H)-isoquinolinyl)-1,3,5-triazin-2-yl)amino)-N-methylbenzamide | 395 | 2.80 |
| 143 | N-methyl-3-((4-(4-(phenoxymethyl)-1-piperidinyl)-1,3,5-triazin-2-yl)amino)benzamide | 419.2 | 2.80 |
| 144 | 3-((4-(1-(4-chlorophenyl)-1,4,6,7-tetrahydro-5H-pyrazolo[4,3-c]pyridin-5-yl)-1,3,5-triazin-2-yl)amino)-N-methylbenzamide | 461 | 2.87 |
| 145 | 3-((4-(4-(4-chlorophenoxy)-1-piperidinyl)-1,3,5-triazin-2-yl)amino)-N-methylbenzamide | 439.2 | 2.90 |
| 146 | 3-fluoro-N-methyl-5-((4-(4-(4-(trifluoromethoxy)phenoxy)-1-piperidinyl)-1,3,5-triazin-2-yl)amino)benzamide | 507 | 2.91 |
| 147 | 3-((4-(4-(4-chlorophenyl)-4-cyano-1-piperidinyl)-1,3,5-triazin-2-yl)amino)-N-methylbenzamide | 448 | 2.92 |
| 148 | 3-((4-(3-(2,4-difluorophenoxy)-1-azetidinyl)-1,3,5-triazin-2-yl)amino)-N-methylbenzamide | 413 | 2.95 |
| 149 | 3-((4-(3-(4-tert-butylphenoxy)-1-azetidinyl)-1,3,5-triazin-2-yl)amino)-N-methylbenzamide | 433 | 2.99 |
| 150 | N-methyl-3-((4-(4-((4-(trifluoromethyl)benzyl)oxy)-1-piperidinyl)-1,3,5-triazin-2-yl)amino)benzamide | 487.2 | 3.03 |
| 151 | 3-((4-(4-(3,4-difluorobenzyl)-1-piperidinyl)-1,3,5-triazin-2-yl)amino)-N-methylbenzamide | 439.2 | 3.10 |
| 152 | 3-((4-(3-(4-chlorophenoxy)propyl)amino)-1,3,5-triazin-2-yl)amino)-N-methylbenzamide | 413.2 | 3.10 |
| 153 | 3-((4-(3-(4-chloro-2,6-difluorophenoxy)-1-azetidinyl)-1,3,5-triazin-2-yl)amino)-N-methylbenzamide | 447 | 3.16 |
| 154 | mixture of N-methyl-3-((4-((3S)-3-(4-(trifluoromethoxy)phenoxy)-1-pyrrolidinyl)-1,3,5-triazin-2-yl)amino)benzamide and N-methyl-3-((4-((3R)-3-(4-(trifluoromethoxy)phenoxy)-1-pyrrolidinyl)-1,3,5-triazin-2-yl)amino)benzamide | 475 | 3.17 |
| 155 | 3-((4-(3-(2-fluoro-5-methylphenoxy)-1-azetidinyl)-1,3,5-triazin-2-yl)amino)-N-methylbenzamide | 409 | 3.17 |
| 156 | N,2-dimethyl-3-((4-((3-(4-(trifluoromethoxy)phenoxy)propyl)amino)-1,3,5-triazin-2-yl)amino)benzamide | 477 | 3.34 |
| 157 | 3-((4-(4-(4-chlorophenyl)-1-piperazinyl)-1,3,5-triazin-2-yl)amino)-N-methylbenzamide | 424 | 3.36 |
| 158 | 3-((4-(3-((3,4-dichlorophenoxy)methyl)-1-azetidinyl)-1,3,5-triazin-2-yl)amino)-N-methylbenzamide | 461.2 | 3.50 |
| 159 | 3-((4-(4-(4-methoxyphenyl)-1-piperazinyl)-1,3,5-triazin-2-yl)amino)-N-methylbenzamide | 420 | 3.50 |
| 160 | 3-((4-(3-(4-fluorophenoxy)-1-azetidinyl)-1,3,5-triazin-2-yl)amino)-N,4-dimethylbenzamide | 409.2 | 3.65 |
| 161 | 3-((4-(3-((4-chlorophenoxy)methyl)-1-azetidinyl)-1,3,5-triazin-2-yl)amino)-2,6-difluoro-N-methylbenzamide | 461.2 | 3.67 |
| 162 | 2-chloro-5-((4-(3-(4-chlorophenoxy)-1-azetidinyl)-1,3,5-triazin-2-yl)amino)-N-methylbenzamide | 445 | 3.69 |
| 163 | 3-((4-(3-((4-fluorophenoxy)methyl)-1-azetidinyl)-1,3,5-triazin-2-yl)amino)-N-methylbenzamide | 409.2 | 3.71 |
| 164 | 2-chloro-N-methyl-5-((4-((3-(3-(trifluoromethyl)phenoxy)propyl)amino)-1,3,5-triazin-2-yl)amino)benzamide | 481 | 3.75 |
| 165 | 4-fluoro-3-((4-(3-(4-fluorophenoxy)-1-azetidinyl)-1,3,5-triazin-2-yl)amino)-N-methylbenzamide | 413 | 3.82 |
| 166 | 3-((4-(4-(4-chloro-3-(trifluoromethoxy)phenoxy)-1-piperidinyl)- | 523.2 | 4.05 |

TABLE 1-continued

| Compound Number | Name | Mass Spec. | hNav1.7 IC$_{50}$ (μM) (AVG) |
|---|---|---|---|
| | 1,3,5-triazin-2-yl)amino)-N-methylbenzamide | | |
| 167 | 3-((4-(4-(4-chlorophenyl)-1H-pyrazol-1-yl)-1-piperidinyl)-1,3,5-triazin-2-yl)amino)-N-methylbenzamide | 489 | 4.16 |
| 168 | N-methyl-3-((4-(4-(5-methyl-4-phenyl-1,3-thiazol-2-yl)-1-piperidinyl)-1,3,5-triazin-2-yl)amino)benzamide | 486.2 | 4.22 |
| 169 | N-methyl-3-((4-((3-(4-(trifluoromethyl)phenoxy)propyl)amino)-1,3,5-triazin-2-yl)amino)benzamide | 447.2 | 4.25 |
| 170 | 3-((4-(4-(4-cyanophenyl)-1-piperidinyl)-1,3,5-triazin-2-yl)amino)-N-methylbenzamide | 414.2 | 4.30 |
| 171 | N-methyl-3-((4-(3-((3-(trifluoromethoxy)phenoxy)methyl)-1-azetidinyl)-1,3,5-triazin-2-yl)amino)benzamide | 475 | 4.33 |
| 172 | N-methyl-3-((4-(4-(2-(trifluoromethoxy)phenyl)-1-piperazinyl)-1,3,5-triazin-2-yl)amino)benzamide | 474 | 4.45 |
| 173 | 3-((4-(3-((4-chlorophenoxy)methyl)-1-azetidinyl)-1,3,5-triazin-2-yl)amino)-5-fluoro-N-methylbenzamide | 443.2 | 4.56 |
| 174 | 3-((4-(3-(4-fluorophenoxy)-1-azetidinyl)-1,3,5-triazin-2-yl)amino)-N-(2,2,2-trifluoroethyl)benzamide | 463.2 | 4.62 |
| 175 | N-methyl-3-((4-(4-(2-pyridinyloxy)-1-piperidinyl)-1,3,5-triazin-2-yl)amino)benzamide | 406 | 4.63 |
| 176 | 3-((4-(6-fluoro-3,4-dihydro-2(1H)-isoquinolinyl)-1,3,5-triazin-2-yl)amino)-N-methylbenzamide | 379.2 | 4.67 |
| 177 | 3-((4-(3-(2,5-difluorophenoxy)-1-azetidinyl)-1,3,5-triazin-2-yl)amino)-N-methylbenzamide | 413 | 4.72 |
| 178 | N-methyl-3-((4-(4-(2-(trifluoromethyl)phenyl)-1-piperazinyl)-1,3,5-triazin-2-yl)amino)benzamide | 458 | 4.78 |
| 179 | 3-((4-(3-(4-fluorophenoxy)-1-azetidinyl)-2-pyridinyl)amino)-N-methylbenzamide | 393.2 | 4.84 |
| 180 | N-methyl-3-((4-(4-(4-(trifluoromethoxy)benzyl)-1-piperazinyl)-1,3,5-triazin-2-yl)amino)benzamide | 488.2 | 4.85 |
| 181 | N-methyl-3-((4-(3-(2-(trifluoromethoxy)phenoxy)-1-azetidinyl)-1,3,5-triazin-2-yl)amino)benzamide | 461.2 | 4.93 |
| 182 | N-methyl-3-((4-(3-methyl-3-(4-methylphenoxy)-1-azetidinyl)-1,3,5-triazin-2-yl)amino)benzamide | 405.2 | 5.10 |
| 183 | 3-((4-(3-(4-chlorophenoxy)-1-azetidinyl)-1,3,5-triazin-2-yl)amino)-2,6-difluoro-N-methylbenzamide | 447 | 5.19 |
| 184 | 3-((4-(3-(4-chlorophenyl)-1-azetidinyl)-1,3,5-triazin-2-yl)amino)-N-methylbenzamide | 395 | 5.23 |
| 185 | N-methyl-3-((4-(6-methyl-3,4-dihydro-2(1H)-isoquinolinyl)-1,3,5-triazin-2-yl)amino)benzamide | 375.2 | 5.28 |
| 186 | mixture of 3-((4-(3-((1R)-1-(4-chlorophenoxy)ethyl)-1-azetidinyl)-1,3,5-triazin-2-yl)amino)-N-methylbenzamide and 3-((4-(3-((1S)-1-(4-chlorophenoxy)ethyl)-1-azetidinyl)-1,3,5-triazin-2-yl)amino)-N-methylbenzamide | 439 | 5.34 |
| 187 | 3-((4-(3-(3,5-difluorophenoxy)-1-azetidinyl)-1,3,5-triazin-2-yl)amino)-N-methylbenzamide | 413 | 5.43 |
| 188 | N-methyl-3-((4-(3-((3-(trifluoromethoxy)phenoxy)methyl)-1-azetidinyl)-1,3,5-triazin-2-yl)amino)benzamide | 459 | 5.44 |
| 189 | N-methyl-3-((4-(3-(((4-(trifluoromethyl)benzyl)oxy)methyl)-1-azetidinyl)-1,3,5-triazin-2-yl)amino)benzamide | 473 | 5.56 |
| 190 | 3-((4-(4-(4-(2-chlorophenyl)-1H-pyrazol-1-yl)-1-piperidinyl)-1,3,5-triazin-2-yl)amino)-N-methylbenzamide | 489 | 5.58 |
| 191 | N-methyl-3-((4-(4-(2-(trifluoromethoxy)benzyl)-1-piperazinyl)-1,3,5-triazin-2-yl)amino)benzamide | 488 | 5.60 |
| 192 | 3-((4-(3-(2-fluorophenoxy)-1-azetidinyl)-1,3,5-triazin-2-yl)amino)-N-methylbenzamide | 395 | 5.60 |
| 193 | 3-((4-(4-(4-fluoro-3-(trifluoromethoxy)phenoxy)-1-piperidinyl)-1,3,5-triazin-2-yl)amino)-N-methylbenzamide | 507.2 | 5.79 |
| 194 | 3-((4-(3-(2-chloro-4-(trifluoromethoxy)phenoxy)-1-azetidinyl)-1,3,5-triazin-2-yl)amino)-N-methylbenzamide | 479 | 5.97 |
| 195 | 3-((4-(4-(4-cyanophenyl)-1-piperazinyl)-1,3,5-triazin-2-yl)amino)-N-methylbenzamide | 415 | 6.03 |
| 196 | 3-((4-(4-(4-fluorobenzyl)-1-piperidinyl)-1,3,5-triazin-2-yl)amino)-N-methylbenzamide | 421.2 | 6.40 |
| 197 | 3-((2-(3-((4-chlorophenoxy)methyl)-1-azetidinyl)-4-pyrimidinyl)amino)-N-methylbenzamide | 424.0 | 6.80 |
| 198 | 3-((4-(4-(4-fluorophenyl)-1-piperazinyl)-1,3,5-triazin-2-yl)amino)-N-methylbenzamide | 408 | 6.83 |
| 199 | 3-((4-(3-(3-biphenylyloxy)-1-azetidinyl)-1,3,5-triazin-2-yl)amino)-N-methylbenzamide | 453 | 7.02 |
| 200 | 3-((4-(4-((4-(trifluoromethoxy)benzyl)oxy)-1-piperidinyl)-1,3,5-triazin-2-yl)amino)benzamide | 489.2 | 7.03 |
| 201 | 3-((4-(3-((3-chlorophenoxy)methyl)-1-azetidinyl)-1,3,5-triazin-2-yl)amino)benzamide | 425 | 7.03 |
| 202 | N,2-dimethyl-3-((4-(4-(4-(trifluoromethoxy)phenyl)-1-piperazinyl)-1,3,5-triazin-2-yl)amino)benzamide | 488 | 7.12 |
| 203 | 3-((4-(4-benzyl-1,4-diazepan-1-yl)-1,3,5-triazin-2-yl)amino)-N-methylbenzamide | 418.2 | 7.42 |
| 204 | 3-((4-(3-(2-methoxyphenoxy)-1-azetidinyl)-1,3,5-triazin-2-yl)amino)-N-methylbenzamide | 407 | 7.42 |
| 205 | N-cyclopropyl-3-((4-(3-(4-fluorophenoxy)-1-azetidinyl)-1,3,5-triazin-2-yl)amino)benzamide | 421.2 | 7.42 |
| 206 | 3-((4-(4-(benzyloxy)-1-piperidinyl)-1,3,5-triazin-2-yl)amino)-N-methylbenzamide | 419 | 7.93 |
| 207 | 3-((4-(3-(4-(cyanomethyl)phenoxy)-1-azetidinyl)-1,3,5-triazin-2-yl)amino)-N-methylbenzamide | 416 | 7.98 |
| 208 | 3-((4-(3-((4-chloro-3-(trifluoromethyl)phenoxy)methyl)-1-azetidinyl)-1,3,5-triazin-2-yl)amino)-N-methylbenzamide | 493 | 8.11 |
| 209 | N-methyl-3-((4-(4-(2-(trifluoromethoxy)phenoxy)-1-piperidinyl)-1,3,5-triazin-2-yl)amino)benzamide | 489.2 | 8.15 |
| 210 | 3-((4-(3-(4-cyanophenoxy)-1-azetidinyl)-1,3,5-triazin-2-yl)amino)-N-methylbenzamide | 402.2 | 8.24 |
| 211 | 3-((4-(2-((4-chlorophenoxy)methyl)-1-azetidinyl)-1,3,5-triazin-2-yl)amino)-N-methylbenzamide | 425 | 8.30 |
| 212 | 3-((4-(3-(2-chlorophenoxy)-1-piperidinyl)-1,3,5-triazin-2-yl)amino)-N-methylbenzamide | 439 | 8.31 |
| 213 | N-tert-butyl-3-((4-(3-(4-fluorophenoxy)-1-azetidinyl)-1,3,5-triazin-2-yl)amino)benzamide | 437.2 | 8.39 |

TABLE 1-continued

| Compound Number | Name | Mass Spec. | hNav1.7 IC$_{50}$ (μM) (AVG) |
|---|---|---|---|
| 214 | 3-((4-(3-(4-(benzyloxy)phenoxy)-1-azetidinyl)-1,3,5-triazin-2-yl)amino)-N-methylbenzamide | 483 | 8.47 |
| 215 | 3-((4-(4-(4-cyano-3-(trifluoromethyl)phenyl)-1-piperidinyl)-1,3,5-triazin-2-yl)amino)-N-methylbenzamide | 425 | 8.59 |
| 216 | N-methyl-3-((4-(6-(trifluoromethyl)-3,4-dihydro-2(1H)-isoquinolinyl)-1,3,5-triazin-2-yl)amino)benzamide | 429.2 | 8.60 |
| 217 | 3-((4-(3-(2-biphenylyloxy)-1-azetidinyl)-1,3,5-triazin-2-yl)amino)-N-methylbenzamide | 453 | 8.66 |
| 218 | 3-((6-(3-(4-fluorophenoxy)-1-azetidinyl)-4-pyrimidinyl)amino)-N-methylbenzamide | 394.2 | 8.68 |
| 219 | 5-((4-(3-(4-chlorophenoxy)-1-azetidinyl)-1,3,5-triazin-2-yl)amino)-2-hydroxy-N-methylbenzamide | 427.2 | 8.82 |
| 220 | 3-((4-(7-methoxy-3,4-dihydro-2(1H)-isoquinolinyl)-1,3,5-triazin-2-yl)amino)-N-methylbenzamide | 391.2 | 8.85 |
| 221 | 3-((4-(6-bromo-3,4-dihydro-2(1H)-isoquinolinyl)-1,3,5-triazin-2-yl)amino)benzamide | 427.3 | 8.90 |
| 222 | 3-((4-(6-methoxy-3,4-dihydro-2(1H)-isoquinolinyl)-1,3,5-triazin-2-yl)amino)-N-methylbenzamide | 391.2 | 8.96 |
| 223 | 3-((4-(3-((4-methoxyphenoxy)methyl)-1-azetidinyl)-1,3,5-triazin-2-yl)amino)-N-methylbenzamide | 421 | 9.19 |
| 224 | 3-((4-(3-(3,5-dichlorophenoxy)-1-azetidinyl)-1,3,5-triazin-2-yl)amino)-N-methylbenzamide | 445 | 9.29 |
| 225 | 3-((4-(5-fluoro-3,4-dihydro-2(1H)-isoquinolinyl)-1,3,5-triazin-2-yl)amino)-N-methylbenzamide | 379 | 9.31 |
| 226 | N-methyl-3-((4-(3-(2,3,4-trifluorophenoxy)-1-azetidinyl)-1,3,5-triazin-2-yl)amino)benzamide | 431 | 9.35 |
| 227 | 2-chloro-5-((4-(4-(3,4-dimethylphenyl)-1-piperazinyl)-1,3,5-triazin-2-yl)amino)-N-methylbenzamide | 438 | 9.36 |
| 228 | 3-((4-(4-((3,4-difluorobenzyl)oxy)-1-piperidinyl)-1,3,5-triazin-2-yl)amino)-N-methylbenzamide | 455.2 | 9.42 |
| 229 | N-methyl-3-((4-(3-((2-(trifluoromethoxy)phenoxy)methyl)-1-azetidinyl)-1,3,5-triazin-2-yl)amino)benzamide | 475 | 9.44 |
| 230 | 3-((4-(4-benzyl-1-piperidinyl)-1,3,5-triazin-2-yl)amino)-N-methylbenzamide | 403 | 9.50 |
| 231 | N-methyl-3-((4-(4-(3-(1-methylethyl)-1,2,4-oxadiazol-5-yl)-1-piperidinyl)-1,3,5-triazin-2-yl)amino)benzamide | 423 | 9.66 |
| 232 | 3-((4-((3-(4-chlorophenyl)propyl)amino)-1,3,5-triazin-2-yl)amino)-N-methylbenzamide | 397.15 | 9.84 |
| 233 | 3-((4-(6-(2-methoxyethoxy)-3,4-dihydro-2(1H)-isoquinolinyl)-1,3,5-triazin-2-yl)amino)-N-methylbenzamide | 435.2 | 9.87 |
| 234 | N-methyl-3-((4-(3-((2-naphthalenyloxy)methyl)-1-azetidinyl)-1,3,5-triazin-2-yl)amino)benzamide | 441 | 10.04 |
| 235 | 3-((4-(3,4-dihydro-2(1H)-isoquinolinyl)-1,3,5-triazin-2-yl)amino)benzamide | 347.2 | 10.26 |
| 236 | 3-((4-((2-(4-chlorophenoxy)ethyl)amino)-1,3,5-triazin-2-yl)amino)-N-methylbenzamide | 399.2 | 10.36 |
| 237 | 3-((4-(3-(4-fluorophenoxy)-1-azetidinyl)-1,3,5-triazin-2-yl)amino)-N-methylbenzamide | 381.3 | 10.70 |
| 238 | 3-((4-(4-(2-fluorophenoxy)-1-piperidinyl)-1,3,5-triazin-2-yl)amino)-N-methylbenzamide | 423.2 | 10.80 |
| 239 | N-methyl-3-((4-(4-((3-(trifluoromethyl)benzyl)oxy)-1-piperidinyl)-1,3,5-triazin-2-yl)amino)benzamide | 487.2 | 10.82 |
| 240 | N,N-dimethyl-3-((4-(4-((4-(trifluoromethoxy)benzyl)oxy)-1-piperidinyl)-1,3,5-triazin-2-yl)amino)benzamide | 517.2 | 11.06 |
| 241 | 3-((4-(3-(((4-chlorobenzyl)oxy)methyl)-1-azetidinyl)-1,3,5-triazin-2-yl)amino)-N-methylbenzamide | 439 | 11.09 |
| 242 | 3-((4-(3-((3-fluorophenoxy)methyl)-1-azetidinyl)-1,3,5-triazin-2-yl)amino)-N-methylbenzamide | 409 | 11.25 |
| 243 | 3-((4-(3,4-dihydro-2(1H)-isoquinolinyl)-1,3,5-triazin-2-yl)amino)-N-methylbenzamide | 361 | 11.50 |
| 244 | 3-((4-(3-((3-methoxyphenoxy)methyl)-1-azetidinyl)-1,3,5-triazin-2-yl)amino)-N-methylbenzamide | 421 | 11.98 |
| 245 | 3-((4-(4-cyano-4-(4-fluorophenyl)-1-piperidinyl)-1,3,5-triazin-2-yl)amino)-N-methylbenzamide | 432 | 12.54 |
| 246 | N-methyl-3-((4-(4-(3-propyl-1,2,4-oxadiazol-5-yl)-1-piperidinyl)-1,3,5-triazin-2-yl)amino)benzamide | 423 | 12.66 |
| 247 | 3-((4-(3-((2-chlorophenoxy)methyl)-1-azetidinyl)-1,3,5-triazin-2-yl)amino)-N-methylbenzamide | 425 | 12.76 |
| 248 | 3-((4-(4-(4-cyano-3-(trifluoromethoxy)phenyl)-1-piperidinyl)-1,3,5-triazin-2-yl)amino)-N-methylbenzamide | 498 | 12.90 |
| 249 | 3-((4-(4-(4-chlorophenyl)-1-piperidinyl)-1,3,5-triazin-2-yl)amino)-N-methylbenzamide | 423.2 | 13.08 |
| 250 | N-methyl-3-((4-(4-((4-methylphenyl)sulfanyl)-1-piperidinyl)-1,3,5-triazin-2-yl)amino)benzamide | 435 | 13.10 |
| 251 | 3-((4-(3-((2-fluorophenoxy)methyl)-1-piperidinyl)-1,3,5-triazin-2-yl)amino)-N-methylbenzamide | 409 | 13.76 |
| 252 | 3-((4-(5-(2-methoxyethoxy)-3,4-dihydro-2(1H)-isoquinolinyl)-1,3,5-triazin-2-yl)amino)-N-methylbenzamide | 435.2 | 14.99 |
| 253 | N-methyl-3-((4-(3-((1-naphthalenyloxy)methyl)-1-azetidinyl)-1,3,5-triazin-2-yl)amino)benzamide | 441 | 15.20 |
| 254 | N-methyl-3-((4-(((3-phenyl-1,2,4-oxadiazol-5-yl)methyl)amino)-1,3,5-triazin-2-yl)amino)benzamide | 403.2 | 15.72 |
| 255 | 3-((4-(3-(((5-chloro-8-quinolinyl)oxy)methyl)-1-azetidinyl)-1,3,5-triazin-2-yl)amino)-N-methylbenzamide | 476.2 | 15.97 |
| 256 | 3-((4-(3-(2-fluoro-3-(trifluoromethyl)phenoxy)-1-azetidinyl)-1,3,5-triazin-2-yl)amino)-N-methylbenzamide | 463 | 16.73 |
| 257 | N-methyl-3-((4-(4-(phenylamino)-1-piperidinyl)-1,3,5-triazin-2-yl)amino)benzamide | 404 | 16.87 |
| 258 | 3-((4-(3-((4-cyanophenoxy)methyl)-1-azetidinyl)-1,3,5-triazin-2-yl)amino)-N-methylbenzamide | 416 | 16.89 |
| 259 | N-methyl-3-((4-(1'H,3H-spiro[2-benzofuran-1,4'-piperidin]-1'-yl)-1,3,5-triazin-2-yl)amino)benzamide | 417 | 17.07 |
| 260 | 3-((4-((3-(3-fluorophenoxy)propyl)amino)-1,3,5-triazin-2-yl)amino)-N-methylbenzamide | 397.2 | 17.61 |
| 261 | 3-((4-(4-((cyclopropylmethoxy)methyl)-1-piperidinyl)-1,3,5-triazin-2-yl)amino)-N-methylbenzamide | 497 | 17.67 |
| 262 | 3-chloro-5-((4-(3-(4-fluorophenoxy)-1-azetidinyl)-1,3,5-triazin-2-yl)amino)-N-methylbenzamide | 429 | 17.80 |
| 263 | N-methyl-3-((4-(3-methyl-3-phenoxy-1-azetidinyl)-1,3,5-triazin-2-yl)amino)benzamide | 391.2 | 18.10 |

TABLE 1-continued

| Compound Number | Name | Mass Spec. | hNav1.7 IC$_{50}$ (μM) (AVG) |
|---|---|---|---|
| 264 | 3-((4-(3-(4-cyclopentylphenoxy)-1-azetidinyl)-1,3,5-triazin-2-yl)amino)-N-methylbenzamide | 445 | 18.89 |
| 265 | N-methyl-3-((4-(2-phenyl-6,7-dihydrofuro[3,2-c]pyridin-5(4H)-yl)-1,3,5-triazin-2-yl)amino)benzamide | 427.2 | 19.23 |
| 266 | 5-((4-(3-(4-fluorophenoxy)-1-azetidinyl)-1,3,5-triazin-2-yl)amino)-N,2-dimethylbenzamide | 409.2 | 19.66 |
| 267 | 2-methyl-3-((4-(4-((4-(trifluoromethoxy)benzyl)oxy)-1-piperidinyl)-1,3,5-triazin-2-yl)amino)benzamide | 503.2 | 20.90 |
| 268 | N-methyl-3-((4-(1-phenyl-1,4,6,7-tetrahydro-5H-pyrazolo[4,3-c]pyridin-5-yl)-1,3,5-triazin-2-yl)amino)benzamide | 427 | 20.95 |
| 269 | N-methyl-3-((4-(8-(trifluoromethyl)-3,4-dihydro-2(1H)-isoquinolinyl)-1,3,5-triazin-2-yl)amino)benzamide | 429.2 | 20.98 |
| 270 | 2-fluoro-3-((4-(3-(4-fluorophenoxy)-1-azetidinyl)-1,3,5-triazin-2-yl)amino)-N-methylbenzamide | 413.1 | 21.13 |
| 271 | 3-((4-(4-(3-chloro-4-fluorophenyl)-1-piperazinyl)-1,3,5-triazin-2-yl)amino)-N-methylbenzamide | 442.2 | 21.38 |
| 272 | 3-((4-(3-((4-fluorobenzyl)oxy)-1-azetidinyl)-1,3,5-triazin-2-yl)amino)-N-methylbenzamide | 409 | 21.74 |
| 273 | N-methyl-3-((4-(3-methyl-3-(phenoxymethyl)-1-azetidinyl)-1,3,5-triazin-2-yl)amino)benzamide | 405.2 | 22.09 |
| 274 | 3-((4-(3-(2,6-difluorophenoxy)-1-azetidinyl)-1,3,5-triazin-2-yl)amino)-N-methylbenzamide | 413 | 22.09 |
| 275 | N,2-dimethyl-3-((4-(6-(2,2,2-trifluoroethoxy)-3,4-dihydro-2(1H)-isoquinolinyl)-1,3,5-triazin-2-yl)amino)benzamide | 473 | 22.58 |
| 276 | N-methyl-3-((4-(3-((2-(trifluoromethyl)phenoxy)methyl)-1-azetidinyl)-1,3,5-triazin-2-yl)amino)benzamide | 459 | 23.55 |
| 277 | N-methyl-3-((4-(4-((3-(trifluoromethoxy)benzyl)oxy)-1-piperidinyl)-1,3,5-triazin-2-yl)amino)benzamide | 503.2 | 25.38 |
| 278 | 3-((4-(3-(3-chlorophenoxy)-1-piperidinyl)-1,3,5-triazin-2-yl)amino)-N-methylbenzamide | 439 | 25.97 |
| 279 | 3-((4-(7-chloro-3,4-dihydro-2(1H)-isoquinolinyl)-1,3,5-triazin-2-yl)amino)-N-methylbenzamide | 395 | 26.41 |
| 280 | N-methyl-3-((4-(methyl((3-phenyl-1,2,4-oxadiazol-5-yl)methyl)amino)-1,3,5-triazin-2-yl)amino)benzamide | 417.2 | 27.66 |
| 281 | 3-((4-(8-methoxy-3,4-dihydro-2(1H)-isoquinolinyl)-1,3,5-triazin-2-yl)amino)-N-methylbenzamide | 391.2 | 27.89 |
| 282 | 3-fluoro-N-methyl-5-((4-((3-(4-(trifluoromethoxy)phenoxy)propyl)amino)-1,3,5-triazin-2-yl)amino)benzamide | 481 | >30.00 |
| 283 | 3-((4-(3-(4-chlorophenoxy)-1-azetidinyl)-1,3,5-triazin-2-yl)amino)-4-methoxy-N-methylbenzamide | 441 | >30.00 |
| 284 | 3-((4-(3-(4-fluorophenoxy)-1-azetidinyl)-1,3,5-triazin-2-yl)amino)-6-methyl-N-methylbenzamide | 409.2 | >30.00 |
| 285 | 3-((5-fluoro-4-(3-(4-fluorophenoxy)-1-azetidinyl)-2-pyrimidinyl)amino)-N-methylbenzamide | 412.0 | >30.00 |
| 286 | N-methyl-3-((4-(((6-methylimidazo[1,2-a]pyridin-2-yl)methyl)amino)-1,3,5-triazin-2-yl)amino)benzamide | 389.2 | >30.00 |
| 287 | N-methyl-3-((4-((2-(5-(5-methyl-2-thiophenyl)-1,3,4-oxadiazol-2-yl)ethyl)amino)-1,3,5-triazin-2-yl)amino)benzamide | 437.2 | >30.00 |
| 288 | 3-((4-((2-(5-chloro-1H-benzimidazol-2-yl)ethyl)amino)-1,3,5-triazin-2-yl)amino)-N-methylbenzamide | 423.2 | >30.00 |
| 289 | N-cyclopropyl-3-(((4-((3-(methylcarbamoyl)phenyl)amino)-1,3,5-triazin-2-yl)amino)methyl)-1,2,4-oxadiazole-5-carboxamide | 410.2 | >30.00 |
| 290 | 3-((4-(1-ethyl-2-oxo-1,2-dihydro-1'H-spiro[indole-3,4'-piperidin]-1'-yl)-1,3,5-triazin-2-yl)amino)-N-methylbenzamide | 458 | >30.00 |
| 291 | 2-fluoro-5-((4-(3-(4-fluorophenoxy)-1-azetidinyl)-1,3,5-triazin-2-yl)amino)benzamide | 399 | >30.00 |
| 292 | N-methyl-3-((4-(6-(2,2,2-trifluoro-1-hydroxyethyl)-3,4-dihydro-2(1H)-isoquinolinyl)-1,3,5-triazin-2-yl)amino)benzamide | 459 | >30.00 |
| 293 | 3-((4-(6-bromo-3,4-dihydro-2(1H)-isoquinolinyl)-1,3,5-triazin-2-yl)amino)-2-methylbenzamide | 440 | >30.00 |
| 294 | N-methyl-3-((4-(4-(3-phenylpropyl)-1-piperidinyl)-1,3,5-triazin-2-yl)amino)benzamide | 431 | >30.00 |
| 295 | 5-((4-(4-(3,4-dimethylphenyl)-1-piperazinyl)-1,3,5-triazin-2-yl)amino)-2-fluorobenzamide | 422 | >30.00 |
| 296 | N-methyl-3-((4-(4-(2-methylpropoxy)-1-piperidinyl)-1,3,5-triazin-2-yl)amino)benzamide | 385 | >30.00 |
| 297 | 3-((4-(3-(2-cyanophenoxy)-1-azetidinyl)-1,3,5-triazin-2-yl)amino)-N-methylbenzamide | 402.2 | >30.00 |
| 298 | N-methyl-3-((4-(7-(trifluoromethyl)-3,4-dihydro-2(1H)-isoquinolinyl)-1,3,5-triazin-2-yl)amino)benzamide | 429.2 | >30.00 |
| 299 | 3-((4-(6-cyano-3,4-dihydro-2(1H)-isoquinolinyl)-1,3,5-triazin-2-yl)amino)-N-methylbenzamide | 386.2 | >30.00 |
| 300 | 3-((4-(3-((4-fluoro-3-methylphenoxy)methyl)-1-azetidinyl)-1,3,5-triazin-2-yl)amino)-N-methylbenzamide | 423 | |
| 301 | 3-((4-(4-(((2-fluorobenzyl)oxy)methyl)-1-piperidinyl)-1,3,5-triazin-2-yl)amino)-N-methylbenzamide | 451 | |
| 302 | 3-((4-(4-(4-cyano-2,3-difluorophenyl)-1-piperidinyl)-1,3,5-triazin-2-yl)amino)-N-methylbenzamide | 450 | |
| 303 | N-(3-chlorophenyl)-4-((3-(methylcarbamoyl)phenyl)amino)-1,3,5-triazin-2-yl)-1-piperazinecarboxamide | 467.2 | |
| 304 | 3-((4-(4-(3,4-dihydro-2(1H)-isoquinolinyl)-1-piperidinyl)-1,3,5-triazin-2-yl)amino)-N-methylbenzamide | 443 | |
| 305 | 3-((4-((3R)-3-(benzyloxy)-1-pyrrolidinyl)-1,3,5-triazin-2-yl)amino)-N-methylbenzamide | 405.2 | |
| 306 | N-methyl-3-((4-(4-(3-pyridinyl)-1,2,4-oxadiazol-5-yl)-1-piperidinyl)-1,3,5-triazin-2-yl)amino)benzamide | 458.2 | |
| 307 | N-methyl-3-((4-(4-propyl-1-piperidinyl)-1,3,5-triazin-2-yl)amino)benzamide | 355 | |
| 308 | 3-((4-(4-(3-(2-furanyl)-1H-pyrazol-5-yl)-1-piperidinyl)-1,3,5-triazin-2-yl)amino)-N-methylbenzamide | 445.2 | |
| 309 | N-methyl-3-((4-((3S)-3-(2-phenylethyl)-1-pyrrolidinyl)-1,3,5-triazin-2-yl)amino)benzamide and N-methyl-3-((4-((3R)-3-(2-phenylethyl)-1-pyrrolidinyl)-1,3,5-triazin-2-yl)amino)benzamide | 403.2 | |
| 310 | N-methyl-3-((4-((3-phenoxypropyl)amino)-1,3,5-triazin-2-yl)amino)benzamide | 379.2 | |
| 311 | 3-((4-(7-fluoro-3,4-dihydro-2(1H)-isoquinolinyl)-1,3,5-triazin-2-yl)amino)-N-methylbenzamide | 379.2 | |

TABLE 1-continued

| Compound Number | Name | Mass Spec. | hNav1.7 IC$_{50}$ (µM) (AVG) |
|---|---|---|---|
| 312 | mixture of N-methyl-3-((4-((3R)-3-phenyl-1-pyrrolidinyl)-1,3,5-triazin-2-yl)amino)benzamide and N-methyl-3-((4-((3S)-3-phenyl-1-pyrrolidinyl)-1,3,5-triazin-2-yl)amino)benzamide | 375.2 | |
| 313 | 3-((4-(6,8-difluoro-3,4-dihydro-2(1H)-isoquinolinyl)-1,3,5-triazin-2-yl)amino)-N-methylbenzamide | 397.2 | |
| 314 | 3-((4-(3-(4-(1H-imidazol-1-yl)phenoxy)-1-azetidinyl)-1,3,5-triazin-2-yl)amino)-N-methylbenzamide | 443 | |
| 315 | N-methyl-3-((4-((3R)-3-phenyl-1-piperidinyl)-1,3,5-triazin-2-yl)amino)benzamide | 389.2 | |
| 316 | 3-((4-(3-(4-fluorophenoxy)-1-azetidinyl)-1,3,5-triazin-2-yl)amino)-2-methylbenzamide | 395 | |
| 317 | 3-((4-(4-benzyl-1-piperazinyl)-1,3,5-triazin-2-yl)amino)-N-methylbenzamide | 404 | |
| 318 | 3-((4-(8-chloro-3,4-dihydro-2(1H)-isoquinolinyl)-1,3,5-triazin-2-yl)amino)-N-methylbenzamide | 395 | |
| 319 | N-methyl-3-((4-(3-(methylsulfonyl)-1-azetidinyl)-1,3,5-triazin-2-yl)amino)benzamide | 363 | |
| 320 | 3-((4-(4-(4-cyano-2-(trifluoromethoxy)phenyl)-1-piperidinyl)-1,3,5-triazin-2-yl)amino)-N-methylbenzamide | 498 | |
| 321 | 3-((4-(7-cyano-3,4-dihydro-2(1H)-isoquinolinyl)-1,3,5-triazin-2-yl)amino)-N-methylbenzamide | 386.2 | |
| 322 | 5-chloro-2-((1-(4-((3-(methylcarbamoyl)phenyl)amino)-1,3,5-triazin-2-yl)-3-azetidinyl)methoxy)benzamide | 468.2 | |
| 323 | N-methyl-3-((4-(1-piperidinyl)-1,3,5-triazin-2-yl)amino)benzamide | 313 | |
| 324 | N-methyl-3-((4-(((7-methylimidazo[1,2-a]pyridin-2-yl)methyl)amino)-1,3,5-triazin-2-yl)amino)benzamide | 389.2 | |
| 325 | N-methyl-3-((4-(4-(5-(1-methylethyl)-1,2,4-oxadiazol-3-yl)-1-piperidinyl)-1,3,5-triazin-2-yl)amino)benzamide | 423 | |
| 326 | 3-((4-(3-(4-chlorophenoxy)-1-piperidinyl)-1,3,5-triazin-2-yl)amino)-N-methylbenzamide | 439 | |
| 327 | mixture of 3-((4-((3S)-3-benzyl-1-pyrrolidinyl)-1,3,5-triazin-2-yl)amino)-N-methylbenzamide and 3-((4-((3R)-3-benzyl-1-pyrrolidinyl)-1,3,5-triazin-2-yl)amino)-N-methylbenzamide | 389.2 | |
| 328 | 3-((4-(4-hydroxy-4-phenyl-1-piperidinyl)-1,3,5-triazin-2-yl)amino)-N-methylbenzamide | 405 | |
| 329 | N-methyl-3-((4-(methyl((5-phenyl-1H-pyrazol-3-yl)methyl)amino)-1,3,5-triazin-2-yl)amino)benzamide | 415.2 | |
| 330 | N-methyl-3-((4-(1'H-spiro[indene-1,4'-piperidin]-1'-yl)-1,3,5-triazin-2-yl)amino)benzamide | 413 | |
| 331 | 3-((4-(4-(4-cyano-3,5-difluorophenyl)-1-piperidinyl)-1,3,5-triazin-2-yl)amino)-N-methylbenzamide | 450 | |
| 332 | 3-((4-(3-(4-chlorophenyl)-5,6-dihydro[1,2,4]triazolo[4,3-a]pyrazin-7(8H)-yl)-1,3,5-triazin-2-yl)amino)-N-methylbenzamide | 462 | |
| 333 | 3-((4-(3-(4-fluorobenzyl)-1-azetidinyl)-1,3,5-triazin-2-yl)amino)-N-methylbenzamide | 393.2 | |
| 334 | 3-((4-(5-benzyloctahydro-2H-pyrrolo[3,4-c]pyridin-2-yl)-1,3,5-triazin-2-yl)amino)-N-methylbenzamide | 444.2 | |
| 335 | 3-((4-(2,8-diazaspiro[4.5]dec-8-yl)-1,3,5-triazin-2-yl)amino)-N-methylbenzamide | 368.2 | |
| 336 | 5-((4-(3-(4-chlorophenoxy)-1-azetidinyl)-1,3,5-triazin-2-yl)amino)-N-methyl-1,3-benzenedicarboxamide | 454.2 | |
| 337 | 3-((4-(4-hydroxy-1-piperidinyl)-1,3,5-triazin-2-yl)amino)-N-methylbenzamide | 329 | |
| 338 | N-methyl-3-((4-(4-(5-phenyl-1,3,4-oxadiazol-2-yl)-1-piperidinyl)-1,3,5-triazin-2-yl)amino)benzamide | 456.2 | |
| 339 | 3-((4-(7-benzyl-2,7-diazaspiro[3.5]non-2-yl)-1,3,5-triazin-2-yl)amino)-N-methylbenzamide | 444.2 | |
| 340 | N-methyl-3-((4-(((5-methyl-1,3,4-oxadiazol-2-yl)methyl)amino)-1,3,5-triazin-2-yl)amino)benzamide | 341.2 | |
| 341 | 3-((4-(3-(4-fluorophenoxy)-1-azetidinyl)-1,3,5-triazin-2-yl)amino)-N-phenylbenzamide | 457 | |
| 342 | mixture of N-methyl-3-((4-((2R)-2-phenyl-4-morpholinyl)-1,3,5-triazin-2-yl)amino)benzamide and N-methyl-3-((4-((2S)-2-phenyl-4-morpholinyl)-1,3,5-triazin-2-yl)amino)benzamide | 391.2 | |
| 343 | 3-((4-(3-(4-fluorophenoxy)-1-azetidinyl)-1,3,5-triazin-2-yl)amino)-N,2-dimethylbenzamide | 409 | |
| 344 | N-methyl-3-((4-(4-(2-(2-methyl-1H-imidazol-1-yl)ethyl)-1-piperidinyl)-1,3,5-triazin-2-yl)amino)benzamide | 421 | |
| 345 | 3-((4-(3-(4-fluorophenoxy)-1-azetidinyl)-1,3,5-triazin-2-yl)amino)-N,N-dimethylbenzamide | 409 | |
| 346 | 3-((5-cyano-4-(3-(4-fluorophenoxy)-1-azetidinyl)-2-pyrimidinyl)amino)-N-methylbenzamide | 419.2 | |
| 347 | 3-((4-(4-tert-butyl-1-piperidinyl)-1,3,5-triazin-2-yl)amino)-N-methylbenzamide | 369 | |
| 348 | N-methyl-3-((4-(4-phenyl-1,3-thiazol-2-yl)-1-piperidinyl)-1,3,5-triazin-2-yl)amino)benzamide | 404 | |
| 349 | 3-((4-(dimethylamino)-1,3,5-triazin-2-yl)amino)-N-methylbenzamide | 273 | |
| 350 | 3-((4-(8-cyano-3,4-dihydro-2(1H)-isoquinolinyl)-1,3,5-triazin-2-yl)amino)-N-methylbenzamide | 386 | |
| 351 | N-methyl-3-((4-(4-methyl-1-piperazinyl)-1,3,5-triazin-2-yl)amino)benzamide | 328 | |
| 352 | 3-((4-(3-methoxy-1-azetidinyl)-1,3,5-triazin-2-yl)amino)-N-methylbenzamide | 315 | |
| 353 | N-methyl-3-((4-(4-(1-pyrrolidinyl)-1-piperidinyl)-1,3,5-triazin-2-yl)amino)benzamide | 382 | |
| 354 | 3-((4-(3-(4-fluorophenoxy)-1-azetidinyl)-1,3,5-triazin-2-yl)(methyl)amino)-N-methylbenzamide | 409 | |
| 355 | 3-((4-(8-fluoro-3,4-dihydro-2(1H)-isoquinolinyl)-1,3,5-triazin-2-yl)amino)-N-methylbenzamide | 379 | |
| 356 | 3-((4-(4-benzyl-4-hydroxy-1-piperidinyl)-1,3,5-triazin-2-yl)amino)-N-methylbenzamide | 419 | |
| 358 | N-methyl-3-((4-(4-propoxy-1-piperidinyl)-1,3,5-triazin-2-yl)amino)benzamide | 371 | |
| 359 | 6-((4-(3-(4-fluorophenoxy)-1-azetidinyl)-1,3,5-triazin-2-yl)amino)-N-methyl-2-pyridinecarboxamide | 396.2 | |
| 360 | 3-((4-(4-(4-cyano-3-(trifluoromethoxy)phenyl)-3,6-dihydro-1(2H)-pyridinyl)-1,3,5-triazin-2-yl)amino)-N-methylbenzamide | 496 | |
| 361 | 3-((4-(4-(hydroxy(phenyl)methyl)-1-piperidinyl)-1,3,5-triazin-2-yl)amino)-N-methylbenzamide | 419 | |
| 362 | 3-((4-(3-hydroxy-1-azetidinyl)-1,3,5-triazin-2-yl)amino)-N-methylbenzamide | 301 | |

TABLE 1-continued

| Compound Number | Name | Mass Spec. | hNav1.7 IC$_{50}$ (µM) (AVG) |
|---|---|---|---|
| 363 | N-methyl-3-((4-(4-(1-piperidinylcarbonyl)-1-piperidinyl)-1,3,5-triazin-2-yl)amino)benzamide | 424 | |
| 364 | 3-((4-(((5-tert-butyl-1H-pyrazol-3-yl)methyl)amino)-1,3,5-triazin-2-yl)amino)-N-methylbenzamide | 381.2 | |
| 365 | N-methyl-3-((4-((1-(5-methyl-1H-benzimidazol-2-yl)ethyl)amino)-1,3,5-triazin-2-yl)amino)benzamide | 403.2 | |
| 366 | 3-((4-(4-(5-fluoro-1H-benzimidazol-2-yl)-1-piperidinyl)-1,3,5-triazin-2-yl)amino)-N-methylbenzamide | 447.2 | |
| 367 | N-methyl-3-((4-(((3-methylimidazo[2,1-b][1,3]thiazol-6-yl)methyl)amino)-1,3,5-triazin-2-yl)amino)benzamide | 395 | |
| 368 | 5-((4-(3-(4-chlorophenoxy)-1-azetidinyl)-1,3,5-triazin-2-yl)amino)-N,N'-dimethyl-1,3-benzenedicarboxamide | 468.2 | |
| 369 | 3-((4-(4-cyclopentyl-1-piperazinyl)-1,3,5-triazin-2-yl)amino)-N-methylbenzamide | 382 | |
| 370 | 3-((4-(3-(4-chlorophenoxy)-1-azetidinyl)-1,3,5-triazin-2-yl)amino)-N-methyl-5-(trifluoromethyl)benzamide | 479 | |
| 371 | N-methyl-3-((4-(4-(1-methylethyl)-1-piperazinyl)-1,3,5-triazin-2-yl)amino)benzamide | 356 | |
| 372 | 3-((4-(4-tert-butyl-1-piperazinyl)-1,3,5-triazin-2-yl)amino)-N-methylbenzamide | 370 | |
| 373 | N-methyl-3-((4-(4-(4-morpholinyl)-1-piperidinyl)-1,3,5-triazin-2-yl)amino)benzamide | 398 | |
| 374 | N-methyl-3-((4-(4-((4-methylphenyl)sulfonyl)-1-piperidinyl)-1,3,5-triazin-2-yl)amino)benzamide | 467.2 | |
| 375 | 3-((4-(1,4'-bipiperidin-1'-yl)-1,3,5-triazin-2-yl)amino)-N-methylbenzamide | 396 | |
| 376 | 3-((4-(3-(benzylamino)-1-azetidinyl)-1,3,5-triazin-2-yl)amino)-N-methylbenzamide | 390.2 | |
| 377 | tert-butyl 8-(4-((3-(methylcarbamoyl)phenyl)amino)-1,3,5-triazin-2-yl)-2,8-diazaspiro[4.5]decane-2-carboxylate | 468.2 | |
| 378 | N-methyl-3-((4-((5-phenyl-1,3-thiazol-2-yl)amino)-1,3,5-triazin-2-yl)amino)benzamide | 404.1 | |
| 379 | 3-((5-cyano-2-(3-(4-fluorophenoxy)-1-azetidinyl)-4-pyrimidinyl)amino)-N-methylbenzamide | 419.2 | |
| 380 | mixture of 3-((4-((3S)-3-benzyl-1-piperidinyl)-1,3,5-triazin-2-yl)amino)-N-methylbenzamide and 3-((4-((3R)-3-benzyl-1-piperidinyl)-1,3,5-triazin-2-yl)amino)-N-methylbenzamide | 403.2 | |
| 381 | N-methyl-3-((4-(4-(4-morpholinylcarbonyl)-1-piperidinyl)-1,3,5-triazin-2-yl)amino)benzamide | 426 | |
| 382 | 3-((4-(6-bromo-3,4-dihydro-2(1H)-isoquinolinyl)-1,3,5-triazin-2-yl)amino)-N,N-dimethylbenzamide | 454 | |
| 383 | 3-((4-(4-(3,4-dimethylphenyl)-1-piperazinyl)-1,3,5-triazin-2-yl)amino)-2-methylbenzamide | 418 | |
| 384 | 3-((4-(4-(3,4-dimethylphenyl)-1-piperazinyl)-1,3,5-triazin-2-yl)amino)-N,2-dimethylbenzamide | 432 | |
| 385 | 3-((4-(6-bromo-3,4-dihydro-2(1H)-isoquinolinyl)-1,3,5-triazin-2-yl)amino)-N,2-dimethylbenzamide | 453 | |

For compounds 300 to 385, an IC$_{50}$ value was not obtained.

EMBODIMENTS (1) Within compounds of Formula (I):

I. In one embodiment, X is —NH—.

II. In another embodiment, X is —O—, —NMe-, or —S—

III. In yet another embodiment, S, T and U are —N—.

IV. In yet another embodiment, S and T are —N— and U is —CH—.

V. In yet another embodiment, T and U are —N— and S is —CH—.

VI. In yet another embodiment, T is —N— and S and U are —CH—.

Within embodiments (III), (IV), (V), and (VI) in one group of compounds X is —NH—.

Within embodiments (III), (IV), (V), and (VI) in one group of compounds X is —O—.

VII. Within compounds of Formula (I), and embodiments I-VI independently and groups within embodiments VI, in one group of compounds ring A is phenyl substituted as defined in the Summary. Within these embodiments, in another group of compounds, A is phenyl, $R^4$ is hydrogen or halo, preferably hydrogen, and $R^2$ is hydrogen, alkyl, hydroxy, alkoxy, halo, haloalkyl, or dialkylamino. Within these embodiments, in yet another group of compounds, A is phenyl, $R^4$ is hydrogen, and $R^2$ is hydrogen, methyl, fluoro, chloro, trifluoromethyl, dimethylamino, methoxy or hydroxyl. Within these embodiments, in another group of compounds, A is phenyl, $R^4$ is hydrogen, and $R^2$ is hydrogen, methyl, chloro, fluoro, or dimethylamino, preferably hydrogen, methyl, chloro or fluoro, more preferably hydrogen and the $R^1R^{1a}NCO$— group is meta to the X group. Within these embodiments, in another group of compounds A is phenyl, $R^4$ is hydrogen, and $R^2$ is alkyl, halo, haloalkyl, haloalkoxy, alkoxy or hydroxyl, preferably methyl, ethyl, chloro, fluoro, trifluoromethyl, trifluoromethoxy, methoxy or hydroxyl, preferably hydrogen, methyl, chloro or fluoro, and the $R^2$ group is ortho to $R^1R^{1a}NCO$— and para to X group and the $R^1R^1NCO$— group is meta to the X group.

Within these embodiments, in another group of compounds A is phenyl and $R^4$ and $R^2$ are independently alkyl, halo, haloalkyl, haloalkoxy, alkoxy or hydroxy. Within this embodiment, in yet another group of compounds A is phenyl, $R^4$ and $R^2$ are independently methyl, ethyl, propyl, fluoro, chloro, trifluoromethyl, trifluoromethoxy, methoxy or hydroxy. Within this embodiment, in one group of compounds A is phenyl, $R^4$ and $R^2$ are independently methyl, ethyl, chloro, fluoro, trifluoromethyl, trifluoromethoxy, methoxy or hydroxyl, preferably methyl, chloro or fluoro and the $R^1R^1NCO$— group is meta to the X group. Within this embodiment, in another group of compounds A is phenyl, $R^4$ and $R^2$ are independently methyl, ethyl, chloro, fluoro, trifluoromethyl, trifluoromethoxy, methoxy or hydroxyl, preferably methyl, chloro or fluoro, and the $R^2$ and $R^4$ groups are ortho to $R^1R^{1a}NCO$— and the $R^1R^{1a}NCO$— group is meta to the X group.

VII. Within compounds of Formula (I), and embodiments I-VI independently and groups within embodiments VI, in another embodiment, A is heteroaryl. Within this embodiment, in one group of compounds A is monocyclic heteroaryl, preferably pyridinyl or thiophenyl, $R^4$ is hydrogen, and $R^2$ is hydrogen, alkyl, halo, haloalkyl, haloalkoxy, alkoxy or hydroxy. Within this embodiment, in one group of compounds A is monocyclic heteroaryl, preferably pyridinyl or thiophenyl, $R^4$ and $R^2$ are independently alkyl, halo, haloalkyl, haloalkoxy, alkoxy or hydroxy.

VIII. Within compounds of Formula (I), and embodiments I-VII independently and groups within these embodiments, in one group of compounds, —NR⁵R⁶ is

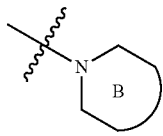

wherein ring B is heterocyclyl substituted as defined in the Summary. Preferably,

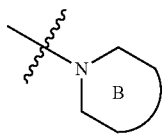

is monocyclic heterocyclyl substituted as defined in the Summary. Within these embodiments, in another group of compounds —NR⁵R⁶ is

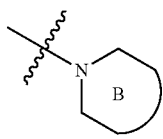

wherein ring B is azetidin-1-yl, pyrrolidin-1-yl, piperidin-1-yl or piperazin-1-yl substituted as defined in the Summary. Within these embodiments, in another group of compounds —NR⁵R⁶ is

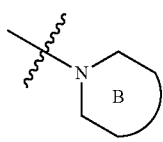

wherein ring B is unsaturated monocyclic heterocyclyl, preferably 1,2,5,6-tetrahydropiperidin-1-yl, substituted as defined in the Summary.

IX. Within compounds of Formula (I), and embodiments I-VII independently and

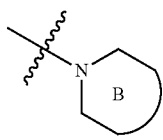

groups within these embodiments, in another group of compounds —NR⁵R⁶ is wherein ring B is piperidin-1-yl, piperazin-1-yl, or 3,6-dihydro-1(2H)-pyridinyl, each ring substituted at the 4-position with $R^b$ where $R^b$ is phenyl or heteroaryl, preferably phenyl, thiazolyl, pyrazolyl, pyridinyl, benzimidazolyl, or oxadiazolyl, each ring optionally substituted with $R^d$ or $R^e$ as defined in the Summary, preferably, $R^d$ is haloalkoxy, alkyl, haloalkyl, alkoxy, halo, cyano, heteroaryl, or phenyl (optionally substituted with halo) and $R^e$ is alkyl, haloalkoxy, halo, or haloalkyl.

X. Within compounds of Formula (I), and embodiments I-VII independently and groups within these embodiments, in another group of compounds —NR⁵R⁶ is

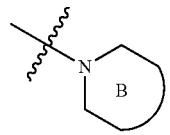

wherein ring B is azetidinyl, piperidin-1-yl or pyrrolidin-1-yl, preferably azetidin-1-yl or piperidin-1-yl, wherein azetidin-1-yl is substituted at the 3-position of the ring and piperidin-1-yl is substituted at the 3- or 4-position, preferably at the 4-position of piperidin-1-yl ring, with $R^b$ where $R^b$ is aryloxy, aralkyloxy or aryloxyalkyl optionally substituted with $R^d$, $R^e$, or $R^f$ as defined in the Summary, preferably $R^b$ is aryloxy or aryloxyalkyl, preferably phenyl, benzyloxy, or phenoxymethyl, optionally substituted with $R^d$ where $R^d$ is halo, haloalkyl, alkyl, haloalkoxy, alkoxy, cyano, phenyl, or cycloalkyl and $R^e$ where $R^e$ is alkyl or halo.

XI. Within compounds of Formula (I), and embodiments I-VII independently and groups within these embodiments, in another group of compounds —NR⁵R⁶ is

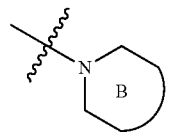

wherein ring B is 1,2,3,4-tetrahydroisoquinolin-2-yl substituted with $R^b$ as defined in the Summary, Preferably, ring B is 1,2,3,4-tetrahydroisoquinolin-2-yl substituted with $R^b$ at 6-position with haloalkoxy, cyano, cycloalkyl, halo, alkoxy, haloalkyl, or alkoxyalkoxy, preferably haloalkoxy or cycloalkyl.

XII. Within compounds of Formula (I), and embodiments I-VII independently and groups within these embodiments, in another group of compounds —NR⁵R⁶ is

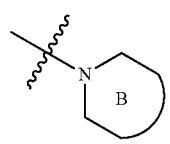

wherein ring B is 3-(4-chlorophenoxy)-1-azetidinyl, 3-((4-(trifluoromethyl)phenoxy)methyl)-1-azetidinyl, 3-(4-chloro-3-methylphenoxy)-1-azetidinyl, 3-(4-fluorophenoxy)-1-azetidinyl, 3-(4-chloro-3-fluorophenoxy)-1-azetidinyl, 3-(4-chloro-2-fluorophenoxy)-1-azetidinyl, 3-(3-chloro-4-fluorophenoxy)-1-azetidinyl, 3-(4-fluoro-2-methylphenoxy)-1-azetidinyl, 3-(3-ethylphenoxy)-1-azetidinyl, 3-(2,5-dichlorophenoxy)-1-azetidinyl, 3-(4-chloro-2-methylphenoxy)-1-azetidinyl, 3-(2,3-dihydro-1H-inden-5-yloxy)-1-azetidinyl, 3-(3-chlorophenoxy)-1-azetidinyl, 3-(2-chlorophenoxy)-1-azetidinyl, 3-(2-chloro-4-methylphenoxy)-1-azetidinyl, 3-phenoxy-1-azetidinyl, 3-(4-(trifluoromethyl)phenoxy)-1-azetidinyl, 3-(4- chlorophenoxy)methyl)-1-azetidinyl, 3-(4-(1-methylethyl)phenoxy)-1-azetidinyl, 3-(3-methylphenoxy)-1-azetidinyl, 3-(2,4-dichlorophenoxy)-1-azetidinyl, 3-(3-(trifluoromethyl)phenoxy)-1-azetidinyl, 3-(2,6-dichlorophenoxy)-1-azetidinyl, 3-(2-chloro-5-methylphenoxy)-1-azetidinyl, 3-((4-(trifluoromethoxy)phenoxy)methyl)-1-azetidinyl, 3-((4-chloro-2-methylphenoxy)methyl)-1-azetidinyl, 3-(3-ethynylphenoxy)-1-azetidinyl, 3-(3-methoxyphenoxy)-1-azetidinyl, 3-(3-fluorophenoxy)-1-azetidinyl, 3-(4-methoxyphenoxy)-1-azetidinyl, 3-((4-chloro-3-fluorophenoxy)methyl)-1-azetidinyl, 3-((4-(trifluoromethoxy)benzyl)oxy)-1-azetidinyl, 3-(2,3-dichlorophenoxy)-1-azetidinyl, 3-(4-chloro-2-fluorophenoxy)methyl)-1-azetidinyl, 3-(3-(trifluoromethoxy)phenoxy)-1-azetidinyl, 3-((4-chlorobenzyl)oxy)-1-azetidinyl, 3-(3-chloro-4-cyanophenoxy)-1-azetidinyl, 3-((2,4-dichlorophenoxy)methyl)-1-azetidinyl, 3-(3-tert-butylphenoxy)-1-azetidinyl, 3-(2-(trifluoromethyl)phenoxy)-1-azetidinyl, 3-(2,4-difluorophenoxy)-1-azetidinyl, 3-(2-fluoro-5-methylphenoxy)-1-azetidinyl, 3-((3,4-dichlorophenoxy)methyl)-1-azetidinyl, 3-((4-fluorophenoxy)methyl)-1-azetidinyl, 3-((3-(trifluoromethoxy)phenoxy)methyl)-1-azetidinyl, 3-(2,5-difluorophenoxy)-1-azetidinyl, 3-(2-(trifluoromethoxy)phenoxy)-1-azetidinyl, 3-methyl-3-(4-methylphenoxy)-1-azetidinyl, 3-(4-chlorophenyl)-1-azetidinyl, 3-((1R& 1S)-1-(4-chlorophenyl)ethyl)-1-azetidinyl, 3-(3,5-difluorophenoxy)-1-azetidinyl, 3-((3-(trifluoromethyl)phenoxy)-methyl)-1-azetidinyl, 3-(2-fluorophenoxy)-1-azetidinyl, 3-(2-chloro-4-(trifluoromethyl)phenoxy)-1-azetidinyl, 3-(3-biphenylyloxy)-1-azetidinyl, 3-((3-chlorophenoxy)methyl)-1-azetidinyl, 3-(2-methoxyphenoxy)-1-azetidinyl, 3-((4-chloro-3-(trifluoromethyl)phenoxy)methyl)-1-azetidinyl, 3-(4-cyanophenoxy)-1-azetidinyl, 3-(2-biphenylyloxy)-1-azetidinyl, 3-((4-methoxyphenoxy)methyl)-1-azetidinyl, 3-(3,5-dichlorophenoxy)-1-azetidinyl, 3-(2,3,4-trifluorophenoxy)-1-azetidinyl, 3-((2-(trifluoromethoxy)phenoxy)methyl-)-1-azetidinyl, 3-((2-naphthalenyloxy)methyl)-1-azetidinyl, 3-((3-fluorophenoxy)methyl)-1-azetidinyl, 3-((3-methoxyphenoxy)methyl)-1-azetidinyl, 3-((2-chlorophenoxy)methyl)-1-azetidinyl, 3-((2-fluorophenoxy)methyl)-1-azetidinyl, 3-((1-naphthalenyloxy)methyl)-1-azetidinyl, 3-(((5-chloro-8-quinolinyl)oxy)methyl)-1-azetidinyl, 3-(2-fluoro-3-(trifluoromethyl)phenoxy)-1-azetidinyl, 3-((4-cyanophenoxy)methyl)-1-azetidinyl, 3-methyl-3-phenoxy-1-azetidinyl, 3-(4-cyclopentylphenoxy)-1-azetidinyl, 3-((4-fluorobenzyl)oxy)-1-azetidinyl, 3-methyl-3-(phenoxymethyl)-1-azetidinyl, 3-(2,6-difluorophenoxy)-1-azetidinyl, 3-((2-(trifluoromethyl)phenoxy)methyl)-1-azetidinyl, 3-(2-cyanophenoxy)-1-azetidinyl, 3-(benzylamino)-1-azetidinyl, 3-(4-fluorobenzyl)-1-azetidinyl, 3-(methylsulfonyl)-1-azetidinyl, 3-methoxy-1-azetidinyl, 3-((4-fluoro-3-methylphenoxy)methyl)-1-azetidinyl, 3-hydroxy-1-azetidinyl, 3-(4-(1H-imidazol-1-yl)phenoxy)-1-azetidinyl, 3-(3,4-dichlorophenoxy)-1-azetidinyl, 3-(4-chloro-2,6-difluorophenoxy)-1-azetidinyl, 3-(3,4-difluorophenoxy)-1-azetidinyl, 4-(4-phenyl-1,3-thiazol-2-yl)-1-piperidinyl, 4-(2-phenyl-1,3-thiazol-4-yl)-1-piperidinyl, 4-((4-chlorophenyl)carbonyl)-1-piperidinyl, 4-phenoxy-1-piperidinyl, 4-(3-fluorophenoxy)-1-piperidinyl, 4-(4-(trifluoromethyl)phenoxy)-1-piperidinyl, 4-(4-phenyl-1-piperidinyl, 4-(3-fluoro-4-(trifluoromethoxy)phenoxy)-1-piperidinyl, 4-(4-chloro-3-fluorophenoxy)-1-piperidinyl, 4-(2-chlorophenoxy)-1-piperidinyl, 4-((phenylcarbonyl)-1-piperidinyl, 4-((3,4-difluorophenoxy)methyl)-1-piperidinyl, 4-(2,2,2-trifluoroethoxy)phenoxy)-1-piperidinyl, 4-(3,4-dimethylphenyl)-1-piperidinyl, 4-(4-(trifluoromethyl)phenoxy)-1-piperidinyl, 4-(3-(trifluoromethoxy)phenoxy)-1-piperidinyl, 4-(3-chlorophenoxy)-1-piperidinyl, 4-(phenylethynyl)-1-piperidinyl, 4-((4-(trifluoromethoxy)benzyl)oxy)-1-piperidinyl, 4-(4-(trifluoromethoxy)phenyl)-1-piperidinyl, 4-(4-phenyl-1H-pyrazol-1-yl)-1-piperidinyl, 4-(3-phenyl-1,2,4-oxadiazol-5-yl)-1-piperidinyl, 4-(phenoxymethyl)-1-piperidinyl, 4-chlorophenoxy)-1-piperidinyl, 4-(4-chlorophenyl)-4-cyano-1-piperidinyl, 4-((4-(trifluoromethyl)benzyl)oxy)-1-piperidinyl, 4-(3,4-difluorobenzyl)-1-piperidinyl, 4-(4-chloro-3-(trifluoromethoxy)phenoxy)-1-piperidinyl, 4-(4-chlorophenyl)-1H-pyrazol-1-yl)-1-piperidinyl, 4-(5-methyl-4-phenyl-1,3-thiazol-2-yl)-1-piperidinyl, 4-(4-cyanophenyl)-1-piperidinyl, 4-(2-pyridinyloxy)-1-piperidinyl, 4-(2-chlorophenyl)-1H-pyrazol-1-yl)-1-piperidinyl, 4-(4-fluoro-3-(trifluoromethoxy)phenoxy)-1-piperidinyl, 4-(4-fluorobenzyl)-1-piperidinyl, 4-(benzyloxy)-1-piperidinyl, 4-(2-(trifluoromethoxy)phenoxy)-1-piperidinyl, 3-(2-chlorophenoxy)-1-piperidinyl, 4-(4-cyano-3-(trifluoromethyl)phenyl)-1-piperidinyl, 4-((3,4-difluorobenzyl)oxy)-1-piperidinyl, 4-benzyl-1-piperidinyl, 4-(3-(1-methylethyl)-1,2,4-oxadiazol-5-yl)-1-piperidinyl, 4-(2-fluorophenoxy)-1-piperidinyl, 4-((3-(trifluoromethyl)benzyl)oxy)-1-piperidinyl, 4-(4-cyano-4-fluorophenyl)-1-piperidinyl, 4-(3-propyl-1,2,4-oxadiazol-5-yl)-1-piperidinyl, 4-(4-cyano-3-(trifluoromethoxy)phenyl)-1-piperidinyl, 4-(4-chlorophenyl)-1-piperidinyl, 4-(4-((4-methylphenyl)sulfanyl)-1-piperidinyl, 4-(4-(phenylamino)-1-piperidinyl, 4-((4-(trifluoromethoxy)benzyl)oxy)-1-piperidinyl, 4-((3-(trifluoromethoxy)benzyl)oxy)-1-piperidinyl, 3-(3-chlorophenoxy)-1-piperidinyl, 4-(3-phenylpropyl)-1-piperidinyl, 4-(2-methylpropoxy)-1-piperidinyl, (3R)-3-phenyl-1-piperidinyl, (3R & 3S)-3-benzyl-1-piperidinyl, 4-(5-fluoro-1H-benzimidazol-2-yl)-1-piperidinyl, 4-(3-(2-furanyl)-1H-pyrazol-5-yl)-1-piperidinyl, 4-(3-(3-pyridinyl)-1,2,4-oxadiazol-5-yl)-1-piperidinyl, 4-((4-methylphenyl)sulfonyl)-1-piperidinyl, 4-(5-phenyl-1,3,4-oxadiazol-2-yl)-1-piperidinyl, 4-(5-(1-methylethyl)-1,2,4-oxadiazol-3-yl)-1-piperidinyl, 4-(2-(2-methyl-1H-imidazol-1-yl)ethyl)-1-piperidinyl, 4-(3,4-dihydro-2(1H)-isoquinolinyl)-1-piperidinyl, 4-(4-cyano-3,5-difluorophenyl)-1-piperidinyl, 4-(4-cyano-2-(trifluoromethoxy)phenyl)-1-piperidinyl, 4-(4-cyano-2,3-difluorophenyl)-1-piperidinyl, 4-(1-pyrrolidinyl)-1-piperidinyl, 4-(4-morpholinylcarbonyl)-1-piperidinyl, 4-(1-piperidinylcarbonyl)-1-piperidinyl, 4-benzyl-4-hydroxy-1-piperidinyl, 4-hydroxy-1-piperidinyl, 1,4'-bipiperidin-1'-yl, 4-propyl-1-piperidinyl, 1-piperidinyl, 4-(4-morpholinyl)-1-piperidinyl, 4-propoxy-1-piperidinyl, 4-tert-butyl-1-piperidinyl, 4-(3-(trifluoromethoxy)phenyl)-1-piperazinyl, 4-(4-methylphenyl)-1-piperazinyl, 4-(3-(trifluoromethyl)phenyl)-1-piperazinyl, 4-(3-methoxyphenyl)-1-piperazinyl, 4-(3,4-dimethylphenyl)-1-piperazinyl, 4-(3-fluorophenyl)-1-piperazinyl, 4-(3-chlorophenyl)-1-piperazinyl, 4-(4-(trifluoromethyl)phenyl)-1-piperazinyl, 4-(6-methyl-2-pyridinyl)-1-piperazinyl, 4-(2,3-dimethylphenyl)-1-piperazinyl, 4-(4-(trifluoromethoxy)phenyl)-1-piperazinyl, 4-(2-methylphenyl)-1-piperazinyl, 4-(2-fluorophenyl)-1-piperazinyl, 4-(5-chloro-2-pyridinyl)-1-piperazinyl, 4-(4-(2-phenylethyl)-1-piperazinyl, 4-(3-methylphenyl)-1-piperazinyl, 4-(4-phenyl-1-piperazinyl, 4-(4-(6-methyl-2-pyridinyl)-1-piperazinyl, 4-((4-(trifluoromethoxy)phenyl)sulfonyl)-1-piperazinyl, 4-(4-chlorophenyl)-1-piperazinyl, 4-(4-methoxyphenyl)-1-piperazinyl, 4-(2-(trifluoromethoxy)phenyl)-1-piperazinyl, 4-(2-(trifluoromethyl)phenyl)-1-piperazinyl, 4-(4-(trifluoromethoxy)benzyl)-1-piperazinyl, 4-(2-(trifluoromethoxy)benzyl)-1-piperazinyl, 4-(4-cyanophenyl)-1-piperazinyl, 4-(4-fluorophenyl)-1-piperazinyl, 4-(3,4-dimethylphenyl)-1- piperazinyl, 4-(3-chloro-4-fluorophenyl)-1-piperazinyl, 4-(3,4-dimethylphenyl)-1-piperazinyl, 4-(4-(1-methylethyl)-1-piperazinyl, 4-benzyl-1-piperazinyl, 4-tert-butyl-1-piperazinyl, 4-methyl-1-piperazinyl, 4-cyclopentyl-1-piperazinyl, 6-(2,2,2-trifluoroethoxy)-3,4-dihydro-2(1H)-isoquinolinyl, 5-cyano-3,4-dihydro-2(1H)-isoquinolinyl, 6-(3,3,3-trifluoropropoxy)-3,4-dihydro-2(1H)-isoquinolinyl, 6-cyclopropyl-3,4-dihydro-2(1H)-isoquinolinyl, 6-(trifluoromethoxy)-3,4-dihydro-2(1H)-isoquinolinyl, 5-(trifluoromethoxy)-3,4-dihydro-2(1H)-isoquinolinyl, 6-chloro-3,4-dihydro-2(1H)-isoquinolinyl, 5-(2,2,2-trifluoroethoxy)-3,4-dihydro-2(1H)-isoquinolinyl, 5-methoxy-3,4-dihydro-2(1H)-isoquinolinyl, 5-chloro-3,4-dihydro-2(1H)-isoquinolinyl, 6-fluoro-3,4-dihydro-2(1H)-isoquinolinyl, 6-(trifluoromethyl)-3,4-dihydro-2(1H)-isoquinolinyl, 7-methoxy-3,4-dihydro-2(1H)-isoquinolinyl, 6-bromo-3,4-dihydro-2(1H)-isoquinolinyl, 6-methoxy-3,4-dihydro-2(1H)-isoquinolinyl, 5-fluoro-3,4-dihydro-2(1H)-isoquinolinyl, 6-(2-methoxyethoxy)-3,4-dihydro-2(1H)-isoquinolinyl, 6-methyl-3,4-dihydro-2(1H)-isoquinolinyl, 3,4-dihydro-2(1H)-isoquinolinyl, 5-(2-methoxyethoxy)-3,4-dihydro-2(1H)-isoquinolinyl, 8-(trifluoromethyl)-3,4-dihydro-2(1H)-isoquinolinyl, 7-chloro-3,4-dihydro-2(1H)-isoquinolinyl, 8-methoxy-3,4-dihydro-2(1H)-isoquinolinyl, 7-(trifluoromethyl)-3,4-dihydro-2(1H)-isoquinolinyl, 6-cyano-3,4-dihydro-2(1H)-isoquinolinyl, 8-fluoro-3,4-dihydro-2(1H)-isoquinolinyl, 7-fluoro-3,4-dihydro-2(1H)-isoquinolinyl, 8-chloro-3,4-dihydro-2(1H)-isoquinolinyl, 8-cyano-3,4-dihydro-2(1H)-isoquinolinyl, 7-cyano-3,4-dihydro-2(1H)-isoquinolinyl, 6,8-difluoro-3,4-dihydro-2(1H)-isoquinolinyl, 4-(2-phenyl-1,3-thiazol-4-yl)-3,6-dihydro-1(2H)-pyridinyl, 4-(4-phenyl-1,3-thiazol-2-yl)-3,6-dihydro-1(2H)-pyridinyl, 4-(4-cyanophenyl)-3,6-dihydro-1(2H)-pyridinyl, 4-(3,4-dimethylphenyl)-3,6-dihydro-1(2H)-pyridinyl, 4-(4-(trifluoromethoxy)phenyl)-3,6-dihydro-1(2H)-pyridinyl, 4-(4-cyano-3-(trifluoromethoxy)phenyl)-3,6-dihydro-1(2H)-pyridinyl, (2R and 2S)-2-phenyl-4-morpholinyl, (3R & 3S)-3-benzyl-1-pyrrolidinyl, (3R & 3S)-3-(2-phenylethyl)-1-pyrrolidinyl, or 3-(benzyloxy)-1-pyrrolidinyl.

Preferably, ring B is 3-(4-chlorophenoxy)-1-azetidinyl, 3-((4-(trifluoromethyl)-phenoxy)methyl)-1-azetidinyl, 3-(4-chloro-3-methylphenoxy)-1-azetidinyl, 3-(4-fluorophenoxy)-1-azetidinyl, 3-(4-chloro-3-fluorophenoxy)-1-azetidinyl, 3-(4-chloro-2-fluorophenoxy)-1-azetidinyl, 3-(3-chloro-4-fluorophenoxy)-1-azetidinyl, 3-(4-fluoro-2-methylphenoxy)-1-azetidinyl, 3-(3-ethylphenoxy)-1-azetidinyl, 3-(2,5-dichlorophenoxy)-1-azetidinyl, 3-(4-chloro-2-methylphenoxy)-1-azetidinyl, 3-(2,3-dihydro-1H-inden-5-yloxy)-1-azetidinyl, 3-(3-chlorophenoxy)-1-azetidinyl, 3-(2-chlorophenoxy)-1-azetidinyl, 3-(2-chloro-4-methylphenoxy)-1-azetidinyl, 3-phenoxy-1-azetidinyl, 3-(4-(trifluoromethyl)-phenoxy)-1-azetidinyl, 3-((4-chlorophenoxy)methyl)-1-azetidinyl, 3-(4-(1-methylethyl)phenoxy)-1-azetidinyl, 3-(3-methylphenoxy)-1-azetidinyl, 3-(2,4-dichlorophenoxy)-1-azetidinyl, 3-(3-(trifluoromethyl)phenoxy)-1-azetidinyl, 3-(2,6-dichlorophenoxy)-1-azetidinyl, 3-(2-chloro-5-methylphenoxy)-1-azetidinyl, 3-((4-(trifluoromethoxy)phenoxy)methyl)-1-azetidinyl, 3-((4-chloro-2-methylphenoxy)methyl)-1-azetidinyl, 3-(3-ethynylphenoxy)-1-azetidinyl, 3-(3-methoxyphenoxy)-1-azetidinyl, 3-(3-fluorophenoxy)-1-azetidinyl, 3-(4-methoxyphenoxy)-1-azetidinyl, 3-((4-chloro-3-fluorophenoxy)methyl)-1-azetidinyl, 3-((4-(trifluoromethoxy)benzyl)oxy)-1-azetidinyl, 3-(2,3-dichlorophenoxy)-1-azetidinyl, 3-((4-chloro-2-fluorophenoxy)methyl)-1-azetidinyl, 3-(3-(trifluoromethoxy)phenoxy)-1-azetidinyl, 3-((4-chlorobenzyl)oxy)-1-azetidinyl, 3-(3-chloro-4-cyanophenoxy)-1-azetidinyl, 3-((2,4-dichlorophenoxy)methyl)-1-azetidinyl, 3-(3-tert-butylphenoxy)-1-azetidinyl, 3-(2-(trifluoro-methyl)phenoxy)-1-azetidinyl, 3-(2,4-difluorophenoxy)-1-azetidinyl, 3-(2-fluoro-5-methylphenoxy)-1-azetidinyl, 3-((3,4-dichlorophenoxy)methyl)-1-azetidinyl, 3-((4-fluoro-phenoxy)methyl)-1-azetidinyl, 3-((3-(trifluoromethoxy)phenoxy)methyl)-1-azetidinyl, 3-(2,5-difluorophenoxy)-1-azetidinyl, 3-(2-(trifluoromethoxy)phenoxy)-1-azetidinyl, 3-methyl-3-(4-methylphenoxy)-1-azetidinyl, 3-(4-chlorophenyl)-1-azetidinyl, 3-((1R& 1S)-1-(4-chlorophenoxy)ethyl)-1-azetidinyl, 3-(3,5-difluorophenoxy)-1-azetidinyl, 3-((3-(trifluoromethyl)-phenoxy)-methyl)-1-azetidinyl, 3-(2-fluorophenoxy)-1-azetidinyl, 3-(2-chloro-4-(trifluoromethyl)phenoxy)-1-azetidinyl, 3-(3-biphenylyloxy)-1-azetidinyl, 3-((3-chlorophenoxy)methyl)-1-azetidinyl, 3-(2-methoxyphenoxy)-1-azetidinyl, 3-((4-chloro-3-(trifluoromethyl)phenoxy)methyl)-1-azetidinyl, 3-(4-cyanophenoxy)-1-azetidinyl, 3-(2-biphenylyloxy)-1-azetidinyl, 3-((4-methoxyphenoxy)methyl)-1-azetidinyl, 3-(3,5-dichlorophenoxy)-1-azetidinyl, 3-(2,3,4-trifluorophenoxy)-1-azetidinyl, 3-((2-(trifluoromethoxy)-phenoxy)methyl)-1-azetidinyl, 3-((2-naphthalenyloxy)methyl)-1-azetidinyl, 3-((3-fluoro-phenoxy)methyl)-1-azetidinyl, 3-((3-methoxyphenoxy)methyl)-1-azetidinyl, 3-((2-chlorophenoxy)methyl)-1-azetidinyl, 3-((2-fluorophenoxy)methyl)-1-azetidinyl, 3-((1-naphthalenyloxy)methyl)-1-azetidinyl, 3-(((5-chloro-8-quinolinyl)oxy)methyl)-1-azetidinyl, 3-(2-fluoro-3-(trifluoromethyl)phenoxy)-1-azetidinyl, 3-((4-cyanophenoxy)methyl)-1-azetidinyl, 3-methyl-3-phenoxy-1-azetidinyl, 3-(4-cyclopentylphenoxy)-1-azetidinyl, 3-((4-fluorobenzyl)-oxy)-1-azetidinyl, 3-methyl-3-(phenoxymethyl)-1-azetidinyl, 3-(2,6-difluorophenoxy)-1-azetidinyl, 3-((2-(trifluoromethyl)phenoxy)methyl)-1-azetidinyl, 3-(2-cyanophenoxy)-1-azetidinyl, 3-(benzylamino)-1-azetidinyl, 3-(4-fluorobenzyl)-1-azetidinyl, 3-(methylsulfonyl)-1-azetidinyl, 3-methoxy-1-azetidinyl, 3-((4-fluoro-3-methylphenoxy)methyl)-1-azetidinyl, 3-hydroxy-1-azetidinyl, 3-(4-(1H-imidazol-1-yl)phenoxy)-1-azetidinyl, 3-(3,4-dichlorophenoxy)-1-azetidinyl, 3-(4-chloro-2,6-difluorophenoxy)-1-azetidinyl, 3-(3,4-difluorophenoxy)-1-azetidinyl.

Preferably, ring B is 4-(4-phenyl-1,3-thiazol-2-yl)-1-piperidinyl, 4-(2-phenyl-1,3-thiazol-4-yl)-1-piperidinyl, 4-((4-chlorophenyl)carbonyl)-1-piperidinyl, 4-phenoxy-1-piperidinyl, 4-(3-fluorophenoxy)-1-piperidinyl, 4-(4-(trifluoromethoxy)phenoxy)-1-piperidinyl, 4-(4-phenyl-1-piperidinyl, 4-(3-fluoro-4-(trifluoromethoxy)phenoxy)-1-piperidinyl, 4-(4-chloro-3-fluorophenoxy)-1-piperidinyl, 4-(2-chlorophenoxy)-1-piperidinyl, 4-(4-(phenylcarbonyl)-1-piperidinyl, 4-((3,4-difluorophenoxy)methyl)-1-piperidinyl, 4-(2,2,2-trifluoroethoxy)phenoxy)-1-piperidinyl, 4-(3,4-dimethylphenyl)-1-piperidinyl, 4-(4-(trifluoromethyl)phenoxy)-1-piperidinyl, 4-(3-(trifluoromethoxy)phenoxy)-1-piperidinyl, 4-(3-chlorophenoxy)-1-piperidinyl, 4-(phenylethynyl)-1-piperidinyl, 4-((4-(trifluoromethoxy)benzyl)oxy)-1-piperidinyl, 4-(4-(trifluoromethoxy)phenyl)-1-piperidinyl, 4-(4-phenyl-1H-pyrazol-1-yl)-1-piperidinyl, 4-(3-phenyl-1,2,4-oxadiazol-5-yl)-1-piperidinyl, 4-(phenoxymethyl)-1-piperidinyl, 4-chlorophenoxy-1-piperidinyl, 4-(4-chlorophenyl)-4-cyano-1-piperidinyl, 4-((4-(trifluoromethyl)benzyl)oxy)-1-piperidinyl, 4-(3,4-difluorobenzyl)-1-piperidinyl, 4-(4-chloro-3-(trifluoromethoxy)phenoxy)-1-piperidinyl, 4-(4-chlorophenyl)-1H-pyrazol-1-yl)-1-piperidinyl, 4-(5-methyl-4-phenyl-1,3-thiazol-2-yl)-1-piperidinyl, 4-(4-cyanophenyl)-1-piperidinyl, 4-(2-pyridinyloxy)-1-piperidinyl, 4-(2-chlorophenyl)-1H-pyrazol-1-yl)-1-piperidinyl, 4-(4-fluoro-3-

(trifluoromethoxy)phenoxy)-1-piperidinyl, 4-(4-fluorobenzyl)-1-piperidinyl, 4-(benzyloxy)-1-piperidinyl, 4-(2-(trifluoromethoxy)phenoxy)-1-piperidinyl, 3-(2-chlorophenoxy)-1-piperidinyl, 4-(4-cyano-3-(trifluoromethyl)phenyl)-1-piperidinyl, 4-((3,4-difluorobenzyl)oxy)-1-piperidinyl, 4-benzyl-1-piperidinyl, 4-(3-(1-methylethyl)-1,2,4-oxadiazol-5-yl)-1-piperidinyl, 4-(2-fluorophenoxy)-1-piperidinyl, 4-((3-(trifluoromethyl)benzyl)oxy)-1-piperidinyl, 4-(4-cyano-4-(4-fluorophenyl)-1-piperidinyl, 4-(3-propyl-1,2,4-oxadiazol-5-yl)-1-piperidinyl, 4-(4-cyano-3-(trifluoromethoxy)phenyl)-1-piperidinyl, 4-(4-chlorophenyl)-1-piperidinyl, 4-(4-((4-methylphenyl)sulfanyl)-1-piperidinyl, 4-(4-(phenylamino)-1-piperidinyl, 4-((4-(trifluoromethoxy)benzyl)oxy)-1-piperidinyl, 4-((3-(trifluoromethoxy)benzyl)oxy)-1-piperidinyl, 3-(3-chlorophenoxy)-1-piperidinyl, 4-(3-phenylpropyl)-1-piperidinyl, 4-(2-methylpropoxy)-1-piperidinyl, (3R)-3-phenyl-1-piperidinyl, (3R & 3S)-3-benzyl-1-piperidinyl, 4-(5-fluoro-1H-benzimidazol-2-yl)-1-piperidinyl, 4-(3-(2-furanyl)-1H-pyrazol-5-yl)-1-piperidinyl, 4-(3-(3-pyridinyl)-1,2,4-oxadiazol-5-yl)-1-piperidinyl, 4-((4-methylphenyl)sulfonyl)-1-piperidinyl, 4-(5-phenyl-1,3,4-oxadiazol-2-yl)-1-piperidinyl, 4-(5-(1-methylethyl)-1,2,4-oxadiazol-3-yl)-1-piperidinyl, 4-(2-(2-methyl-1H-imidazol-1-yl)ethyl)-1-piperidinyl, 4-(3,4-dihydro-2(1H)-isoquinolinyl)-1-piperidinyl, 4-(4-cyano-3,5-difluorophenyl)-1-piperidinyl, 4-(4-cyano-2-(trifluoromethoxy)phenyl)-1-piperidinyl, 4-(4-cyano-2,3-difluorophenyl)-1-piperidinyl, 4-(1-pyrrolidinyl)-1-piperidinyl, 4-(4-morpholinylcarbonyl)-1-piperidinyl, 4-(1-piperidinylcarbonyl)-1-piperidinyl, 4-benzyl-4-hydroxy-1-piperidinyl, 4-hydroxy-1-piperidinyl, 1,4'-bipiperidin-1'-yl, 4-propyl-1-piperidinyl, 1-piperidinyl, 4-(4-morpholinyl)-1-piperidinyl, 4-propoxy-1-piperidinyl, or 4-tert-butyl-1-piperidinyl.

Preferably ring B is 4-(3-(trifluoromethoxy)phenyl)-1-piperazinyl, 4-(4-methylphenyl)-1-piperazinyl, 4-(3-(trifluoromethyl)phenyl)-1-piperazinyl, 4-(3-methoxyphenyl)-1-piperazinyl, 4-(3,4-dimethylphenyl)-1-piperazinyl, 4-(3-fluorophenyl)-1-piperazinyl, 4-(3-chlorophenyl)-1-piperazinyl, 4-(4-(trifluoromethyl)phenyl)-1-piperazinyl, 4-(6-methyl-2-pyridinyl)-1-piperazinyl, 4-(2,3-dimethylphenyl)-1-piperazinyl, 4-(4-(trifluoromethoxy)-phenyl)-1-piperazinyl, 4-(2-methylphenyl)-1-piperazinyl, 4-(2-fluorophenyl)-1-piperazinyl, 4-(5-chloro-2-pyridinyl)-1-piperazinyl, 4-(4-(2-phenylethyl)-1-piperazinyl, 4-(3-methylphenyl)-1-piperazinyl, 4-(4-phenyl-1-piperazinyl, 4-(4-(6-methyl-2-pyridinyl)-1-piperazinyl, 4-((4-(trifluoromethoxy)phenyl)sulfonyl)-1-piperazinyl, 4-(4-chlorophenyl)-1-piperazinyl, 4-(4-methoxyphenyl)-1-piperazinyl, 4-(2-(trifluoromethoxy)phenyl)-1-piperazinyl, 4-(2-(trifluoromethyl)phenyl)-1-piperazinyl, 4-(4-(trifluoromethoxy)benzyl)-1-piperazinyl, 4-(2-(trifluoromethoxy)benzyl)-1-piperazinyl, 4-(4-cyanophenyl)-1-piperazinyl, 4-(4-fluorophenyl)-1-piperazinyl, 4-(3,4-dimethylphenyl)-1-piperazinyl, 4-(3-chloro-4-fluorophenyl)-1-piperazinyl, 4-(3,4-dimethylphenyl)-1-piperazinyl, 4-(4-(1-methylethyl)-1-piperazinyl, 4-benzyl-1-piperazinyl, 4-tert-butyl-1-piperazinyl, 4-methyl-1-piperazinyl, or 4-cyclopentyl-1-piperazinyl.

Preferably ring B is 6-(2,2,2-trifluoroethoxy)-3,4-dihydro-2(1H)-isoquinolinyl, 5-cyano-3,4-dihydro-2(1H)-isoquinolinyl, 6-(3,3,3-trifluoropropoxy)-3,4-dihydro-2(1H)-isoquinolinyl, 6-cyclopropyl-3,4-dihydro-2(1H)-isoquinolinyl, 6-(trifluoromethoxy)-3,4-dihydro-2(1H)-isoquinolinyl, 5-(trifluoromethoxy)-3,4-dihydro-2(1H)-isoquinolinyl, 6-chloro-3,4-dihydro-2(1H)-isoquinolinyl, 5-(2,2,2-trifluoroethoxy)-3,4-dihydro-2(1H)-isoquinolinyl, 5-methoxy-3,4-dihydro-2(1H)-isoquinolinyl, 5-chloro-3,4-dihydro-2(1H)-isoquinolinyl, 6-fluoro-3,4-dihydro-2(1H)-isoquinolinyl, 6-(trifluoromethyl)-3,4-dihydro-2(1H)-isoquinolinyl, 7-methoxy-3,4-dihydro-2(1H)-isoquinolinyl, 6-bromo-3,4-dihydro-2(1H)-isoquinolinyl, 6-methoxy-3,4-dihydro-2(1H)-isoquinolinyl, 5-fluoro-3,4-dihydro-2(1H)-isoquinolinyl, 6-(2-methoxyethoxy)-3,4-dihydro-2(1H)-isoquinolinyl, 6-methyl-3,4-dihydro-2(1H)-isoquinolinyl, 3,4-dihydro-2(1H)-isoquinolinyl, 5-(2-methoxyethoxy)-3,4-dihydro-2(1H)-isoquinolinyl, 8-(trifluoro-methyl)-3,4-dihydro-2(1H)-isoquinolinyl, 7-chloro-3,4-dihydro-2(1H)-isoquinolinyl, 8-methoxy-3,4-dihydro-2(1H)-isoquinolinyl, 7-(trifluoromethyl)-3,4-dihydro-2(1H)-isoquinolinyl, 6-cyano-3,4-dihydro-2(1H)-isoquinolinyl, 8-fluoro-3,4-dihydro-2(1H)-isoquinolinyl, 7-fluoro-3,4-dihydro-2(1H)-isoquinolinyl, 8-chloro-3,4-dihydro-2(1H)-isoquinolinyl, 8-cyano-3,4-dihydro-2(1H)-isoquinolinyl, 7-cyano-3,4-dihydro-2(1H)-isoquinolinyl, or 6,8-difluoro-3,4-dihydro-2(1H)-isoquinolinyl.

XIII. Within compounds of Formula (I), and embodiments I-XII independently and groups within these embodiments, in another group of compounds, in yet another embodiment, $R^1$ is alkyl, preferably methyl ethyl or tert-butyl and $R^{1a}$ is hydrogen.

XIV. Within compounds of Formula (I), and embodiments I-XII independently and groups within these embodiments, in another group of compounds, in yet another embodiment, $R^1$ is haloalkyl, preferably 2,2,2-trifluoroethyl and $R^{1a}$ is hydrogen.

XV. Within compounds of Formula (I), and embodiments I-XII independently and groups within these embodiments, in another group of compounds $R^1$ is substituted alkyl and $R^{1a}$ is hydrogen. Within this embodiment, in one group of compounds $R^1$ is alkyl substituted with alkoxy Within this embodiment, in one group of compounds $R^1$ is 2-methoxyethyl. Within this embodiment, in one group of compounds $R^1$ is cyanomethyl.

XVI. Within compounds of Formula (I), and embodiments I-XII independently and groups within these embodiments, in another group of compounds, $R^1$ is monocyclic cycloalkyl and $R^{1a}$ is hydrogen. Within this embodiment, in one group of compounds $R^1$ is cyclopropyl.

XVII. Within compounds of Formula (I), and embodiments I-XVI independently and groups within these embodiments, in another group of compounds, $R^3$ is hydrogen.

Preferred compound of Invention are:
3-((4-(3-(4-chlorophenoxy)-1-azetidinyl)-1,3,5-triazin-2-yl)amino)-N-methyl-benzamide;
2-fluoro-N-methyl-5-((4-(4-(4-phenyl-1,3-thiazol-2-yl)-1-piperidinyl)-1,3,5-triazin-2-yl)amino)benzamide;
5-((4-(3-(4-chlorophenoxy)-1-azetidinyl)-1,3,5-triazin-2-yl)amino)-2-fluoro-N-methyl-benzamide;
N-methyl-3-((4-(3-((4-(trifluoromethyl)phenoxy)methyl)-1-azetidinyl)-1,3,5-triazin-2-yl)amino)benzamide;
2-fluoro-N-methyl-5-((4-(3-(4-(trifluoromethyl)phenoxy)-1-azetidinyl)-1,3,5-triazin-2-yl)amino)benzamide;
3-((2-(3-(4-chlorophenoxy)-1-azetidinyl)-4-pyrimidinyl)amino)-N-methylbenzamide;
3-((4-(3-(4-chloro-3-methylphenoxy)-1-azetidinyl)-1,3,5-triazin-2-yl)amino)-N-methylbenzamide;
2-chloro-N-methyl-5-((4-(6-(2,2,2-trifluoroethoxy)-3,4-dihydro-2(1H)-isoquinolinyl)-1,3,5-triazin-2-yl)amino)benzamide;
3-((4-(3-(4-fluorophenoxy)-1-azetidinyl)-2-pyrimidinyl)amino)-N-methylbenzamide;
3-((4-(3-(4-chloro-3-fluorophenoxy)-1-azetidinyl)-1,3,5-triazin-2-yl)amino)-N-methylbenzamide;

N-methyl-3-((4-((3-(4-(trifluoromethoxy)phenoxy)propyl)
   amino)-1,3,5-triazin-2-yl)-amino)benzamide;
5-((4-(3-(4-chloro-2-fluorophenoxy)-1-azetidinyl)-1,3,5-tri-
   azin-2-yl)amino)-2-fluoro-N-methylbenzamide;
3-((4-(3-(3-chloro-4-fluorophenoxy)-1-azetidinyl)-1,3,5-tri-
   azin-2-yl)amino)-N-methylbenzamide;
3-((4-(3-(4-fluoro-2-methylphenoxy)-1-azetidinyl)-1,3,5-
   triazin-2-yl)amino)-N-methylbenzamide;
3-((4-(3-(3-ethylphenoxy)-1-azetidinyl)-1,3,5-triazin-2-yl)
   amino)-N-methylbenzamide;
3-((4-(3-(2,5-dichlorophenoxy)-1-azetidinyl)-1,3,5-triazin-
   2-yl)amino)-N-methyl-benzamide;
3-((4-(3-(4-chloro-2-methylphenoxy)-1-azetidinyl)-1,3,5-
   triazin-2-yl)amino)-N-methylbenzamide;
3-((4-(3-(4-chloro-2-fluorophenoxy)-1-azetidinyl)-1,3,5-tri-
   azin-2-yl)amino)-N-methylbenzamide;
3-((4-(3-(2,3-dihydro-1H-inden-5-yloxy)-1-azetidinyl)-1,3,
   5-triazin-2-yl)amino)-N-methylbenzamide;
N-methyl-3-((4-(4-(3-(trifluoromethoxy)phenyl)-1-piper-
   azinyl)-1,3,5-triazin-2-yl)-amino)benzamide;
N-methyl-3-((4-(4-(4-phenyl-1,3-thiazol-2-yl)-1-piperidi-
   nyl)-1,3,5-triazin-2-yl)-amino)benzamide;
3-((4-(3-(3-chlorophenoxy)-1-azetidinyl)-1,3,5-triazin-2-yl)
   amino)-N-methyl-benzamide;
N-methyl-3-((4-(4-(2-phenyl-1,3-thiazol-4-yl)-1-piperidi-
   nyl)-1,3,5-triazin-2-yl)-amino)benzamide;
2-chloro-N-methyl-5-((4-(4-(4-phenyl-1,3-thiazol-2-yl)-1-
   piperidinyl)-1,3,5-triazin-2-yl)-amino)benzamide;
3-((4-(3-(4-chlorophenoxy)-1-azetidinyl)-1,3,5-triazin-2-yl)
   amino)-N-(2-methoxy-ethyl)benzamide;
3-((4-(3-(2-chlorophenoxy)-1-azetidinyl)-1,3,5-triazin-2-yl)
   amino)-N-methyl-benzamide;
3-((4-(3-(4-chlorophenoxy)-1-azetidinyl)-2-pyrimidinyl)
   amino)-N-methylbenzamide;
3-((4-(3-(2-chloro-4-methylphenoxy)-1-azetidinyl)-1,3,5-
   triazin-2-yl)amino)-N-methylbenzamide;
N-methyl-3-((4-(3-phenoxy-1-azetidinyl)-1,3,5-triazin-2-
   yl)amino)benzamide;
N-methyl-3-((4-(4-(4-methylphenyl)-1-piperazinyl)-1,3,5-
   triazin-2-yl)amino)-benzamide;
N-methyl-3-((4-(3-(4-(trifluoromethyl)phenoxy)-1-azetidi-
   nyl)-1,3,5-triazin-2-yl)-amino)benzamide;
3-((4-(4-((4-chlorophenyl)carbonyl)-1-piperidinyl)-1,3,5-
   triazin-2-yl)amino)-N-methylbenzamide;
3-((4-(3-(4-chlorophenoxy)-1-azetidinyl)-1,3,5-triazin-2-yl)
   amino)-5-fluoro-N-methylbenzamide;
3-((4-(3-(4-fluorophenoxy)-1-azetidinyl)-1,3,5-triazin-2-yl)
   amino)-N-(2-methoxy-ethyl)benzamide;
3-((4-(3-((4-chlorophenoxy)methyl)-1-azetidinyl)-1,3,5-tri-
   azin-2-yl)amino)-N-methylbenzamide;
N-methyl-3-((4-(6-(2,2,2-trifluoroethoxy)-3,4-dihydro-2
   (1H)-isoquinolinyl)-1,3,5-triazin-2-yl)amino)benzamide;
N-methyl-3-((4-(3-(4-(1-methylethyl)phenoxy)-1-azetidi-
   nyl)-1,3,5-triazin-2-yl)amino)benzamide;
N-methyl-3-((4-(4-(3-(trifluoromethyl)phenyl)-1-piperazi-
   nyl)-1,3,5-triazin-2-yl)amino)benzamide;
3-((4-(4-(3-methoxyphenyl)-1-piperazinyl)-1,3,5-triazin-2-
   yl)amino)-N-methyl-benzamide; or
N-methyl-3-((4-(4-phenoxy-1-piperidinyl)-1,3,5-triazin-2-
   yl)amino)benzamide, or a pharmaceutically acceptable
   salt thereof.

The following abbreviations may be used herein:
~ about
+ve or pos. ion positive ion
Δ heat
Ac acetyl
Ac₂O acetic anhydride
ACN acetonitrile
AcOH acetic acid
A-phos, Am-Phos (bis[4-di-tert-butylphosphino)-N,N-dim-
   ethylaniline]palladium dichloride)
aq aqueous
ATP adenosine 5'-triphosphate
BINAP 2,2'-bis(diphenylphosphino)-1,1'-binaphthyl
BOC or Boc tert-butyloxycarbonyl
Bu butyl
Bz benzyl
Calcd or Calc'd calculated
Conc. concentrated
d day(s)
DCE dichloroethylene
DCM dichloromethane
DEA diethylamine
DEAD diethyl azodicarboxylate
DIEA diisopropylethylamine
DIPEA N,N-diisopropylethylamine
DMA dimethylacetamide
DMAP 4-dimethylaminopyridine
DME dimethoxyl ethyl ether
DMF N,N-dimethylformamide
DMSO dimethyl sulfoxide
DTT dithiothreitol
ESI or ES electrospray ionization
Et ethyl
Et₂O diethyl ether
Et₃N triethylamine
EtOAc ethyl acetate
EtOH ethyl alcohol
FBS fetal bovine serum
g grams
h hour
HATU 2-(1H-7-azabenzotriazol-1-yl)-1,1,3,3-tetramethyl
   uronium hexafluorophosphate methanaminium
HCO₂H formic acid
Hex hexanes
HOAc acetic acid
HPLC high pressure liquid chromatography
IPA or iPrOH isopropyl alcohol
iPr₂NEt N-ethyl diisopropylamine
KOAc potassium acetate
LCMS, LC-MS or LC/MS liquid chromatography mass spec-
   troscopy
LDA lithium diisopropylamide
LHMDS or LiHMDS lithium hexamethyldisilazide
LiTMP lithium tetramethylpiperidide
m/z mass divided by charge
mCPBA m-chloroperoxybenzoic acid
Me methyl
MeCN acetonitrile
MeI iodomethane
MeOH methyl alcohol
mg milligrams
min minutes
mL milliliters
MPLC medium pressure liquid chromatography
MS mass spectra
MS mass spectrum
MsCl mesylchloride
NaHMDS sodium hexamethyldisilazide
NaHMDS sodium bis(trimethlysilyl)amide
NaOtBu sodium tert-butoxide
NBS N-bromosuccinimide
NMO N-methylmorpholine-N-oxide
NMP 1-methyl-2-pyrrolidinone NMR nuclear magnetic resonance
Pd₂dba₃ tris(dibenzylideneacetone)dipalladium(0)
PdCl₂(dppf) [1,1'-bis(diphenylphosphino)ferrocene]palladium(II) chloride
PMB paramethoxybenzyl
PPh₃ triphenylphosphine
PTSA para-toulene sulfonic acid
RT or rt room temperature
Sat. or sat'd or satd saturated
SFC supercritical fluid chromatography
t-BuOH tert-butylhydroxide
TFA trifluoroacetic acid
THF tetrahydrofuran
TLC thin layer chromatography
TMS tetramethylsilane
TPAP tetrapropylammonium perruthenate
Tris tris(hydroxymethyl)aminomethane
UV ultraviolet
xantphos (9,9-dimethyl-9H-xanthene-4,5-diyl)bis(diphenylphosphine)
X-Phos 2-dicyclohexylphosphino-2',4',6'-triisopropyl-1,1'-biphenyl When a percent (%) is used in connection with a solid composition, it is intended to be percent by mass. When used in connection with a liquid composition, it is intended to be percent by volume.

General Synthetic Schemes

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where X is —NH—, —NCH₃— or —O— and other groups are as defined in the Summary can be prepared as described in Scheme A below:

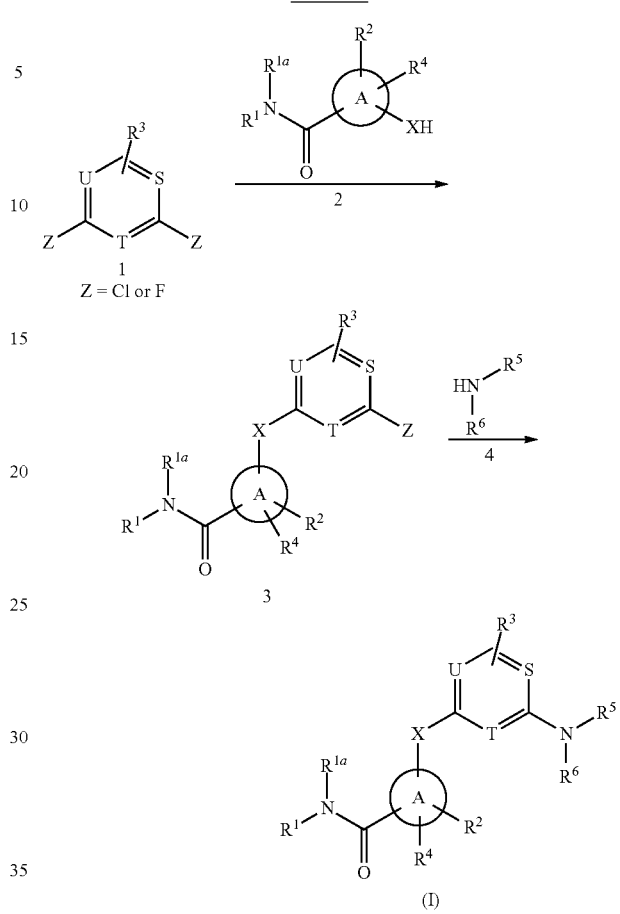

Scheme A

Reaction of a compound of formula 1 where Z is chloro or fluoro and other groups are as defined in the Summary with a compound of formula 2 where X is —N— or —O— and other groups are as defined in the Summary, in the presence of a base provides an a compound of formula 3. Suitable solvents for the reaction include DMF, DME, THF and alcohols such as ethanol, isopropanol, butanol and the like. Suitable bases include amine bases such as Et₃N and DIEA and the like, as well as bases such as K₂CO₃ and NaH and the like. Compounds of formula 1 and 2 are either commercially available or they can be prepared by methods well known in the art. For example, 2,4-dichloro-1,3,5-triazine, 3-amino-2-methylbenzamide are commercially available. Representative syntheses of compounds of formulae 1 and 2 are also provided in Working Examples below.

Compound of formula 3 can then be reacted with an amine of formula 4 in the presence of an acid or a base to give a compound of Formula (I) where X is —N— or —O—. Suitable solvents include alcohols such as ethanol, isopropanol, butanol and the like, as well as solvents such as THF and DMF and the like. Suitable acids include HCl and TFA and the like. Suitable bases include amine bases such as Et₃N and DIEA and the like, as well as bases such as K₂CO₃ and NaH and the like. Compounds of formula 4 are either commercially available or they can be prepared by methods well known in the art. For example, 5-fluoro-1,2,3,4-tetrahydro-isoquinoline hydrochloride, 4-(benzyloxy)piperidine, 4-(4-chlorophenoxy)-piperidine, 4-phenylpiperidine, methyl 1,2,3,4-tetrahydroisoquinoline-5-carboxylate, 4-(piperidin-4-yl)benzonitrile, 5-methoxy-1,2,3,4-tetrahydroisoquinoline, 4-(3-propyl-1,2,4-oxadiazol-5-yl)piperidine, 1,2,3,4-tetrahydroisoquinoline-5-carbonitrile, 4-(4-fluorophenoxy)-piperidine, 4-(4-phenyl-1H-pyrazol-1-yl)piperidine, 4-(4-phenyl-1H-1,2,3-triazol-1-yl)piperidine, 4-(3-chloro-4-fluorophenoxy)-piperidine, 6-methoxy-1,2,3,4-tetrahydroisoquinoline, 6-fluoro-1,2,3,4-tetrahydroisoquinoline, 4-(2-(trifluoromethyl)-phenoxy)-piperidine, 4-(4-chlorophenyl)piperidine, 3-phenylazetidine, 4-(azetidin-3-yl)benzonitrile, 3-(benzyloxy)-azetidine, 4-phenyl-azepane, 4-phenyl-1,2,3,6-tetrahydro-pyridine, 4-(4-fluorophenyl)-1,2,3,6-tetrahydropyridine, 4-(4-chlorophenyl)-1,2,3,6-tetrahydropyridine, and 4-(3-(trifluoromethyl)phenyl)-1,2,3,6-tetrahydropyridine are commercially available.

Compounds of Formula (I) can be converted to other compounds of Formula (I) by methods well known in the art. For example, compounds of Formula (I) where ring B is substituted with aryloxy, heteroaryloxy, cycloalkoxy, aralkyloxy, heteroaralkyloxy, heterocyclylalkyloxy, or cycloalkylalkyloxy can be prepared by reacting the corresponding compound of Formula (I) where ring B is substituted with a hydroxy group with aromatic or alicyclic halide under nucleophilic aromatic/aliphatic substitution reaction conditions well known in the art. Preferable solvents include DMF and the like and bases include potassium tert-butoxide and the like.

Compounds of Formula (I) where ring B is substituted with amino, mono or disubstituted amino can be prepared by first preparing a compound of Formula (I) wherein ring B carries an oxo group and then reacting it with an amine under reductive amination reaction conditions.

Compounds of Formula (I) where X is —NH— can be converted to a corresponding compound of Formula (I) where X is —NCH$_3$— by reacting it with methylhalide under suitable alkylating reaction conditions.

Alternatively, compounds of Formula (I) where X is —NH—, —NCH$_3$— or —O— and other groups are as defined in the Summary can be prepared as described in Scheme B below:

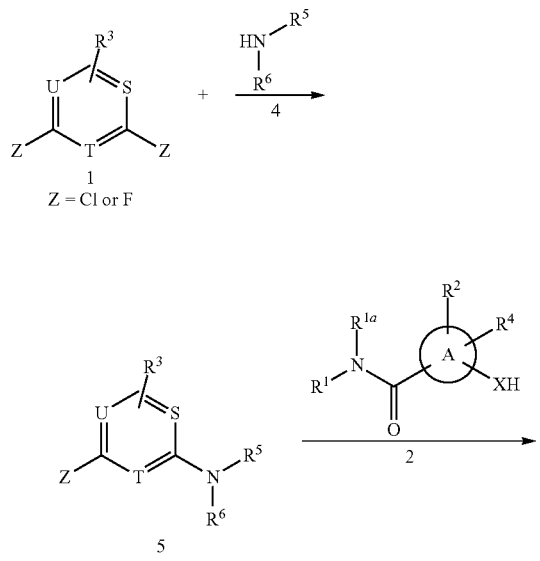

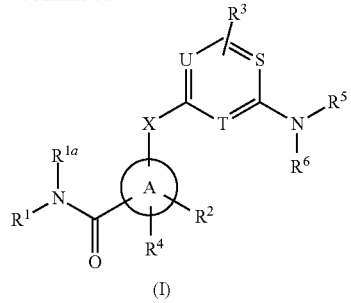

Reactions of a compound of formula 1 with an amine of formula 4 under the reactions conditions described in Scheme A above, provides a compound of formula 5 which upon reaction with a compound of formula 2 in the presence of a base provides a compound of Formula (I). Suitable solvents include DMF, THF and the like. Suitable bases include NaH and K$_2$CO$_3$ and the like.

The compounds of the invention are Nav1.7 inhibitors and hence are useful in the treatment of diseases such as chronic pain associated with, but are not limited to, post-herpetic neuralgia (shingles), osteoarthritis, painful diabetic neuropathy, complex regional pain syndrome (CRPS), cancer- or chemotherapy-induced pain, chronic back pain, phantom limb pain, trigeminal neuralgia, HIV-induced neuropathy, cluster headache disorders, migraine, Primary Erythromelalgia, and Paroxysmal Extreme Pain Disorder. Other potential indications for Nav1.7 inhibitors include but are not limited to depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M, Meisler M H, Richter A Exp Neurol 184(2):830-838, 2003), anxiety, depression: McKinney B C, Chow C Y, Meisler M H, Murphy G G, Genes Brain Behav. 7(6):629-638, 2008), learning and memory, cognition (Woodruff-Pak D S, Green J T, Levin S I, Meisler M H, Behav Neurosci 120(2):229-240, 2006), cardiac arrhythmia and fibrillation, contractility, congestive heart failure, sick sinus syndrome (Haufe V, Chamberland C, Dumaine R, J Mol Cell Cardiol 42(3):469-477, 2007), schizophrenia, neuroprotection after stroke, drug and alcohol abuse (Johannessen L C CNS Drugs 22(1)27-47, 2008), Alzheimer's (Kim D Y, Carey B W, Wang H, Ingano L A, Binshtok A M, Wertz M H, Pettingell W H, He P, Lee V M, Woolf C J, Kovacs D M, Nat Cell Biol 9(7):755-764, 2007), and cancer (Gillet L, Roger S, Besson P, Lecaille F, Gore J. Bougnoux P, Lalmanach G, Guennec L E, J Biol Chem 2009, Jan. 28 (epub)).

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain.

Another aspect of the invention relates to a pharmaceutical composition comprising a compound according to the present invention and a pharmaceutically-acceptable diluent or carrier.

Another aspect of the invention relates to the use of a compound according to the present invention as a medicament.

Another aspect of the invention relates to the use of a compound according to the present invention in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorder.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The Nav1.7 inhibitory activity of the compounds of the present invention can be tested using the in vitro and in vivo assays described in working Biological Examples below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day.

For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

EXAMPLES

The following preparations of compounds of Formula (I) and intermediates (References) are given to enable those skilled in the art to more clearly understand and to practice the present invention. They should not be considered as limiting the scope of the invention, but merely as being illustrative and representative thereof.

Reference A

Synthesis of 3-Amino-5-fluoro-N-methylbenzamide

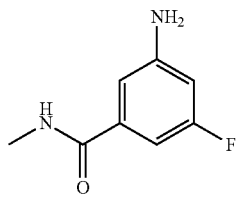

Step 1

To a roundbottom flask charged with 3-fluoro-5-nitrobenzoic acid (1.00 g, 5.40 mmol) was added DMF (6.75 mL), followed by Hunig's base (1.13 mL, 6.48 mmol), and HATU (2.157 g, 5.67 mmol). The flask was sealed with a septum and methanamine (2.0 M in THF) (13.5 mL, 27.0 mmol) was added via syringe. The resulting orange reaction mixture was stirred overnight at RT. After 16 h, the reaction mixture was diluted with $CH_2Cl_2$ (70 mL) and the resulting mixture was transferred to a separatory funnel and extracted with sat. aq. $NaHCO_3$ (3×30 mL). The organic layer was dried with $Na_2SO_4$, filtered and concentrated under reduced pressure. Purification with medium pressure silica gel chromatography using 70:30 Hex:EtOAc as the eluent afforded 3-fluoro-N-methyl-5-nitrobenzamide (961 mg, 4.85 mmol, 90%) as a yellow solid.

Step 2

To a roundbottom flask charged with 3-fluoro-N-methyl-5-nitrobenzamide (961 mg, 4.85 mmol) was added EtOH (16 mL). The resulting suspension was thoroughly purged with nitrogen prior to the addition of 10% Pd/C (43 mg, 0.485 mmol). The reaction mixture was purged with $H_2$ (g), then stirred under 1 atm. $H_2$ balloon at RT. After 2 d, the reaction mixture was filtered through Celite® (diatomaceous earth) with the aid of EtOH and the filtrate was dried under reduced pressure to afford 3-amino-5-fluoro-N-methylbenzamide (825 mg, 4.91 mmol, 100%).

The following compounds were prepared as described in Reference A above using appropriate starting materials.
3-amino-N,4-dimethylbenzamide
3-amino-4-fluoro-N-methylbenzamide
3-amino-5-fluoro-N-methylbenzamide
5-amino-2-fluoro-N-methylbenzamide
5-amino-N1,N3-dimethylisophthalamide
5-amino-N1-methylisophthalamide
3-amino-2,6-difluoro-N-methylbenzamide
5-amino-2-(dimethylamino)-N-methylbenzamide
5-amino-2-chloro-N-methylbenzamide
3-amino-N-methyl-5-(trifluoromethyl)benzamide
3-amino-4-methoxy-N-methylbenzamide

Reference B1

Synthesis of 3-substituted alkoxyazetidine

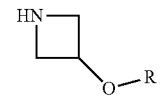

Step 1

A stock solution was made of N-Boc-3-hydroxyazetidine (532 mg) in THF (0.35M), followed by the addition of $PPh_3$ (808 mg) (or resin bound $PPh_3$) and DEAD (920 mg). An appropriate portion of this stock solution was added to a 2-dram round-bottom vial containing the appropriate phenol. The sealed vials were then shaken at RT for 48 h, then concentrated under reduced pressure.

Step 2

To each vial of crude N-Boc-azetidine was added $CH_2Cl_2$ (1 mL), followed by TFA (0.3 mL). The reaction mixtures were shaken at RT for 5 h, then concentrated under reduced pressure. The crude mixtures were each purified by catch and release using 2 g SCX-2 columns. The materials were loaded in MeOH, the column washed with MeOH, then with 2M $NH_3$ in MeOH. The basic wash was collected in new 15×75 round bottom vials and the solution dried overnight to afford the product.

The following 3-substituted alkoxyazetidines were prepared according to the general procedure in Reference B1:
3-(2-(trifluoromethoxy)phenoxy)azetidine
3-(3-chlorophenoxy)azetidine
3-(4-chloro-3-fluorophenoxy)azetidine
3-(2-chloro-4-(trifluoromethyl)phenoxy)azetidine
3-(3-ethylphenoxy)azetidine
3-(4-tert-butylphenoxy)azetidine
3-(m-tolyloxy)azetidine
3-(3-tert-butylphenoxy)azetidine
3-(2-chloro-5-methylphenoxy)azetidine
1-(4-(azetidin-3-yloxy)phenyl)-1H-imidazole
3-(4-cyclopentylphenoxy)azetidine
3-(2-chloro-4-methylphenoxy)azetidine
3-(2-fluoro-3-(trifluoromethyl)phenoxy)azetidine
3-(4-(trifluoromethylthio)phenoxy)azetidine
3-(2-fluoro-5-methylphenoxy)azetidine
3-(2,3-dichlorophenoxy)azetidine
3-(2,5-dichlorophenoxy)azetidine
3-(2,5-difluorophenoxy)azetidine
4-(azetidin-3-yloxy)-2-chlorobenzonitrile
3-(4-fluoro-2-methylphenoxy)azetidine
3-(3,4-dichlorophenoxy)azetidine
3-(2,4-difluorophenoxy)azetidine
3-(3,4-difluorophenoxy)azetidine
3-(4-chloro-3-methylphenoxy)azetidine
3-(4-chloro-2-methylphenoxy)azetidine
3-(4-methoxyphenoxy)azetidine

Reference B2

Synthesis of 3-substituted phenoxymethyl azetidine

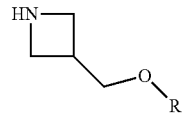

Step 1

A resealable vial was charged with tert-butyl 3-(hydroxymethyl)azetidine-1-carboxylate (200 mg, 1.07 mmol), THF (2 mL), triphenylphosphine (polymer-bound) (420 mg, 1.60 mmol), the appropriate phenol (1.60 mmol) and DEAD (252 μL, 1.60 mmol). The reaction vial was sealed and shaken at RT overnight. The polymer support was filtered off and washed with MeOH (10 mL). The filtrate was concentrated to afford a light yellow oil.

Step 2

The yellow oil was dissolved in $CH_2Cl_2$ (1 mL) and TFA (1 mL) was added. The reaction mixture was stirred at RT for 5 h. The crude mixtures were purified by catch and release using a 1 g SCX-2 column. The material was loaded in MeOH, the column washed with MeOH, then with 2M $NH_3$ in MeOH. The basic wash was collected, concentrated, and dried to afford the product.

The following 3-substituted phenoxymethyl azetidines were prepared according to the general procedure in Reference B2:

3-(phenoxymethyl)azetidine
3-((2-fluorophenoxy)methyl)azetidine
3-((3-fluorophenoxy)methyl)azetidine
3-((4-fluorophenoxy)methyl)azetidine
3-((2-(trifluoromethyl)phenoxy)methyl)azetidine
3-((3-(trifluoromethyl)phenoxy)methyl)azetidine
3-((2-chlorophenoxy)methyl)azetidine
3-((3-chlorophenoxy)methyl)azetidine
3-((4-(methylsulfonyl)phenoxy)methyl)azetidine
2-(azetidin-3-ylmethoxy)benzonitrile
3-(azetidin-3-ylmethoxy)benzonitrile
4-(azetidin-3-ylmethoxy)benzonitrile
3-((2-methoxyphenoxy)methyl)azetidine
3-((3-methoxyphenoxy)methyl)azetidine
3-((4-methoxyphenoxy)methyl)azetidine
3-((naphthalen-1-yloxy)methyl)azetidine
3-((naphthalen-2-yloxy)methyl)azetidine
3-((2-(trifluoromethoxy)phenoxy)methyl)azetidine
3-((3-(trifluoromethoxy)phenoxy)methyl)azetidine
3-((4-(trifluoromethoxy)phenoxy)methyl)azetidine
3-(3,5-dichlorophenoxy)azetidine
3-(4-chloro-3-methylphenoxy)azetidine
3-(4-(benzyloxy)phenoxy)azetidine
3-(4-isopropylphenoxy)azetidine
3-(2,3-dihydro-1H-inden-5-yloxy)azetidine
3-(2,4-dichlorophenoxy)azetidine
3-(2-methoxyphenoxy)azetidine
3-(biphenyl-2-yloxy)azetidine
3-(biphenyl-3-yloxy)azetidine
3-(4-methoxyphenoxy)azetidine
3-(2,3,4-trifluorophenoxy)azetidine
3-(2,6-dichlorophenoxy)azetidine
3-(3-ethynylphenoxy)azetidine
2-(4-(azetidin-3-yloxy)phenyl)acetonitrile
3-(3,4-dichlorophenoxy)azetidine
3-(4-chloro-2,6-difluorophenoxy)azetidine
3-(2-chloro-4-fluorophenoxy)azetidine
3-((4-chloro-3-(trifluoromethyl)phenoxy)methyl)azetidine
2-(azetidin-3-ylmethoxy)-5-chlorobenzamide
8-(azetidin-3-ylmethoxy)-5-chloroquinoline
3-((3,4-dichlorophenoxy)methyl)azetidine
3-((4-chloro-2-methylphenoxy)methyl)azetidine
3-((2,4-dichlorophenoxy)methyl)azetidine

Reference C

Synthesis of 3-(4-chloro-1,3,5-triazin-2-ylamino)-N-methylbenzamide

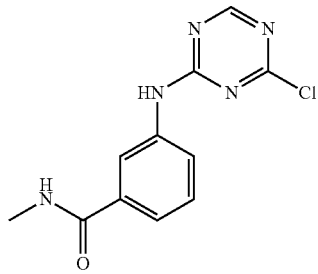 [SMILES: CNC(=O)c1cccc(Nc2ncnc(Cl)n2)c1]

2,4-Dichloro-1,3,5-triazine (6.99 g, 46.6 mmol) was dissolved in DMF (56.5 mL, 46.6 mmol) and the solution was cooled to 0° C. To this solution was added N-ethyl-N-isopropylpropan-2-amine (8.93 mL, 51.3 mmol) followed by the portionwise addition of 3-amino-N-methylbenzamide (7.00 g, 46.6 mmol). The resulting reaction mixture was allowed to slowly warm to room temperature and stirred for 4 hours. Water (about 800 mL) was added to the reaction mixture. A small amount of solid precipitated out of the solution at which point 100 mL of $CH_2Cl_2$ was added. The product was filtered off through a coarse Buchner funnel with the aid of water. After drying under vacuum, batch #1 of 3-(4-chloro-1,3,5-triazin-2-ylamino)-N-methylbenzamide was obtained (7.15 g, 58% yield) as a yellow solid. The filtrate was extracted with $CH_2Cl_2$ (3×100 mL). The organic layer was separated, dried over $MgSO_4$, filtered and concentrated, providing an additional batch of material (2.4 g, 20%) as yellow solid.

Reference D

Synthesis of 6-bromo-2-(4-chloro-1,3,5-triazin-2-yl)-1,2,3,4-tetrahydroisoquinoline

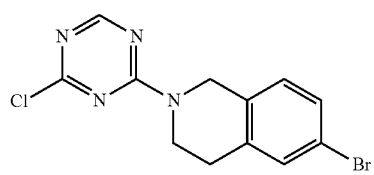 [SMILES: Clc1ncnc(N2CCc3cc(Br)ccc3C2)n1]

2,4-Dichloro-1,3,5-triazine (2.01 g, 12.7 mmol) was dissolved in 10 mL of dry DMF and the solution was cooled to 0° C. To this solution was added N,N-diisopropylethylamine, (6.65 mL, 38.2 mmol) and 6-bromo-1,2,3,4-tetrahydroisoquinoline hydrochloride (3.26 g, 12.7 mmol). The resulting reaction mixture was stirred at 0° C. to RT for 1.5 h. The reaction mixture was quenched with water (10 mL) and extracted with EtOAc. The organics were dried with MgSO$_4$, filtered and concentrated under reduced pressure. The crude material obtained was purified with medium pressure silica gel chromatography using gradient eluent, 0-40% EtOAc in hexanes to afford 6-bromo-2-(4-chloro-1,3,5-triazin-2-yl)-1,2,3,4-tetrahydroisoquinoline (1.90 g, 46% yield) as white solid.

Reference E

Synthesis of 4-(4-phenylthiazol-2-yl)piperidine

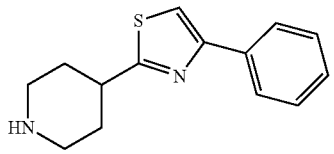 [SMILES: c1ccc(-c2csc(C3CCNCC3)n2)cc1]

To a flask charged with 2-bromoacetophenone (0.8 mL, 4092 μmol) and tert-butyl 4-carbamothioylpiperidine-1-carboxylate (1.00 g, 4092 μmol) was added EtOH (16 mL). The resulting solution was heated at reflux for 17 h under nitrogen. The resulting suspension was cooled to RT, dried under reduced pressure and purified using a 10 g SCX-2 column using methanol to transfer the material and wash the column and 2M NH$_3$ in MeOH to elute 4-(4-phenylthiazol-2-yl)piperidine (900 mg, 90%) obtained as a white solid upon drying of the basic wash.

The following amine was prepared according to the general procedure in Reference E
5-methyl-4-phenyl-2-(piperidin-4-yl)thiazole Reference F Synthesis of 6-cyclopropyl-1,2,3,4-tetrahydro-isoquinoline

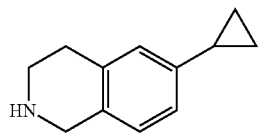 [SMILES: c1cc2c(cc1C1CC1)CCNC2]

Step 1
To an ice-cold solution of 4-bromo-benzaldehyde (10 g, 0.05 mol) and 2,2-dimethoxy-ethylamine (6.8 g, 0.06 mol) in MeOH (200 mL) was added AcOH (2 mL), and the reaction mixture was stirred at RT for 1 h. The reaction mixture was cooled to 0° C. and NaBH$_4$ (6.2 g, 0.15 mol) was added portionwise. The reaction mixture was stirred at RT for 10 h. After completion, The resulting reaction mixture was concentrated under reduced pressure and 10% aqueous NaOH was added. The mixture was extracted with EtOAc, the organic layer separated, dried over Na$_2$SO$_4$, and concentrated under reduced pressure. Purification was done by column chromatography using 100-200 mesh silica gel eluting with 5-15% EtOAc in hexanes to afford N-(4-bromobenzyl)-2,2-dimethoxyethanamine (10 g, 67%) as a pale yellow liquid.

Step 2
To a stirred solution of N-(4-bromobenzyl)-2,2-dimethoxyethanamine (10 g, 0.037 mol) in CH$_2$Cl$_2$ (100 mL) was added ClSO$_3$H (21.3 g, 0.18 mol) at −20° C. dropwise. The resulting reaction mixture was allowed to stir at 45° C. for 10 h. The resulting reaction mixture was diluted with CH$_2$Cl$_2$ and ice cold H$_2$O, then neutralized with aqueous NaHCO$_3$. The organic layer was separated and aqueous layer extracted with CH$_2$Cl$_2$. The combined organic layers were dried over Na$_2$SO$_4$ and concentrated at reduced pressure to get crude 6-bromoisoquinoline, which was purified by silica gel chromatography eluting with 5-15% EtOAc-hexanes to afford 6-bromoisoquinoline (0.9 g, 12%) as yellow liquid.

Step 3
To a degassed solution of 6-bromoisoquinoline (0.9 g, 0.004 mol) in 1,4-dioxane (15 mL) was added cyclopropylboronic acid (0.560 g, 0.007 mol) followed by the addition of degassed aqueous solution of K$_2$CO$_3$ (3.1 g, 0.02 mol) and PdCl$_2$(dppf) (0.190 g, 0.002 mol). The resulting reaction mixture was stirred at 110° C. for 10 h. After completion, the reaction mixture was filtered over Celite® (diatomaceous earth) and the filtrate was concentrated at reduced pressure to obtain crude 6-cyclopropylisoquinoline. Purification was done by silica gel column chromatography eluting with EtOAc in hexanes (10-30%) to afford pure 6-cyclopropylisoquinoline (0.500 g, 68%) as yellow liquid.

Step 4
To a solution of 6-cyclopropylisoquinoline (0.500 g, 0.003 mol) in EtOH (15 mL) was added indium powder (3 g) and saturated aqueous NH$_4$Cl (5 mL). The reaction mixture was heated at reflux for 36 h while stirring. After completion, the reaction mixture was filtered through Celite® (diatomaceous earth) and the filtrate concentrated at reduced pressure to afford crude 6-cyclopropyl-1,2,3,4-tetrahydro-isoquinoline. Purification was done by silica gel column chromatography eluting with MeOH in CH$_2$Cl$_2$ (0-10%) to afford pure 6-cyclopropyl-1,2,3,4-tetrahydro-isoquinoline (0.300 g, 58%) as a white solid.

Reference G

Synthesis of 4-(1,2,3,6-tetrahydropyridin-4-yl)benzonitrile-TFA

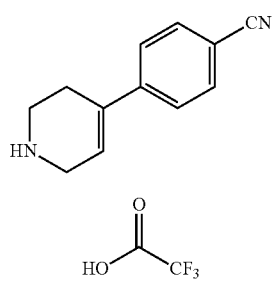 [SMILES: N#Cc1ccc(C2=CCNCC2)cc1 ; O=C(O)C(F)(F)F]

Step 1
To a 40 mL vial charged with tert-butyl 4-(4,4,5,5-tetramethyl-1,3,2-dioxaborolan-2-yl)-5,6-dihydropyridine-1(2H)-carboxylate (500.00 mg, 1617 μmol) was added dioxane (3.2 mL, 1617 μmol), Na$_2$CO$_3$ (3.234 mL, 647 μmol) and 4-bromobenzonitrile (294.3 mg, 1617 μmol). The reaction mixture was purged with nitrogen prior to the addition of PdCl$_2$(dppf)-CH$_2$Cl$_2$ (132.1 mg, 162 μmol). The reaction mixture was heated to 110° C. for 24 h. The dark reaction mixture was cooled to RT and water was added. The resulting reaction mixture was extracted with ethyl acetate, and the combined organics were washed with brine, dried with Na$_2$SO$_4$, filtered and concentrated under reduced pressure. The crude black oil was chromatographed ramping 0% EtOAc in hexanes to 25% over 5 min, then remaining at 5% for 15 min, then ramping to 100% over 5 min providing isolation of tert-butyl 4-(4-cyanophenyl)-5,6-dihydropyridine-1(2H)-carboxylate (390.00 mg, 84.8%).

Step 2

To a solution of tert-butyl 4-(4-cyanophenyl)-5,6-dihydropyridine-1(2H)-carboxylate (332 mg, 1168 μmol) in CH$_2$Cl$_2$ (4.00 mL, 62167 μmol) was added TFA (0.0900 mL, 1168 μmol). The yellow solution was stirred at RT for 3 h. The reaction mixture was dried under reduced pressure providing an off-white crystalline material 4-(1,2,3,6-tetrahydropyridin-4-yl)benzonitrile-TFA (305 mg, 87.6%). MS (ESI, pos. ion) m/z: 185.4 (M+1).

The following compounds were prepared as described in Reference G above using appropriate starting materials.
4-(4-(trifluoromethoxy)phenyl)-1,2,3,6-tetrahydropyridine
4-(3,4-dimethylphenyl)-1,2,3,6-tetrahydropyridine
4-(1,2,3,6-tetrahydropyridin-4-yl)-2-(trifluoromethoxy)benzonitrile Reference H Synthesis of 4-(4-(trifluoromethyl)phenyl)piperidine

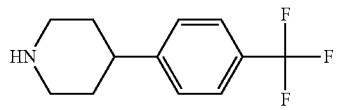 [SMILES: FC(F)(F)c1ccc(C2CCNCC2)cc1]

Step 1

To a stirred solution of 4-(4-trifluoromethyl-phenyl)-3,6-dihydro-2H-pyridine-1-carboxylic acid tert-butyl ester (2.5 g, 0.00783 mol) (prepared as described in Reference G above) in ethanol (23.0 mL) was added 10% Pd/C (826 mg, 0.00078 mol) under N$_2$ atmosphere and the mixture was allowed to stir at RT overnight under hydrogen atmosphere. The reaction mixture was filtered through cellite, washing with EtOAc (2×100 mL). The filtrate was concentrated under reduced pressure to obtain 4-(4-trifluoromethyl-phenyl)-piperidine-1-carboxylic acid tert-butyl ester (2 g, 80%).

Step 2

To a stirred solution of 4-(4-trifluoromethyl-phenyl)-piperidine-1-carboxylic acid tert-butyl ester (2.0 g, 0.0060 mol) in CH$_2$Cl$_2$ (19.0 mL), trifluoro acetic acid (3.46 g, 0.0303 mol) was added at 0° C. and the mixture was allowed to stir at RT overnight. CH$_2$Cl$_2$ and TFA were removed under reduced pressure and the crude product was filtered and washed with diethyl ether (2×20 mL) to obtain 4-(4-trifluoromethyl-phenyl)-piperidine trifluoro acetic acid salt with (1.58 g, 83%).

The following compounds were prepared as described in Reference H above using appropriate starting materials.
2,6-difluoro-4-(piperidin-4-yl)benzonitrile
4-(piperidin-4-yl)-3-(trifluoromethyl)benzonitrile
4-(piperidin-4-yl)benzonitrile
4-(4-(trifluoromethoxy)phenyl)piperidine
4-(piperidin-4-yl)-3-(trifluoromethoxy)benzonitrile
2,3-difluoro-4-(piperidin-4-yl)benzonitrile
4-(piperidin-4-yl)-2-(trifluoromethoxy)benzonitrile
4-(4-chlorophenyl)piperidine Reference I Synthesis of 4-(4-(trifluoromethoxy)benzyloxy)piperidine

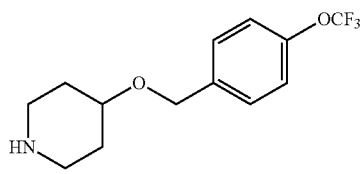 [SMILES: FC(F)(F)Oc1ccc(COC2CCNCC2)cc1]

Step 1

To a dried flask charged with tert-butyl 4-hydroxypiperidine-1-carboxylate (3.60 g, 17887 μmol) was added dry DMF (40 mL) and the resulting solution cooled in an ice water bath prior to the addition of NaH (60% in mineral oil) (748 mg, 18781 μmol) in two portions 5 min apart. The reaction mixture was stirred for 1 hr and allowed to warm to RT over that time. The resulting suspension was cooled in an ice water bath prior to the addition of a solution of 1-(bromomethyl)-4-(trifluoromethoxy)benzene (5018 mg, 19676 μmol) in DMF (5 mL) via syringe. The resulting reaction mixture was allowed to slowly warm to RT while stirring for 15 h. The resulting pale yellow suspension was carefully diluted with water (about 150 mL) and extracted 2× with EtOAc. The combined organics were dried with Na$_2$SO$_4$, filtered and concentrated under reduced pressure. The material was purified through silica gel column chromatography ramping ethyl acetate in hexanes from 0% to 10% over 5 mins, then remaining at 10% for 10 min, then ramping to 50% over 5 min providing tert-butyl 4-(4-(trifluoromethoxy)benzyloxy)-piperidine-1-carboxylate (5 g) as a white crystalline solid upon drying.

Step 2 tert-Butyl 4-(4-(trifluoromethoxy)benzyloxy)piperidine-1-carboxylate was dissolved in CH$_2$Cl$_2$ (40 mL) and TFA (4 mL) was added. The light yellow solution was stirred at RT for 20 h, after which time complete Boc deprotection was evident by LC-MS. The solution was concentrated under reduced pressure providing product as a TFA salt in 65-95% overall yield. The material was purified to obtain a salt or free based using catch and release with strong cation exchange chromatography (SCX-2) washing first with MeOH, then with 2M NH$_3$ in MeOH.

The following compounds were prepared as described in Reference I above using appropriate starting materials.
4-(3-(trifluoromethyl)benzyloxy)piperidine
4-(4-(trifluoromethyl)benzyloxy)piperidine
4-(3-(trifluoromethoxy)benzyloxy)piperidine
4-(3,4-difluorobenzyloxy)piperidine Reference J Synthesis of 4-(2-(methylsulfonyl)phenoxy)piperidine hydrochloride

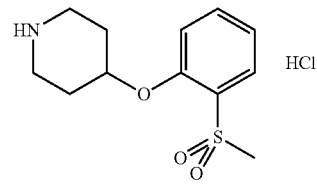 [SMILES: CS(=O)(=O)c1ccccc1OC1CCNCC1 ; Cl]

Step 1

To a stirred solution of 2-methanesulfonyl-phenol (2 g, 11.61 mmol) in THF (20 mL) 4-hydroxy-piperidine-1-carboxylic acid tert-butyl ester (2.57 g, 12.77 mmol) was added followed by $PPh_3$ (6.7 g, 25.54 mmol). The resulting reaction mixture was stirred at RT for 15 min. DEAD (4.5 g, 25.54 mmol) was added dropwise at 20° C. and the reaction mixture was stirred at RT for 18 h. After completion of the reaction (monitored by TLC, visualized by UV or ninhydrin), the mixture was concentrated under reduced pressure to obtain the crude material, which was further diluted with $CH_2Cl_2$ (50 mL). The $CH_2Cl_2$ layer was washed with water (3×100 mL) then dried over $Na_2SO_4$, filtered and concentrated under reduced pressure to obtain the crude material, which was further purified through silica gel column chromatography, using 8% EtOAc in hexanes to afford 4-(2-methanesulfonyl-phenoxy)-piperidine-1-carboxylic acid tert-butyl ester (2.6 g, 87%).

Step 2

To 4-(2-methanesulfonyl-phenoxy)-piperidine-1-carboxylic acid tert-butyl ester (2.6 g, 7.3 mmol) was added HCl in dioxane solution (4M) (15 mL). The reaction mixture was stirred at RT for 5 h. After completion of the reaction (monitored by TLC), the excess dioxane was removed in vacuo affording an off white solid. The crude material was washed with diethyl ether (3×20 mL) to afford 4-(2-(methylsulfonyl)phenoxy)piperidine hydrochloride (1.3 g, 80.7%).

The following compounds were prepared as described in Reference J above using appropriate starting materials.
4-(4-chlorophenoxy)piperidine
4-(4-(2,2,2-trifluoroethoxy)phenoxy)piperidine
4-(4-chloro-3-fluorophenoxy)piperidine
4-(3-(trifluoromethoxy)phenoxy)piperidine
4-(4-chloro-3-(trifluoromethoxy)phenoxy)piperidine
4-(3-chlorophenoxy)piperidine
4-(2-(trifluoromethoxy)phenoxy)piperidine
4-(4-fluoro-3-(trifluoromethoxy)phenoxy)piperidine
4-(3-fluorophenoxy)piperidine
4-(2-fluorophenoxy)piperidine
4-(4-(trifluoromethyl)phenoxy)piperidine
4-(4-(trifluoromethoxy)phenoxy)piperidine
4-(2-chlorophenoxy)piperidine Reference K Synthesis of 2-phenyl-4-(piperidin-4-yl)thiazole

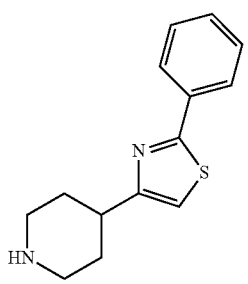 [SMILES: c1ccc(-c2nc(C3CCNCC3)cs2)cc1]

Step 1

To a stirred solution of piperidine-1,4-dicarboxylic acid mono-(9H-fluoren-9-ylmethyl) ester (5 g, 14.2 mmol) in $CH_2Cl_2$ (50 mL) was added DMF (0.5 mL) and the resulting solution was cooled to 0° C. To this solution oxalyl chloride (3.6 g, 28.44 mmol) was added dropwise and the reaction mixture was stirred at RT for 16 h. The reaction mixture was concentrated under reduced pressure to afford (9H-fluoren-9-yl)methyl 4-(chlorocarbonyl)-piperidine-1-carboxylate (5 g, 95%) as brown liquid.

Step 2

To a stirred solution of (9H-fluoren-9-yl)methyl 4-(chlorocarbonyl)piperidine-1-carboxylate (5 g, 13.6 mmol) in toluene at 0° C. was added TMS-diazomethane (30 mL). This reaction mixture was stirred at RT for 16 h. The reaction mixture was concentrated under reduced pressure to afford of (9H-fluoren-9-yl)methyl 4-(diazoacetyl)piperidine-1-carboxylate (5 g, 98%) as dark brown liquid.

Step 3

A solution of (9H-fluoren-9-yl)methyl 4-(diazoacetyl)piperidine-1-carboxylate (5 g, 13.3 mmol) in THF was cooled in an ice water bath and was treated with an aqueous HBr solution (10 mL). This reaction mixture was stirred at RT for 2 h. The reaction mixture was diluted with water and the organic content was extracted using EtOAc, dried over $Na_2SO_4$, filtered and concentrated at reduced pressure. The crude product was chromatographed over silica gel eluting with a gradient (0-15% EtOAc:hexanes) to afford (9H-fluoren-9-yl)methyl 4-(bromoacetyl)piperidine-1-carboxylate (3 g, 53%) as an off white solid.

Step 4

To a stirred solution of (9H-fluoren-9-yl)methyl 4-(bromoacetyl)piperidine-1-carboxylate (3 g, 7.03 mmol) in EtOH (20 mL) was added thiobenzamide (0.96 g, 7.03 mmol). This reaction mixture was stirred at RT for 24 h. $NaHCO_3$ (3 g) was added and the reaction mixture was further stirred for 5 d. The reaction mixture was concentrated to afford the crude material which was chromatographed over silica gel eluting with a gradient (0-10% EtOAc:hexanes) to afford (9H-fluoren-9-yl)methyl 4-(2-phenylthiazol-4-yl)piperidine-1-carboxylate (2 g, 61%) as an off white solid.

Step 5

To a stirred solution of (9H-fluoren-9-yl)methyl 4-(2-phenylthiazol-4-yl)piperidine-1-carboxylate (2 g, 4.29 mmol) in $CH_2Cl_2$:MeOH (15:5 mL) was added piperidine (5 mL). This reaction mixture was stirred at RT for 8 h. The reaction mixture was concentrated under reduced pressure and the crude material was chromatographed over silica gel eluting with a gradient (0-10% MeOH:$CH_2Cl_2$) to afford 2-phenyl-4-(piperidin-4-yl)thiazole (1 g, 96%) as an off white solid.

Reference L

Synthesis of 1-phenyl-4,5,6,7-tetrahydro-1H-pyrazolo[4,3-c]pyridine

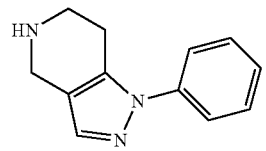 [SMILES: c1ccc(-n2ncc3c2CCNC3)cc1]

Step 1

DMF dimethyl acetal (5.82 mL, 0.044 mol) was added to a stirred solution of tert-butyl 4-oxopiperidine-1-carboxylate (8.73 g, 0.044 mol) in DMF (80 mL) and the reaction mixture was heated to 80° C. under $N_2$ for 18 h. After cooling, the DMF was removed under reduced pressure and the residue was partitioned between EtOAc and $H_2O$. The organic layer was washed with $H_2O$ and saturated brine, then dried over MgSO₄ and evaporated to afford tert-butyl 3-((dimethylamino)methylene)-4-oxopiperidine-1-carboxylate (8.44 g, 76%).

Step 2 tert-Butyl 3-((dimethylamino)methylene)-4-oxopiperidine-1-carboxylate (2.1 g, 8.3 mmol) was dissolved in MeOH (100 mL), and water (50 mL) was added followed by the addition of sodium carbonate (0.53 g, 5.0 mmol) and phenyl hydrazine hydrochloride (1.43 g, 9.9 mmol). Finally, acetic acid (1 mL) was added and the resulting reaction mixture was stirred at RT for 1 h. The reaction mixture was made basic by adding saturated aqueous sodium bicarbonate (ca. 20 mL) and the MeOH was removed under reduced pressure. The resulting reaction mixture was extracted with CH₂Cl₂ (3×40 mL) and the combined extracts were dried over anhydrous sodium sulfate, filtered, and concentrated to afford the crude product. Purification by flash chromatography on silica gel using 20% EtOAc in hexanes as the eluent afforded 1-phenyl-4,5,6,7-tetrahydro-1H-pyrazolo[4,3-c]pyridine (1.63 g, 66%) as a yellow oil.

The following compound was prepared as described in Reference L above using appropriate starting materials.

1-(4-chlorophenyl)-4,5,6,7-tetrahydro-1H-pyrazolo[4,3-c]pyridine

Reference M

Synthesis of 5-ethyl-2,3,4,5-tetrahydro-1H-pyrido[4,3-b]indole

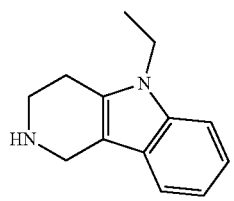

Step 1

1-Benzyl-4-piperidone (1 mmol) was added dropwise to a stirred suspension of phenyl hydrazine (1 equiv.) in a solution of 7% H₂SO₄ (20 mL) in 1,4-dioxane (20 mL). The reaction mixture was heated at reflux for 18 h then cooled to RT. The solvent was evaporated and the residue recrystallized to afford 2-benzyl-2,3,4,5-tetrahydro-1H-pyrido[4,3-b]indole (95%).

Step 2

To a suspension of 2-benzyl-2,3,4,5-tetrahydro-1H-pyrido[4,3-b]indole and NaH (1.1 equiv.) in DMF (10 mL) was added at 0° C., ethyl iodide (1 mmol) and stirred at RT overnight. The reaction mixture was quenched with a sat. solution of NH₄Cl and extracted with EtOAc. The combined organic extracts were dried over anydrous Na₂SO₄ and purified by flash chromatography to afford 2-benzyl-5-ethyl-2,3,4,5-tetrahydro-1H-pyrido[4,3-b]indole (85%).

Step 3

2-Benzyl-5-ethyl-2,3,4,5-tetrahydro-1H-pyrido[4,3-b]indole (1 g) was dissolved in EtOH (10 mL), treated with 10% Pd/C (150 mg) and stirred under an atmosphere of hydrogen at RT. The reaction mixture was filtered through Celite® (diatomaceous earth) and concentrated. Purification by flash chromatography (10% MeOH/CH₂Cl₂) afforded 5-ethyl-2,3,4,5-tetrahydro-1H-pyrido[4,3-b]indole (90%) as a viscous oil.

Reference O

Synthesis of 2-phenyl-4,5,6,7-tetrahydrofuro[3,2-c]pyridine

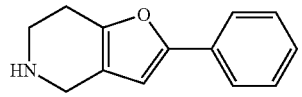

Step 1

To a solution of 1-benzylpiperidin-4-one (10.0 g, 0.0529 mmol) and morpholine (6.9 g, 0.079 mol) in dry benzene was added a catalytic amount of PTSA (450 mg, 0.00262 mol). A round bottom flask was attached with a Dean Stark assembly then the reaction mixture was heat at reflux under nitrogen for 17 to 18 h. The reaction mixture was concentrated under a nitrogen atmosphere, then the crude mixture was diluted with dry benzene and cooled to 0° C. and a solution of phenacyl bromide (12.63 g, 0.0634 mol) in benzene was added. The reaction mixture was allowed to warm to RT and stirred overnight. The reaction mixture was diluted with water and stirred at RT for 1 h, then extracted with EtOAc (300×3 mL), dried over Na₂SO₄ and concentrated to afford the crude product which was purified by flash chromatography (eluent: 10% EtOAc/hexanes) to afford 1-benzyl-3-(2-oxo-2-phenylethyl)-piperidin-4-one (4.5 g, 45.0%).

Step 2

A solution of 1-benzyl-3-(2-oxo-2-phenylethyl)piperidin-4-one (4.0 g, 0.0129 mol) in conc. HCl (50 mL) was heated at reflux for 3 h. After consumption of the starting material as determined by TLC, the reaction mixture was cooled down to RT and made alkaline by the addition of NH₄OH, then extracted with diethyl ether. The organics were dried over Na₂SO₄ and concentrated to afford 5-benzyl-2-phenyl-4,5,6,7-tetrahydrofuro[3,2-c]pyridine (2.0 g, 66.66%) as a white solid.

Step 3

To a solution of 5-benzyl-2-phenyl-4,5,6,7-tetrahydrofuro [3, 2-c]pyridine (1.5 g, 0.00649 mol) in EtOH (30 mL) under nitrogen was added Pd—C(10%) (200 mg, 0.3 mmol). Hydrogen (1 atm) was applied and the reaction mixture was stirred for 3 to 4 h at RT. After consumption of starting materials as determined by TLC, the reaction mixture was filtered through Celite® (diatomaceous earth), washing with EtOH. The filtrate was concentrated to afford a solid which was washed with ether to afford 2-phenyl-4,5,6,7-tetrahydrofuro[3,2-c]pyridine (620 mg, 48%).

Reference P

Synthesis of 3-((4-chlorobenzyloxy)methyl)azetidine 2,2,2-trifluoroacetate

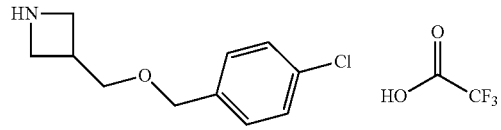 [SMILES: Clc1ccc(COCC2CNC2)cc1 ; O=C(O)C(F)(F)F]

tert-Butyl 3-(hydroxymethyl)azetidine-1-carboxylate (75 mg, 0.400 mmol) was dissolved in THF (2.5 mL) and potassium tert-butoxide (0.049 g, 0.440 mmol) was added. The reaction mixture was allowed to stir at RT for 1 h, then 1-(bromomethyl)-4-chlorobenzene (82 mg, 0.400 mmol) was added. The reaction mixture was allowed to stir at RT overnight then concentrated to remove THF. CH$_2$Cl$_2$ (2 mL) was added, followed by TFA. The reaction mixture was allowed to stir at RT for 48 h then concentrated to afford crude 3-((4-chlorobenzyloxy)methyl)azetidine 2,2,2-trifluoroacetate, which was used without purification.

The following compound was prepared as described in Reference P above using appropriate starting materials.

3-((4-(trifluoromethyl)benzyloxy)methyl)azetidine 2,2,2-trifluoroacetate

Reference Q

Synthesis of 5-amino-2-hydroxy-N-methylbenzamide

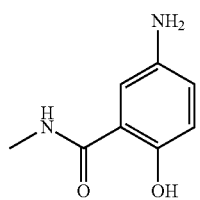

To a flask charged with 2-(benzyloxy)-N-methyl-5-nitrobenzamide (176 mg, 1.061 mmol) was added MeOH (4 mL). The resulting suspension was thoroughly purged with nitrogen prior to the addition of 10% Pd/C (12 mg, 0.046 mmol). The reaction mixture was purged with H$_2$ gas, and then stirred under at atmosphere of hydrogen overnight. The reaction mixture was filtered through Celite® (diatomaceous earth) and the filtrate dried under reduced pressure. The resulting 5-amino-2-hydroxy-N-methylbenzamide (90 mg, 99% crude yield) was used in next step without further purification.

Reference R

Synthesis of 2-phenyl-4-(1,2,3,6-tetrahydropyridin-4-yl)thiazole

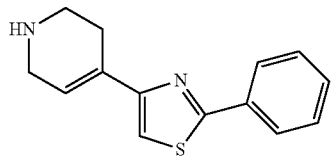 [SMILES: C1=C(c2csc(-c3ccccc3)n2)CCNC1]

Step 1

To a vial charged with 4-bromo-2-chlorothiazole (250 mg, 1.260 mmol) was added phenylboronic acid (154 mg, 1.260 mmol) followed by dioxane (2.5 mL) and sodium carbonate (2M aqueous) (2.5 mL, 1.260 mmol). The reaction mixture was purged with argon prior to the addition of PdCl$_2$(dppf)-CH$_2$Cl$_2$ (103 mg, 0.126 mmol). The reaction mixture was heated to 40° C. for 5 h, then tert-butyl 4-(tert-butoxy(ethoxy)boryl)-5,6-dihydropyridine-1(2H)-carboxylate (392 mg, 1.260 mmol) was added and heating continued overnight at 100° C.

The vessel was diluted with water and extracted with CH$_2$Cl$_2$. The combined organics were dried with Na$_2$SO$_4$, filtered and dried under reduced pressure.

Step 2

The material obtained was dissolved in CH$_2$Cl$_2$ (4 mL) and TFA (1 mL) was added. The reaction mixture was stirred over the weekend at RT leading to the Boc cleavage product as the major LC-MS species. The dark solution was dried under reduced pressure and purified with a 5 g SCX-2 column washing with MeOH followed by 2M NH$_3$ in MeOH to elute basic materials. Upon drying 101 mg of 2-phenyl-4-(1,2,3,6-tetrahydropyridin-4-yl)thiazole was obtained with about 70% purity. This material was used without further purification.

Reference S

Synthesis of 4-phenyl-2-(1,2,3,6-tetrahydropyridin-4-yl)thiazole

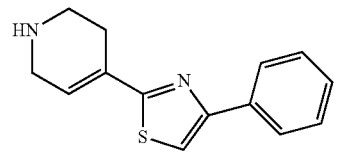 [SMILES: C1=C(c2nc(-c3ccccc3)cs2)CCNC1]

Step 1

To a vial charged with 4-bromo-2-chlorothiazole (0.957 g, 4.82 mmol), and tert-butyl 4-(tert-butoxy(ethoxy)boryl)-5,6-dihydropyridine-1(2H)-carboxylate (1.5 g, 4.82 mmol) was added dioxane (9.64 mL), sodium carbonate (2M aqueous) (9.64 mL, 4.82 mmol) and PdCl$_2$(dppf)-CH$_2$Cl$_2$ (0.394 g, 0.482 mmol). The reaction mixture was placed under a blanket of argon and sealed (Teflon® (polytetrafluoroethlene) twist cap) and heated at 40° C. for 4 h.

The reaction mixture was diluted with water and extracted with CH$_2$Cl$_2$ (2×). The combined organics were dried with Na$_2$SO$_4$, filtered and concentrated under reduced pressure. The crude residue was purified by flash chromatography ramping ethyl acetate in hexanes from 0% to 25%, then isocratic at 25% providing tert-butyl 4-(4-bromothiazol-2-yl)-5,6-dihydropyridine-1(2H)-carboxylate (1.100 g, 3.19 mmol, 66.1% yield) as a light yellow solid.

Step 2

To a suspension of tert-butyl 4-(4-bromothiazol-2-yl)-5,6-dihydropyridine-1(2H)-carboxylate (300 mg, 0.869 mmol) in dioxane (869 µL) was added 2M Na$_2$CO$_3$ (869 µL) followed by phenylboronic acid (106 mg, 0.869 mmol) and Pd(PPh$_3$)$_4$ (100 mg, 0.087 mmol). The reaction mixture was stirred overnight at 100° C.

The reaction mixture was cooled to RT, diluted with water, transferred to a reparatory funnel and extracted with EtOAc (2×). The combined organics were dried with Na$_2$SO$_4$, filtered and dried under reduced pressure and purified by flash chromatography ramping ethyl acetate in hexanes from 0 to 25%, then isocratic at 25% EtOAc to afford tert-butyl 4-(4-phenylthiazol-2-yl)-5,6-dihydropyridine-1(2H)-carboxylate (206 mg, 0.602 mmol, 69.2% yield, about 15% impurity).

Step 3

To a solution of tert-butyl 4-(4-phenylthiazol-2-yl)-5,6-dihydropyridine-1(2H)-carboxylate (206 mg, 0.602 mmol) in CH$_2$Cl$_2$ (2.4 mL) was added TFA (0.232 mL). The solution turned bright red immediately, and after stirring overnight the color had become orange. The solution was concentrated under reduced pressure and the crude oil obtained purified with a 5 g SCX-2 column washing first with MeOH, then with 2M NH$_3$ in MeOH leading to elution of basic materials. Upon drying, 4-phenyl-2-(1,2,3,6-tetrahydropyridin-4-yl)thiazole (121 mg, 0.499 mmol, 83%) was obtained as a yellow oil.

Reference T

Synthesis of 3-(4-(trifluoromethoxy)phenoxy)pyrrolidine

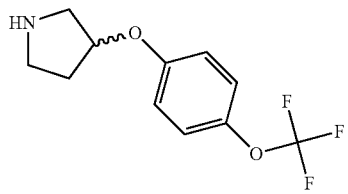 [SMILES: FC(F)(F)Oc1ccc(OC2CCNC2)cc1]

Step 1

To a flask charged with tert-butyl 3-hydroxypyrrolidine-1-carboxylate (250 mg, 1.335 mmol) was added DCE (5.3 mL) followed by 4-(trifluoromethoxy)phenol (173 µL, 1.335 mmol), triphenylphosphine (350 mg, 1.335 mmol) and (E)-di-tert-butyl diazene-1,2-dicarboxylate (307 mg, 1.335 mmol) respectively. The resulting yellow/orange solution was stirred at RT overnight providing a light yellow solution.

The solution was dried under reduced pressure and the crude oil obtained purified with flash chromatography ramping ethyl acetate in hexanes from 0 to 25%, then isocratic at 25% providing a broad peak which contained product along with about 25% impurity according to NMR. The material, tert-butyl 3-(4-(trifluoromethoxy)phenoxy)pyrrolidine-1-carboxylate (335 mg, 0.965 mmol, 72.2%), was used without further purification.

Step 2

To a solution of tert-butyl 3-(4-(trifluoromethoxy)phenoxy)pyrrolidine-1-carboxylate (325 mg, 0.936 mmol) in CH$_2$Cl$_2$ (3.7 mL) was added TFA (360 µL, 4.68 mmol). The colorless solution was dried under reduced pressure and the crude oil obtained purified with a 5 g SCX-2 column washing first with MeOH, then with 2M NH$_3$ in MeOH leading to elution of basic materials to afford 3-(4-(trifluoromethoxy)-phenoxy)pyrrolidine (190 mg, 0.769 mmol, 82% yield).

Reference U

Synthesis of 4-(phenylethynyl)piperidine

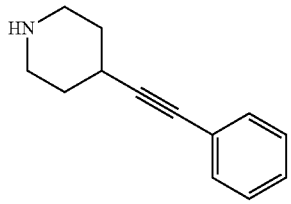 [SMILES: C(#CC1CCNCC1)c1ccccc1]

Step 1

To a solution of 4-ethynyl-piperidine-1-carboxylic acid tert-butyl ester (5.0 g, 23.0 mmol) and iodobenzene (5.8 g, 28.6 mmol) in triethylamine (25 ml) was added catalytic amount of CuI. The mixture was purged with N$_2$ for 0.5 h. To the reaction mixture was added Pd(PPh$_3$)$_4$ (0.260 g, 0.023 mmol) and the mixture was purged with N$_2$ gas for 0.5 h. The reaction mixture was stirred at 90° C. overnight then concentrated under reduced pressure. The crude material was diluted with water and extracted with ethyl acetate. The organic layer was concentrated to give crude product, which was purified by silica gel chromatography EtOAc in hexanes (0-20%) to give 4-ethynyl-piperidine-1-carboxylic acid tert-butyl ester (5 g, 73.5%) product.

Step 2

To a solution of 4-ethynyl-piperidine-1-carboxylic acid tert-butyl ester (5 g) in methanol (10 mL) was added methanolic HCl (25 mL). The reaction mixture was stirred for overnight then concentrated under reduced pressure to provide a white solid. The crude product was washed with ether and filtered to give 4-(phenylethynyl)piperidine (3.5 g, 92.1%) as a white solid.

Reference V

Synthesis of 1-ethylspiro[indoline-3,4'-piperidin]-2-one

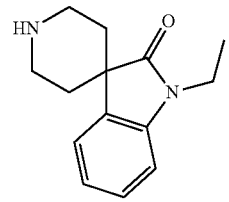 [SMILES: CCN1C(=O)C2(CCNCC2)c2ccccc21]

Step 1

To a stirred solution of 1,3-dihydro-indol-2-one (11.4 g, 0.0856 mol) in THF (260 mL), NaHMDS (1M soln in THF, 428 mL, 0.428 mol) was added at −78° C. The reaction mixture was stirred for 30 min then bis-(2-chloro-ethyl)-methyl-amine (16.0 g, 0.102 mol) in THF (minimum amount) was added dropwise for 30 min at −78° C. and the reaction mixture was allowed to stir at RT overnight. The reaction mixture was quenched with water (100 mL) and extracted with EtOAc (2×200 mL). The organic portions were combined, dried over Na$_2$SO$_4$, filtered and evaporated under reduced pressure. The crude product was purified by column chromatography using silica gel and 0-6% MeOH:DCM as a eluent to obtain 1.8 g of 1,2-benzo-8-methyl-3,8-diazaspiro[4,5]decan-4-one (10%).

Step 2

To a stirred solution of 1,2-benzo-8-methyl-3,8-diazaspiro[4,5]decan-4-one (0.0092 mol) in DMF (21 mL), K$_2$CO$_3$ (1.92 g, 0.013 mol) was added at 0° C. and the reaction mixture was allowed to stir at RT for 10 min. Ethyl iodide (1.73 g, 0.0111 mol) was added at RT and the reaction mixture was stirred at RT overnight. Completion of the reaction was determined by TLC. The reaction mixture was diluted with EtOAc (2×40 mL) and washed with water (2×20 mL). The organic portions were combined and dried over Na$_2$SO$_4$ and evaporated under reduced pressure. The crude material was washed with EtOAc: Pentane (2:8) to obtain 1-ethyl-1'-methylspiro[indoline-3,4'-piperidin]-2-one (74%).

Step 3

To a stirred solution of 1-ethyl-1'-methylspiro[indoline-3,4'-piperidin]-2-one (0.0046 mol) in toluene (41.6 mL) was added 2,2,2 trichloro ethyl chloroformate (6.23 mL, 0.046 mol) at 0° C. and the reaction mixture was heated at reflux for 18 h. Progress of the reaction was monitored by TLC. The reaction mixture was cooled to RT, diluted with EtOAc (2×50 mL) and washed with water (2×12 mL) and brine (12 mL). The organic portions were combined, dried over Na$_2$SO$_4$ and evaporated under reduced pressure. The crude product was taken up in acetic acid (12.0 mL) and Zn (4.1 g, 0.062 mol) and was added portion wise at 0° C. The reaction mixture was allowed to stir at RT for 1 h. Progress of the reaction was monitored by TLC. The reaction mixture was filtered through Celite® (diatomaceous earth) and washed with EtOAc (2×20 mL), basified using saturated NH₄OH solution (15.0 mL) and extracted with DCM (2×40 mL). the organic portions were combined, dried over Na₂SO₄ and evaporated under reduced pressure to obtain crude 1-ethylspiro[indoline-3,4'-piperidin]-2-one (42%).

Reference W

Synthesis of 3-(1-(4-chlorophenoxy)ethyl)azetidine

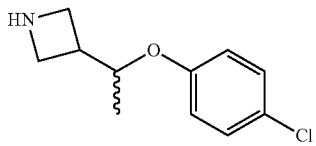

Step 1

To a flask charged with tert-butyl 3-(1-hydroxyethyl)azetidine-1-carboxylate (212 mg, 1.053 mmol) was added THF (6.3 mL), resin bound PPh₃ (527 mg, 1.580 mmol), p-chlorophenol (104 µL, 1.053 mmol) and DEAD (250 µL, 1.580 mmol). The reaction mixture was stirred overnight at RT. The reaction mixture was filtered through cotton and dried under reduced pressure, then purified with flash chromatography ramping CH₂Cl₂:MeOH:NH₄OH (90:10:1) in CH₂Cl₂ from 0% to 100% to afford tert-butyl 3-(1-(4-chlorophenoxy)ethyl)-azetidine-1-carboxylate (145 mg, 44%) as a yellow oil.

Step 2

To a flask charged with tert-butyl 3-(1-(4-chlorophenoxy)ethyl)azetidine-1-carboxylate (140 mg, 0.449 mmol) was added CH₂Cl₂ (1796 µL) followed by TFA (242 µL, 3.14 mmol). The reaction mixture was stirred at RT for 72 h. The yellow solution was dried under reduced pressure and purified with a 2 g SCX-2 column loading and washing with MeOH, then washing with 2M NH₃ in MeOH to afford 3-(1-(4-chlorophenoxy)ethyl)azetidine (57 mg, 0.269 mmol, 60.0% yield, about 10% impurity present) as a light pink oil.

Reference X

Synthesis of 3-(4-chlorophenyl)-5,6,7,8-tetrahydro-[1,2,4]triazolo[4,3-a]pyrazine

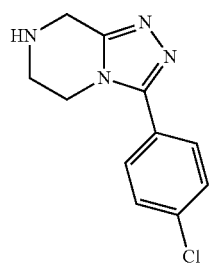 [SMILES: Clc1ccc(-c2nnc3n2CCNC3)cc1]

Step 1

To 2-hydrazinopyrazine (1.60 g, 14.55 mmol) was added 4-chloro-benzoic acid (3 eq) followed by 20 mL of polyphosphoric acid, and the reaction mixture was stirred at 110° C. for 18 h. The hot PPA solution was added to ice and neutralized by the addition of ammonium hydroxide (highly exothermic!). The aqueous solution was extracted with ethyl acetate, washed with brine, and dried over anhydrous sodium sulfate. Concentration followed by flash chromatography (silica gel, 1:1 hexanes: ethyl acetate) afforded 3-(4-chlorophenyl)-[1,2,4]triazolo[4,3-a]pyrazine, as a viscous oil.

Step 2

3-(4-Chlorophenyl)-[1,2,4]triazolo[4,3-a]pyrazine (2.01 g) was hydrogenated under atmospheric hydrogen with 10% Pd/C (400 mg Celite® (diatomaceous earth)) as a catalyst in ethanol (20 mL) at RT for 18 h. The reaction mixture was filtered through and concentrated. Purification by flash chromatography (silica gel, 10% methanol/dichloromethane) afforded 3-(4-chlorophenyl)-5,6,7,8-tetrahydro-[1,2,4]triazolo[4,3-a]pyrazine (86% yield) as a viscous oil.

Reference Y

Synthesis of 5-(2,2,2-trifluoroethoxy)-1,2,3,4-tetrahydroisoquinoline 2,2,2-trifluoroacetate

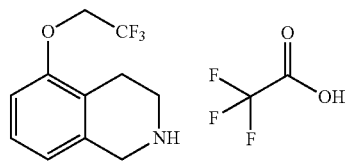

Step 1

To a resealable tube was added tert-butyl 5-hydroxy-3,4-dihydroisoquinoline-2(1H)-carboxylate (200 mg, 0.802 mmol) and cesium carbonate (601 mg, 1.845 mmol) in DMF (2 mL) followed by 2,2,2-trifluoroethyl trifluoromethanesulfonate (1005 mg, 4.33 mmol). The reaction mixture stirred at 70° C. overnight. The crude material was purified by reverse-phase preparative HPLC using 0.1% TFA in CH₃CN/H₂O, gradient 55% to 95% over 10 min to provide tert-butyl 5-(2,2,2-trifluoroethoxy)-3,4-dihydroisoquinoline-2(1H)-carboxylate (120 mg) as colorless oil.

Step 2

5-(2,2,2-Trifluoroethoxy)-3,4-dihydroisoquinoline-2(1H)-carboxylate (120 mg) was dissolved in DCM (6 mL) followed by addition of TFA (2 mL). The reaction mixture was stirred at RT for 20 min. The reaction solvent was removed under reduced pressure and the residue was dried on high vacuum overnight to yield 5-(2,2,2-trifluoroethoxy)-1,2,3,4-tetrahydroisoquinoline 2,2,2-trifluoroacetate (125 mg) as a colorless oil which was used without purification.

Reference Z

Synthesis of 3-amino-N-phenylbenzamide

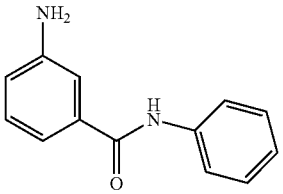 [SMILES: Nc1cccc(C(=O)Nc2ccccc2)c1]

HATU (230 mg, 0.605 mmol) and aniline (0.063 mL, 0.691 mmol) was added to a solution of 3-aminobenzoic acid hydrochloride (100 mg, 0.576 mmol) and N,N-diisopropylethylamine (0.217 mL, 1.267 mmol) in 1.5 mL of DMF. The reaction solution was stirred at RT for 3 h. The crude material was purified by reverse-phase preparative HPLC using 0.1% TFA in CH₃CN/H₂O, gradient 20% to 45%. Desired fractions were collected and the solvents were removed under reduced pressure. The residue was passed through 2 g SCX column and washed by 2M NH3 in MeOH to provide 3-amino-N-phenylbenzamide (42 mg, 0.198 mmol, 34.4% yield) as a light-yellow solid.

The following compounds were prepared according to general procedure in Reference Z above using appropriate starting materials.
3-amino-N-(2-methoxyethyl)benzamide
N-methyl-3-(methylamino)benzamide

Example 1

Synthesis of 3-(4-(4-(3,4-dimethylphenyl)piperazin-1-yl)-1,3,5-triazin-2-ylamino)-2-methylbenzamide

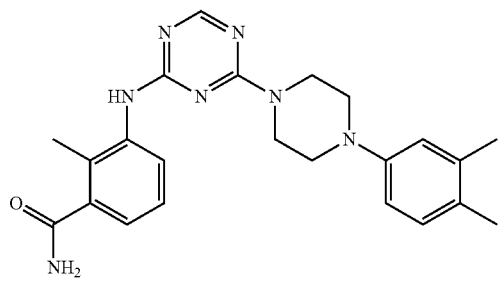 [SMILES: Cc1ccc(N2CCN(c3ncnc(Nc4cccc(C(N)=O)c4C)n3)CC2)cc1C]

To a solution of 2,4-dichloro-1,3,5-triazine (50.0 mg, 0.333 mmol) in DMF (1334 µL, 0.333 mmol) was added N-ethyl-N-isopropylpropan-2-amine (174 µL, 1.000 mmol). The reaction mixture was cooled in an ice-water bath prior to the addition of 3-amino-2-methylbenzamide (50.1 mg, 0.333 mmol). The reaction mixture was stirred for 1 h at 0° C. at which time LC-MS revealed complete conversion to 3-(4-chloro-1,3,5-triazin-2-ylamino)-2-methylbenzamide. To this yellow solution was added 1-(3,4-dimethylphenyl)piperazine (63.4 mg, 0.333 mmol). The reaction mixture was allowed to stir and warm slowly to RT over 3 h. Water was added yielding a precipitate, which was filtered off, washed with water, and then purified further by reverse phase liquid chromatography using TFA as a modifier. Fractions containing the product were combined and washed with sat. NaHCO$_3$. The product was extracted with CH$_2$Cl$_2$. The organic phase was washed with brine, dried over MgSO$_4$, filtered, and concentrated to afford 3-(4-(4-(3,4-dimethyl-phenyl)piperazin-1-yl)-1,3,5-triazin-2-ylamino)-2-methylbenzamide (78 mg, 0.187 mmol, 56.0% yield) was obtained as a white solid.

Example 2

Synthesis of 3-(4-(4-hydroxypiperidin-1-yl)-1,3,5-triazin-2-ylamino)-N-methylbenzamide

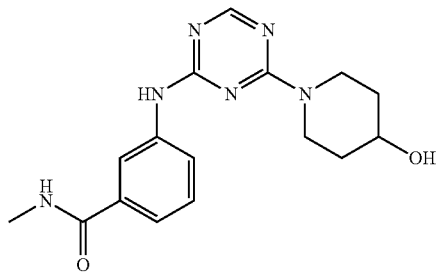 [SMILES: CNC(=O)c1cccc(Nc2ncnc(N3CCC(O)CC3)n2)c1]

3-(4-Chloro-1,3,5-triazin-2-ylamino)-N-methylbenzamide (200 mg, 0.758 mmol) was dissolved in DMF (3034 µL, 0.758 mmol) at RT. To this solution was added N-ethyl-N-isopropylpropan-2-amine (145 µL, 0.834 mmol) and piperidin-4-ol (77 mg, 0.758 mmol). The resulting mixture was stirred at RT for 1 h, at which time LCMS showed mainly product. The reaction mixture was passed through an SCX-2 column with MeOH. The product was then eluted with 2.0 M NH$_3$ in MeOH. After concentration, the crude was purified further by medium pressure silica gel chromatography using 60:40 CH$_2$Cl$_2$:(90:10:1 CH$_2$Cl$_2$:MeOH:NH$_4$OH) as the eluent to afford 3-(4-(4-hydroxypiperidin-1-yl)-1,3,5-triazin-2-ylamino)-N-methylbenzamide (200 mg, 0.609 mmol, 80%) as a white solid.

Example 3

Synthesis of 3-(4-(6-bromo-3,4-dihydroisoquinolin-2(1H)-yl)-1,3,5-triazin-2-ylamino)-2-methylbenzamide

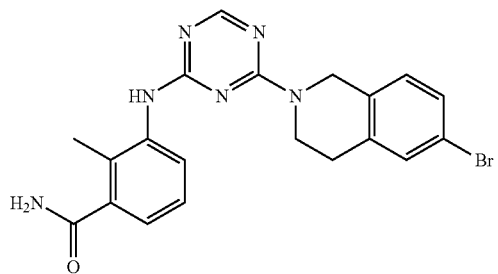 [SMILES: Cc1c(Nc2ncnc(N3CCc4cc(Br)ccc4C3)n2)cccc1C(N)=O]

To a vial charged with 6-bromo-2-(4-chloro-1,3,5-triazin-2-yl)-1,2,3,4-tetrahydroisoquinoline (163 mg, 499 µmol) and 3-amino-2-methylbenzamide (75 mg, 499 µmol) was added N-ethyl-N-isopropylpropan-2-amine (174 µl, 999 µmol) and propan-2-ol (1665 µl, 499 µmol). The vial was sealed and heated to 95° C. overnight. The product was purified by reverse phase liquid chromatography using TFA as a modifier. Fractions containing the product were combined and neutralized with saturated NaHCO$_3$ (35 mL). The product was extracted with DCM (3×30 mL). The organics were separated, dried over Na$_2$SO$_4$, and filtered to afford 3-(4-(6-bromo-3,4-dihydroisoquinolin-2(1H)-yl)-1,3,5-triazin-2-ylamino)-2-methylbenzamide (55 mg, 25%) as a white solid upon drying.

Example 4

Synthesis of 3-(4-(3-(4-chlorophenoxy)propylamino)-1,3,5-triazin-2-ylamino)-N-methylbenzamide

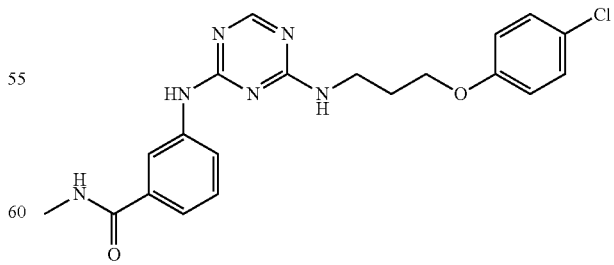

Step 1

To a solution of 2,4-dichloro-1,3,5-triazine (0.300 g, 2.000 mmol) in DMF (6670 µL) was added N-ethyl-N-isopropylpropan-2-amine (1048 µL, 6.000 mmol). The reaction vessel was cooled in an ice-water bath prior to the addition of 3-amino-N-methylbenzamide (300 mg, 2.000 mmol). The reaction mixture was stirred for 3 h at 0° C. at which time LC-MS revealed complete conversion to the desired chlorotriazine intermediate. To this yellow solution was added 3-aminopropan-1-ol (150 mg, 2.000 mmol). The reaction mixture was allowed to stir and warm slowly to RT over 18 h. Solids had precipitated out of the solution. The solid was filtered off, washed with water, and very little methanol to obtain 3-(4-(3-hydroxypropylamino)-1,3,5-triazin-2-ylamino)-N-methylbenzamide (516 mg, 1.707 mmol, 85%) as a white solid.

Step 2

To a microwave vial charged 3-(4-(3-hydroxypropylamino)-1,3,5-triazin-2-ylamino)-N-methylbenzamide (0.112 g, 0.370 mmol) was added dichloroethane (4 mL), triphenylphosphine (0.146 g, 0.556 mmol), p-chlorophenol (0.095 g, 0.741 mmol)) and DEAD (0.129 g, 0.741 mmol) respectively. The reaction mixture was irradiated in the microwave at 130° C. for 30 min. The reaction mixture was concentrated under reduced pressure and purified with flash chromatography using $CH_2Cl_2$:MeOH:$NH_4OH$ (90:10:1) in $CH_2Cl_2$ to afford 3-(4-(3-(4-chlorophenoxy)propylamino)-1,3,5-triazin-2-ylamino)-N-methylbenzamide (30 mg, 20%) as a white solid.

Example 5

Synthesis of 3-(4-(2,8-diazaspiro[4.5]decan-8-yl)-1,3,5-triazin-2-ylamino)-N-methylbenzamide as a bis-TFA salt

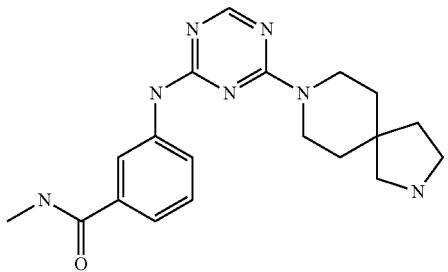 [SMILES: CNC(=O)c1cccc(Nc2ncnc(N3CCC4(CCNC4)CC3)n2)c1]

To a flask charged with tert-butyl 8-(4-(3-(methylcarbamoyl)phenylamino)-1,3,5-triazin-2-yl)-2,8-diazaspiro[4.5]decane-2-carboxylate (300 mg, 0.642 mmol) was added DCM (5 mL), and TFA (494 mL, 6.42 mmol) respectively. The resulting mixture was stirred overnight at RT. The reaction mixture was concentrated, and the resulting solid was triturated with ethyl acetate to obtain 3-(4-(2,8-diazaspiro[4.5]decan-8-yl)-1,3,5-triazin-2-ylamino)-N-methylbenzamide as a bis-TFA salt (233 mg, 99% yield) as white solid.

Example 6

Synthesis of 3-(6-(3-(4-fluorophenoxy)azetidin-1-yl)pyridin-2-ylamino)-N-methylbenzamide

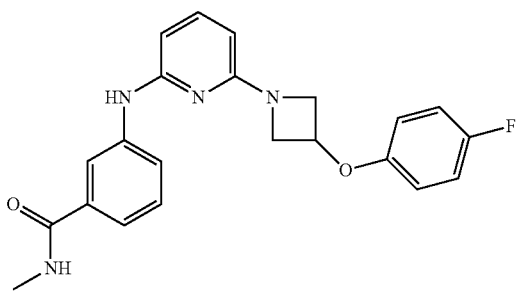 [SMILES: CNC(=O)c1cccc(Nc2cccc(N3CC(Oc4ccc(F)cc4)C3)n2)c1]

Step 1

To 2-bromo-6-fluoropyridine (150.0 mg, 0.852 mmol) in 2-propanol (3.00 mL) at RT was added N-ethyl-N-isopropylpropan-2-amine (0.445 mL, 2.56 mmol) followed by 3-(4-fluorophenoxy)azetidine hydrochloride (174 mg, 0.852 mmol). The resulting reaction mixture was stirred at RT for 3.5 h, then heated to 70° C. for 24 h, cooled to RT and concentrated. Purification of the crude product using MPLC (5 g cartridge, 12 g column, 0 to 60% EtOAc-hexanes) gave 2-bromo-6-(3-(4-fluorophenoxy)azetidin-1-yl)pyridine (211.4 mg).

Step 2

To a disposable sealed tube was charged 2-bromo-6-(3-(4-fluorophenoxy)azetidin-1-yl)pyridine (100.0 mg, 0.309 mmol), 3-amino-N-methylbenzamide (69.7 mg, 0.464 mmol), potassium carbonate (59.9 mg, 0.433 mmol) followed by X-Phos (2.95 mg, 6.19 μmol) and $Pd_2(dba)_3$ (1.417 mg, 1.547 μmol). The tube was fitted with a septum with an argon inlet for 5-10 min, when t-BuOH (1.0 mL) was added. The reaction mixture was then heated to 100° C. for 7 h, cooled to RT, diluted with EtOAc, and filtered through Celite® (diatomaceous earth) with EtOAc. The filtrate was concentrated and purified using MPLC (5 g cartridge, 12 g column, 0 to 75% EtOAc-hexanes) giving 3-(6-(3-(4-fluorophenoxy)azetidin-1-yl)pyridin-2-ylamino)-N-methylbenzamide (112.8 mg).

Example 7

Synthesis of 3-(4-(3-(4-fluorophenoxy)azetidin-1-yl)pyridin-2-ylamino)-N-methylbenzamide

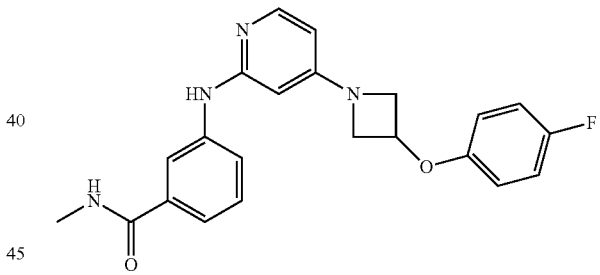

Step 1

To 2-chloro-4-fluoropyridine (160.0 mg, 1.216 mmol) and 3-(4-fluoro-phenoxy)-azetidine hydrochloride (248 mg, 1.216 mmol) in 2-propanol (3.0 mL) in a disposable sealed tube at RT was added N-ethyl-N-isopropylpropan-2-amine (0.530 mL, 3.04 mmol). The resulting reaction mixture was heated at 84° C. for 18 h, cooled to RT, concentrated, purified using MPLC (5 g cartridge, 12 g column, 0 to 60% EtOAc-hexanes) giving 2-chloro-4-(3-(4-fluorophenoxy)azetidin-1-yl)pyridine (306.1 mg).

Step 2

To 2-chloro-4-(3-(4-fluorophenoxy)azetidin-1-yl)pyridine (90 mg, 0.323 mmol) and 3-amino-N-methylbenzamide (72.7 mg, 0.484 mmol) in 2-propanol (3.00 mL) in a disposable sealed tube at RT was added trifluoroacetic acid, (0.075 mL, 0.969 mmol). The resulting reaction mixture was heated at 84° C. for 5 days and 92° C. for 20 days, cooled to RT, concentrated, purified using MPLC (5 g cartridge, 12 g column, 0 to 100% 90/10 $CH_2Cl_2$-MeOH in $CH_2Cl_2$) giving 3-(4-(3-(4-fluorophenoxy)azetidin-1-yl)pyridin-2-ylamino)-N-methylbenzamide (73.6 mg).

Example 8

Synthesis of 3-(4-(3-(4-fluorophenoxy)azetidin-1-yl)pyrimidin-2-ylamino)-N-methylbenzamide

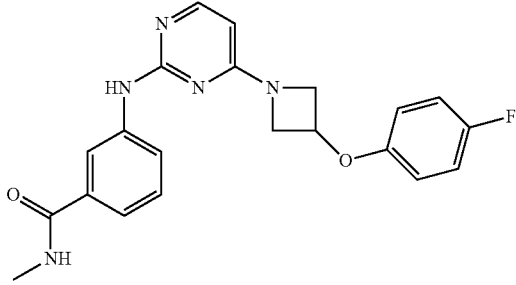 [SMILES: CNC(=O)c1cccc(Nc2nccc(N3CC(Oc4ccc(F)cc4)C3)n2)c1]

Step 1

To 2,4-dichloropyrimidine (200.0 mg, 1.342 mmol) in 2-propanol (7 mL) at 0° C. was added N-ethyl-N-isopropylpropan-2-amine (0.702 mL, 4.03 mmol) followed by 3-(4-fluorophenoxy)azetidine hydrochloride (273 mg, 1.342 mmol). The resulting reaction mixture was stirred at 0° C. for 10 min then at RT for 41 h and concentrated. Purification of the crude product was done using MPLC (25 g cartridge, 40 g column, 0 to 60% EtOAc-hexanes) to give 2-chloro-4-(3-(4-fluorophenoxy)azetidin-1-yl)pyrimidine (314.2 mg).

Step 2

To 2-chloro-4-(3-(4-fluorophenoxy)azetidin-1-yl)pyrimidine (90.0 mg, 0.322 mmol) and 3-amino-N-methylbenzamide (53.2 mg, 0.354 mmol) in a disposable sealed tube in 2-propanol (2.50 mL) was added trifluoroacetic acid (0.074 mL, 0.965 mmol). The resulting reaction mixture was heated at 84° C. for 18 h, cooled to RT, concentrated, taken up in MeOH-DCM, filtered through an SCX-2 column with MeOH. The product was eluted with 2.0 M $NH_3$ in MeOH. Fractions containing the product were concentrated to afford 3-(4-(3-(4-fluorophenoxy)azetidin-1-yl)pyrimidin-2-ylamino)-N-methylbenzamide (123.9 mg).

The following compound was prepared as described in Example 8 above using appropriate starting materials.
3-(4-(3-(4-chlorophenoxy)azetidin-1-yl)pyrimidin-2-ylamino)-N-methylbenzamide; and

Example 9

Synthesis of 3-(5-cyano-2-(3-(4-fluorophenoxy)azetidin-1-yl)pyrimidin-4-ylamino)-N-methylbenzamide

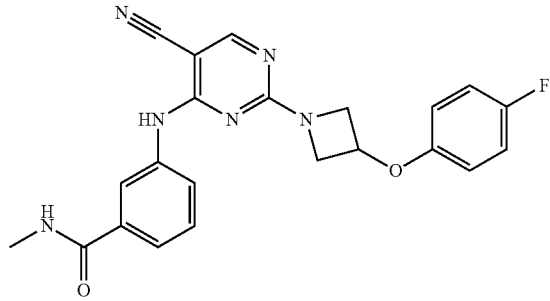

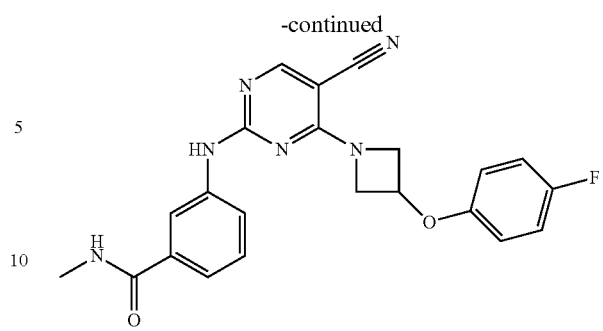

Step 1

To 3-amino-N-methylbenzamide (353 mg, 2.351 mmol) in DME (8 mL) at 0° C. was added N-ethyl-N-isopropylpropan-2-amine (1.024 mL, 5.88 mmol) followed by 2,4-dichloropyrimidine-5-carbonitrile (450.0 mg, 2.59 mmol). The resulting reaction mixture was allowed to warm to RT (ice melt) over 3 h, concentrated, purified using MPLC (25 g cartridge, 40 g column, 0 to 100% EtOAc-hexanes). Separation of 2- and 4-substitution products was not achieved. Fractions with both products were combined and concentrated giving about a 3:1 mixture of 3-(2-chloro-5-cyanopyrimidin-4-ylamino)-N-methylbenzamide and 3-(4-chloro-5-cyanopyrimidin-2-ylamino)-N-methylbenzamide (172.7 mg).

Step 2

To the reaction mixture of 3-(2-chloro-5-cyanopyrimidin-4-ylamino)-N-methylbenzamide and 3-(4-chloro-5-cyanopyrimidin-2-ylamino)-N-methylbenzamide (172.7 mg, 0.600 mmol) and 3-(4-fluorophenoxy)azetidine hydrochloride (128 mg, 0.631 mmol) in a disposable sealed tube at RT was added 2-propanol (4 mL) followed by N,N-diisopropylethylamine (0.314 mL, 1.802 mmol). The resulting reaction mixture was heated to 84° C. for 4.5 h, cooled to RT, concentrated, adsorbed onto silica gel, purified using MPLC (25 g cartridge about 20% full, 40 g column, 0 to 80% 90/10 $CH_2Cl_2$-MeOH in $CH_2Cl_2$) giving 3-(5-cyano-4-(3-(4-fluorophenoxy)azetidin-1-yl)pyrimidin-2-ylamino)-N-methylbenzamide (19.3 mg) and 3-(5-cyano-2-(3-(4-fluorophenoxy)azetidin-1-yl)pyrimidin-4-ylamino)-N-methylbenzamide (13.2 mg).

Example 10

Synthesis of 3-(5-fluoro-4-(3-(4-fluorophenoxy)azetidin-1-yl)pyrimidin-2-ylamino)-N-methylbenzamide

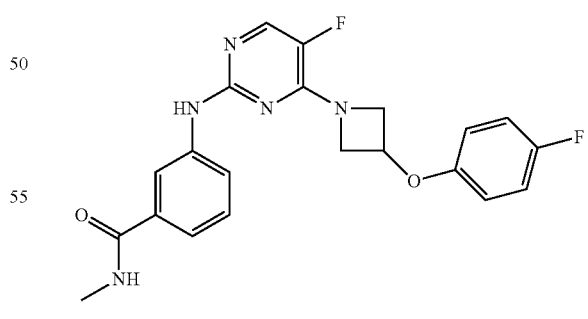

Step 1

To a solution 2,4-dichloro-5-fluoropyrimidine (150.0 mg, 0.898 mmol) in 2-propanol (4.00 mL) at RT was added N-ethyl-N-isopropylpropan-2-amine (0.469 mL, 2.70 mmol) followed by 3-(4-fluorophenoxy)azetidine hydrochloride (183 mg, 0.898 mmol). The resulting reaction mixture was stirred at RT for 1 h and concentrated. Purification of the crude using MPLC (25 g cartridge, 40 g column, 0 to 60% EtOAc-hexanes) gave 2-chloro-5-fluoro-4-(3-(4-fluorophenoxy)azetidin-1-yl)pyrimidine (240.6 mg).

Step 2

To 2-chloro-5-fluoro-4-(3-(4-fluorophenoxy)azetidin-1-yl)pyrimidine (90.0 mg, 0.302 mmol) and 3-amino-N-methylbenzamide (49.9 mg, 0.333 mmol) in a disposable sealed tube in 2-propanol (2.50 mL) was added trifluoroacetic acid (0.070 mL, 0.907 mmol). The resulting reaction mixture was heated at 84° C. for 3 d, cooled to RT and concentrated. The residue was stirred in EtOAc and saturated aqueous NaHCO$_3$ for 10 min and transferred to a reparatory funnel. The organic layer was washed with brine, dried and concentrated giving 3-(5-fluoro-4-(3-(4-fluorophenoxy)azetidin-1-yl)pyrimidin-2-ylamino)-N-methylbenzamide (124.8 mg).

Example 11

Synthesis of 3-(6-(3-(4-fluorophenoxy)azetidin-1-yl)pyrimidin-4-ylamino)-N-methylbenzamide

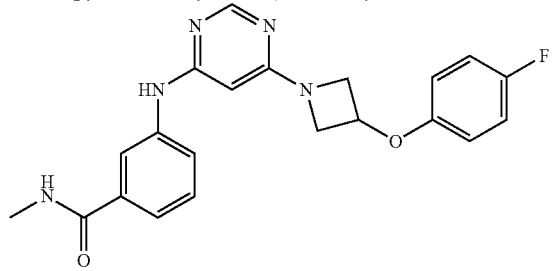

Step 1

To 4,6-dichloropyrimidine (500.0 mg, 3.36 mmol) and 3-amino-N-methylbenzamide (504 mg, 3.36 mmol) in 2-propanol (5.00 mL) at RT was added N,N-diisopropylethylamine (0.877 mL, 5.03 mmol). The resulting reaction mixture was heated at 80° C. for 3 days, cooled to RT, concentrated, purified using MPLC (25 g cartridge, 40 g column, 0 to 100% EtOAc-hexanes then 30-100% 90:10 CH$_2$Cl$_2$-MeOH in CH$_2$Cl$_2$). Fractions with product were combined and concentrated giving 3-(6-chloropyrimidin-4-ylamino)-N-methylbenzamide (815.2 mg).

Step 2

To 3-(6-chloropyrimidin-4-ylamino)-N-methylbenzamide (90.0 mg, 0.343 mmol) and 3-(4-fluorophenoxy)azetidine hydrochloride (73.3 mg, 0.360 mmol) in a disposable sealed tube at RT was added 2-propanol (2 mL) followed by N,N-diisopropylethylamine (0.179 mL, 1.028 mmol). The resulting reaction mixture was heated at 84° C. for 51 h, cooled to RT, concentrated, purified using MPLC (5 g cartridge, 12 g column, 0 to 65% 90/10 CH$_2$Cl$_2$-MeOH in CH$_2$Cl$_2$) giving 3-(6-(3-(4-fluorophenoxy)azetidin-1-yl)pyrimidin-4-ylamino)-N-methylbenzamide (135.0 mg).

Example 12

Synthesis of 3-(2-(3-(4-fluorophenoxy)azetidin-1-yl)pyrimidin-4-ylamino)-N-methylbenzamide

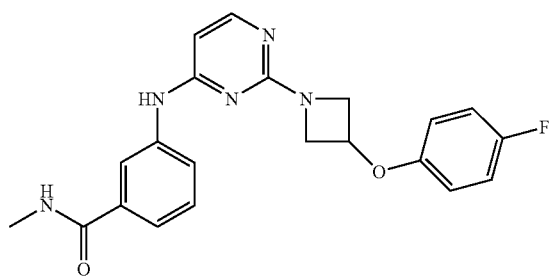 [SMILES: CNC(=O)c1cccc(Nc2ccnc(N3CC(Oc4ccc(F)cc4)C3)n2)c1]

Step 1

To 2,4-dichloropyrimidine (250.0 mg, 1.678 mmol) and 3-amino-N-methylbenzamide (252 mg, 1.678 mmol) in 2-propanol (8390 µL) in a disposable sealed tube at RT was added N-ethyl-N-isopropylpropan-2-amine (585 µL, 3.36 mmol). The resulting reaction mixture was heated at 60° C. for 22 h, then to 70° C. for 23 h, then 80° C. for 3 days, cooled to RT, concentrated, purified using MPLC (5 g cartridge, 12 g column, 0 to 60% 90/10 CH$_2$Cl$_2$-MeOH in CH$_2$Cl$_2$) giving 3-(2-chloropyrimidin-4-ylamino)-N-methylbenzamide (389.0 mg).

Step 2

To 3-(2-chloropyrimidin-4-ylamino)-N-methylbenzamide (90.0 mg, 0.343 mmol) and 3-(4-fluorophenoxy)azetidine hydrochloride (73.3 mg, 0.360 mmol) in a disposable sealed tube in 2-propanol (2.00 mL) was added N-ethyl-N-isopropylpropan-2-amine (0.179 mL, 1.028 mmol). The resulting reaction mixture was heated at 84° C. for 48 h, cooled to RT, filtered, rinsed with IPA, and concentrated under reduced pressure to afford 3-(2-(3-(4-fluorophenoxy)azetidin-1-yl)pyrimidin-4-ylamino)-N-methylbenzamide (102.3 mg).

The following compounds were prepared as described in Example 12 above using appropriate starting materials:

3-(2-(3-(4-chlorophenoxy)azetidin-1-yl)pyrimidin-4-ylamino)-N-methylbenzamide; and 3-(2-(3-((4-chlorophenoxy)methyl)azetidin-1-yl)pyrimidin-4-ylamino)-N-methylbenzamide.

Example AAA 3-(4-(3-(2,4-dichlorophenoxy)azetidin-1-yl)pyrimidin-2-ylamino)-N-methylbenzamide

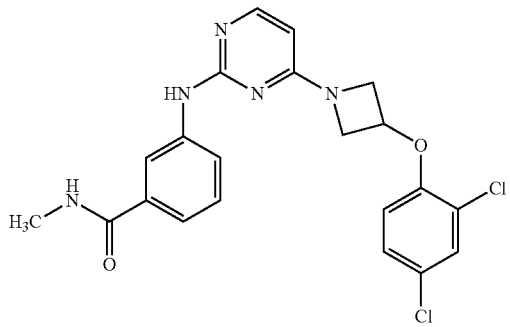 [SMILES: CNC(=O)c1cccc(Nc2nccc(N3CC(Oc4ccc(Cl)cc4Cl)C3)n2)c1]

Step 1

To a solution of tert-butyl 3-hydroxycyclobutanecarboxylate (1.0 g, 5.77 mmol) in CH$_2$Cl$_2$ (18 mL) was added triethylamine (1.2 mL, 8.66 mmol). After stirring for 10 min at 0° C., tosylchloride (1.2 g, 6.35 mmol) was added and the reaction mixture was stirred at RT for another 12 h. The mixture was quenched with water and extracted with CH$_2$Cl$_2$ (2×20 mL). The organic extracts were washed with brine, dried over anhydrous sodium sulfate and concentrated under reduced pressure. Purification by silica gel column chromatography provided tert-butyl 3-(tosyloxy)azetidine-1-carboxylate (0.700 g, 40%) as solid. Observed mass (M+1): 328.

Step 2

To a solution of tert-butyl 3-(tosyloxy)azetidine-1-carboxylate (1.0 g, 3.05 mmol) and 2,4-dichlorophenol (0.490 g, 3.05 mmol) in DMF (10 mL) was added potassium carbonate (0.630 g, 4.67 mmol) and the reaction mixture was heated to 120° C. for 2 h. Then reaction was quenched with water and extracted with EtOAc (2×25 mL). The organic extracts were washed with brine, dried over anhydrous sodium sulfate and concentrated under reduced pressure. Purification by silica gel column chromatography provided tert-butyl 3-(2,4-dichlorophenoxy)azetidine-1-carboxylate (1.2 g, 63%) as a solid.

Step 3

To a solution of tert-butyl 3-(2,4-dichlorophenoxy)azetidine-1-carboxylate (1.2 g, 3.78 mmol) in $CH_2Cl_2$ (10 mL) was added trifluoroacetic acid (TFA) (7 mL) and the reaction mixture was stirred at RT for 2 h. The mixture was concentrated under reduced pressure and filtered, washing with chloroform followed by diethyl ether to obtain 3-(2,4-dichlorophenoxy) azetidine (0.800 g, 100%) as a TFA salt.

Step 4

To a solution of 3-(2,4-dichlorophenoxy)azetidine (1.0 g, 4.6 mmol) in isopropanol (14 mL) was added N,N-diisopropylethylamine (DIPEA) (1.0 mL, 6.9 mmol) and 2,4-dichloropyrimidine (0.686 g, 4.6 mmol and the reaction mixture was heated at 80° C. for 7 h. The mixture was concentrated under reduced pressure and extracted with EtOAc (2×20 mL) and water (2×20 mL). The organic extracts were washed with brine, dried over anhydrous sodium sulfate and concentrated under reduced pressure. Purification by silica gel column chromatography provided 2-chloro-4-(3-(2,4-dichlorophenoxy)azetidin-1-yl)pyrimidine (0.600 g, 40%) as a solid. Observed mass (M+1): 330.0

Step 5

To a solution of 2-chloro-4-(3-(2,4-dichlorophenoxy)azetidin-1-yl)pyrimidine (0.200 g, 609 mmoL) and 4-amino-N-methylbenzamide (0.109 g, 0.731 mmoL) in dimethyl acetamide (5 mL) was added cesium carbonate (300 mg, 9.14 mmol) and the reaction mixture was degassed for 15 min. Tris(dibenzylideneacetone)dipalladium (0) [Pd$_2$(dba)$_3$] (0.030 g, 0.03 mmoL) and 2,2'-bis(diphenylphosphino)-1,1'-binaphthyl [BINAP] (0.020 g, 0.03 mmoL) were added and the mixture was irradiated in the microwave at 120° C. for 1 h. Then the reaction was quenched with water and extracted with EtOAc (2×25 mL). The organic extracts were washed with brine, dried over anhydrous sodium sulfate and concentrated under reduced pressure. Purification by silica gel column chromatography provided 4-(4-(3-(2,4-dichlorophenoxy)azetidin-1-yl)pyrimidin-2-ylamino)-N-methylbenzamide (0.077 g, 29%) as solid. Observed mass (M+1): 443.9.

The following compounds were prepared as described in Example AAA above using appropriate starting materials.

Example A
3-(4-(3-(3,4-dichlorophenoxy)azetidin-1-yl)pyrimidin-2-ylamino)-N-methylbenzamide Example B
N-methyl-3-((4-(3-(4-methylphenoxy)-1-azetidinyl)-2-pyrimidinyl)amino)benzamide Example C
N-methyl-3-((4-(3-(4-(trifluoromethyl)phenoxy)-1-azetidinyl)-2-pyrimidinyl)amino)benzamide Example D
3-((4-(3-(4-methoxyphenoxy)-1-azetidinyl)-2-pyrimidinyl)amino)-N-methylbenzamide Example E
3-((4-(3-(3,4-difluorophenoxy)-1-azetidinyl)-2-pyrimidinyl)amino)-N-methylbenzamide Example F
3-((4-(3-(3-chloro-4-fluorophenoxy)-1-azetidinyl)-2-pyrimidinyl)amino)-N-methylbenzamide Example G
3-((4-(3-(4-fluoro-3-methylphenoxy)-1-azetidinyl)-2-pyrimidinyl)amino)-N-methylbenzamide Example H
3-((4-(3-(2,4-difluorophenoxy)-1-azetidinyl)-2-pyrimidinyl)amino)-N-methylbenzamide Example I
3-((4-(3-(2-chloro-4-fluorophenoxy)-1-azetidinyl)-2-pyrimidinyl)amino)-N-methylbenzamide Example J
3-((4-(3-(4-fluoro-2-methylphenoxy)-1-azetidinyl)-2-pyrimidinyl)amino)-N-methylbenzamide Example K
3-((4-(3-(4-chloro-3-fluorophenoxy)-1-azetidinyl)-2-pyrimidinyl)amino)-N-methylbenzamide Example L
3-((4-(3-(4-chloro-3-methylphenoxy)-1-azetidinyl)-2-pyrimidinyl)amino)-N-methylbenzamide Example M
3-((4-(3-(4-chloro-2-fluorophenoxy)-1-azetidinyl)-2-pyrimidinyl)amino)-N-methylbenzamide Example N
3-((4-(3-(4-chloro-2-methylphenoxy)-1-azetidinyl)-2-pyrimidinyl)amino)-N-methylbenzamide Example O
3-((4-(3-((4-chlorophenoxy)methyl)-1-azetidinyl)-2-pyrimidinyl)amino)-N-methylbenzamide Example P
N-methyl-3-((4-(3-((4-methylphenoxy)methyl)-1-azetidinyl)-2-pyrimidinyl)amino)benzamide Example Q 3-(4-(3-(4-chloro-2-fluorophenoxy)azetidin-1-yl)-1,3,5-triazin-2-ylamino)-N-methylbenzamide

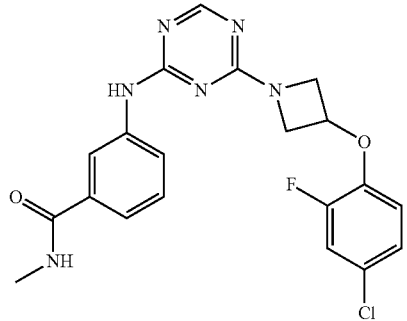 [SMILES: CNC(=O)c1cccc(Nc2ncnc(N3CC(Oc4ccc(Cl)cc4F)C3)n2)c1]

Step 1

To a solution of 3-(4-chloro-2-fluorophenoxy) azetidine (3.6 g, 18.0 mmol) in acetonitrile (60 mL, 3 mL/mmol) was added TEA (7.2 mL, 50.0 mmol) and 2, 4-dichloro-1, 3, 5-triazine (3.0 g, 20.0 mmol) and the reaction mixture was stirred at RT for 1 h. The reaction mixture was concentrated under reduced pressure and extracted with EtOAc (2×50 mL). The organic extracts were washed with brine, dried over anhydrous sodium sulfate and concentrated under reduced pressure. Purification by silica gel column chromatography provided 2-chloro-4-(3-(4-chloro-2-fluorophenoxy)azetidin-1-yl)-1,3,5-triazine (0.800 g, 20%) as a solid. Observed mass (M+1): 315.0

Step 2

To a solution of 2-chloro-4-(3-(4-chloro-2-fluorophenoxy) azetidin-1-yl)-1,3,5-triazine (0.800 g, 2.54 mmol) in Isopropanol (8 mL) was added DIPEA (0.7 mL, 3.81 mmol) and 3-amino-N-methylbenzamide (0.382 g, 2.54 mmol) and the reaction mixture was stirred at 80° C. for 24 h. The mixture was concentrated under reduced pressure and extracted with EtOAc (2×40 mL). The organic extracts were washed with brine, dried over anhydrous sodium sulfate and concentrated under reduced pressure. Purification by silica gel column chromatography to obtain 3-(4-(3-(4-chloro-2-fluorophenoxy)azetidin-1-yl)-1,3,5-triazin-2-ylamino)-N-methylbenzamide (0.527 g, 53%) as a solid. Observed mass (M+1): 428.9

Example R 3-(4-(3-(4-chloro-2-fluorophenoxy)azetidin-1-yl)-1,3,5-triazin-2-ylamino)-N-ethylbenzamide

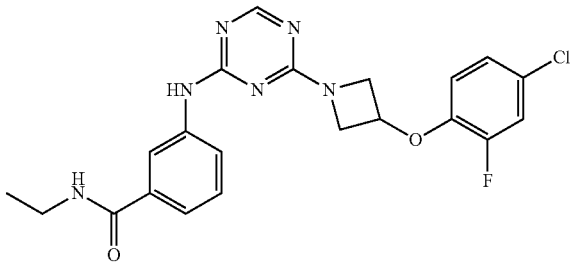 [SMILES: CCNC(=O)c1cccc(Nc2ncnc(N3CC(Oc4ccc(Cl)cc4F)C3)n2)c1]

Step 1

To a solution of 3-(4-chloro-2-fluorophenoxy) azetidine (3.6 g, 18.0 mmol) in CH₃CN (60 mL, 3 mL/mmol) was added Et₃N (7.2 mL, 50.0 mmol) and 2, 4-dichloro-1, 3, 5-triazine (3.0 g, 20.0 mmol) and the reaction mixture was stirred at RT for 1 h. Then the reaction mixture was concentrated under reduced pressure and extracted with EtOAc (2×50 mL). The organic extracts were washed with brine, dried over anhydrous sodium sulfate and concentrated under reduced pressure. Purification by column chromatography to obtain 2-chloro-4-(3-(4-chloro-2-fluorophenoxy)azetidin-1-yl)-1,3,5-triazine (0.800 g, 20%) as a solid. Observed mass (M+1): 315.0

Step 2

To a solution of 2-chloro-4-(3-(4-chloro-2-fluorophenoxy) azetidin-1-yl)-1,3,5-triazine (0.800 g, 2.54 mmol) in Isopropanol (8 mL, 3 mL/mmol) was added DIPEA (0.7 mL, 3.81 mmol) and 3-amino-N-methylbenzamide (0.382 g, 2.54 mmol) and the reaction mixture was stirred at 80° C. for 24 h. The reaction mixture was concentrated under reduced pressure and extracted with EtOAc (2×40 mL). The organic extracts were washed with brine, dried over anhydrous sodium sulfate and concentrated under reduced pressure. Purification by silica gel column chromatography to obtain 3-(4-(3-(4-chloro-2-fluorophenoxy)azetidin-1-yl)-1,3,5-triazin-2-ylamino)-N-methylbenzamide (0.527 g, 53%) as a solid. Observed mass (M+1): 428.9

Example S 3-(4-(3-(4-chloro-2-fluorophenoxy)azetidin-1-yl)-1,3,5-triazin-2-ylamino)-5-fluoro-N-methylbenzamide

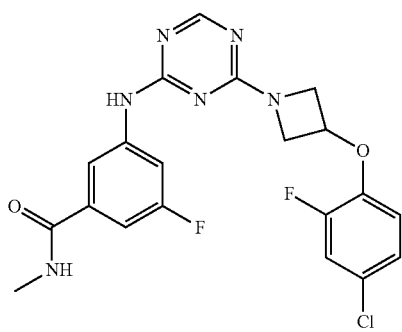 [SMILES: CNC(=O)c1cc(F)cc(Nc2ncnc(N3CC(Oc4ccc(Cl)cc4F)C3)n2)c1]

Step 1

To a solution of 3-fluoro-5-nitrobenzonitrile (1.0 g, 6.02 mmoL) in TFA (8 mL) was added water (1 mL) and conc. sulfuric acid (2 mL). The reaction mixture was heated to 70° C. and stirred for 24 h. Then the reaction mixture was cooled to 0° C. and liquid ammonia solution was added. The solidified solid was filtered through Celite® (diatomaceous earth) and washed with water to obtain 3-fluoro-5-nitrobenzamide (0.400 g, 36%) as an off white solid. Observed mass (M−1): 183.02.

Step 2

To a solution of 3-fluoro-5-nitrobenzamide (1.0 g, 5.43 mmoL) in DMF (17 mL) was added cesium carbonate (2.6 g, 8.14 mmoL) and dimethyl sulphate (547 mg, 4.34 mmol) and the reaction mixture was stirred at RT for 24 h. The reaction mixture was concentrated under reduced pressure and extracted with EtOAc (2×40 ml). The organic layer was washed with brine, dried over anhydrous sodium sulfate and concentrated under reduced pressure. Purification by silica gel column chromatography provided 3-fluoro-N-methyl-5-nitrobenzamide (0.800 g, 80%) as a solid. Observed mass (M−1): 196.9.

Step 3

To a solution of 3-fluoro-N-methyl-5-nitrobenzamide (500 mg, 2.52 mmoL) in methanol (7.5 mL) was added Pd/C (30%) and the mixture was stirred at RT for 1 h. The reaction mixture was filtered through Celite® (diatomaceous earth), washed with methanol and concentrated under reduced. Purification by silica gel column chromatography provided 3-amino-5-fluoro-N-methylbenzamide (0.300 g, 75%) as a solid.

Step 4

To a solution of 2-chloro-4-(3-(4-chloro-2-fluorophenoxy) azetidin-1-yl)-1,3,5-triazine (0.800 g, 2.54 mmol) [prepared as described for 2-chloro-4-(3-(2,4-dichlorophenoxy)azetidin-1-yl)pyrimidine in Example AAA] in isopropanol (8 mL) was added DIPEA (0.7 mL, 3.81 mmol) and 3-amino-N-methylbenzamide (382 mg, 2.54 mmol). The reaction mixture was stirred at 80° C. for 24 h. The reaction mixture was concentrated under reduced pressure and extracted with EtOAc (2×40 mL). The organic extracts were washed with brine, dried over anhydrous sodium sulfate and concentrated under reduced pressure. Purification by silica gel column chromatography provided 3-(4-(3-(4-chloro-2-fluorophenoxy)azetidin-1-yl)-1,3,5-triazin-2-ylamino)-N-methylbenzamide (0.537 g, 53%) as a solid. Observed mass (M+1): 428.9.

Example T 3-(4-(3-(4-chloro-2-fluorophenoxy)azetidin-1-yl)pyridin-2-ylamino)-N-methylbenzamide

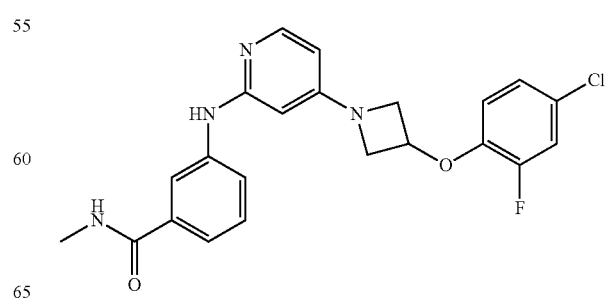

Step 1

To a solution of 2,4-dichloropyridine (0.500 g, 3.39 mmoL) and 4-amino-N-methylbenzamide (0.510 g, 3.39 mmoL) in dimethylacetamide (1 mL) was added cesium carbonate (1.6 g, 5.08 mmoL) and the reaction mixture was degassed for 15 min. $Pd_2(dba)_3$ (0.154 g, 0.169 mmol) and BINAP (105 mg, 0.169 mmol) were added and the reaction mixture was irradiated in the microwave at 120° C. for 1 h. Then reaction was quenched with water and extracted with EtOAc (2×50 mL). The organic extracts were washed with brine, dried over anhydrous sodium sulfate and concentrated under reduced pressure. Purification by silica gel column chromatography provided 3-((4-chloropyridin-2-yl)amino)-N-methylbenzamide (0.300 g, 38%) as a solid. Observed mass (M+1): 262.1

Step 2

To a solution of 3-((4-chloropyridin-2-yl)amino)-N-methylbenzamide (0.300 g, 1.14 mmol) in Isopropanol (4 mL) was added DIPEA (0.3 mL, 1.71 mmol) and 3-(2-fluoro-4-chlorophenoxy)azetidine (0.230 g, 1.14 mmol) [prepared as described in Example AAA] and the reaction mixture was heated at 80° C. for 7 h. The mixture was concentrated under reduced pressure and extracted with EtOAc (2×20 mL). The organic extracts were washed with brine, dried over anhydrous sodium sulfate and concentrated under reduced pressure. Purification by silica gel column chromatography provided 3-((4-(3-(4-chloro-2-fluorophenoxy)azetidin-1-yl)pyridin-2-yl)amino)-N-methylbenzamide (0.10 g, 3%) as a solid. Observed mass (M+1): 427.1

Example U 3-(4-(3-(4-chloro-2-fluorophenoxy)azetidin-1-yl)-6-methyl-1,3,5-triazin-2-ylamino)-N-methylbenzamide

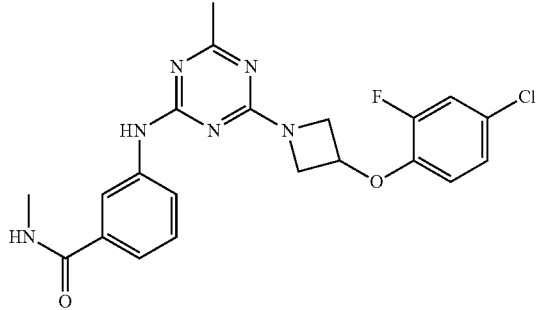 [SMILES: CNC(=O)c1cccc(Nc2nc(C)nc(N3CC(Oc4ccc(Cl)cc4F)C3)n2)c1]

Step 1

To a solution of 2,4,6-trichloro-1,3,5-triazine (1.0 g, 5.4 mmol) in $CH_2Cl_2$ (17 mL) was added MeMgCl (1.8 mL) drop wise and the reaction mixture was stirred at RT for 0.5 h. The reaction mixture was quenched with saturated $NH_4Cl$ solution and extracted with EtOAc (2×50 mL). The organic extracts were washed with brine, dried over anhydrous sodium sulfate and concentrated under reduced pressure to obtain 2,4-dichloro-6-methyl-1,3,5-triazine (0.800 g, 90%) as a solid. The crude material was taken to the next step without further purification.

Step 2

To a solution of 2,4-dichloro-6-methyl-1,3,5-triazine (0.800 g, 4.87 mmol) in isopropanol (15 mL) was added DIPEA (1.3 mL) and 3-(4-chloro-2-fluorophenoxy)azetidine (0.600 g, 2.92 mmol) and the reaction mixture was stirred at RT for 1 h. The mixture was concentrated under reduced pressure and extracted with EtOAc (2×40 mL). The organic extracts were washed with brine, dried over anhydrous sodium sulfate and concentrated under reduced pressure to obtain 2-chloro-4-(3-(4-chloro-2-fluorophenoxy)azetidin-1-yl)-6-methyl-1,3,5-triazine (1.0 g) as a solid. Observed mass (M+1): 329. The crude material was taken to next step without further purification.

Step 3

To a solution of 2-chloro-4-(3-(4-chloro-2-fluorophenoxy)azetidin-1-yl)-6-methyl-1,3,5-triazine (1.0 g, 3.04 mmol) in Isopropanol (10 mL) was added DIPEA (0.8 mL) and 3-amino-N-methylbenzamide (0.460 g, 3.04 mmol) and the reaction mixture was stirred at 80° C. for 24 h. The reaction mixture was concentrated under reduced pressure and extracted with EtOAc (2×40 mL) and water (2×40 mL). The organic extracts were washed with brine, dried over anhydrous sodium sulfate and concentrated under reduced pressure. Purification by silica gel column chromatography provided 3-((4-(3-(4-chloro-2-fluorophenoxy) azetidin-1-yl)-6-methyl-1,3,5-triazin-2-yl)amino)-N-methylbenzamide (0.057 g, 6%) as a solid. Observed mass (M+1): 443.1.

Example V 3-((2-(3-(4-fluorophenoxy)-1-azetidinyl)-4-pyridinyl)amino)-N-methylbenzamide

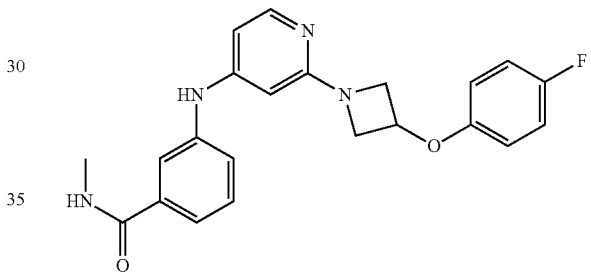

Step 1

To a solution of 3-(4-fluorophenoxy)azetidine (557 mg, 3.37 mmol) [prepared as described in Example AAA] in isopropanol (10 mL, 3 mL/mmol) was added DIPEA (1.5 mL, 8.42 mmol) and 2,4-dichloropyridine (500 mg, 3.37 mmol) and the mixture was heated at 80° C. for 7 h. The reaction mixture was concentrated under reduced pressure and extracted with EtOAc (2×20 mL). The organic extracts were washed with brine, dried over sodium sulfate and concentrated under reduced pressure. Purification by silica gel column chromatography provided 2-chloro-6-(3-(4-fluorophenoxy)azetidin-1-yl)pyridine (500 mg, 55%) as a solid. Observed mass (M+1): 279.1.

Step 2

To a solution of 2-chloro-6-(3-(4-fluorophenoxy) azetidin-1-yl)pyridine (500 mg, 1.79 mmoL) and 4-amino-N-methylbenzamide (270 mg, 1.79 mmol) in dimethylacetamide (5 mL, 3 mL/mmol) was added cesium carbonate (873 mg, 2.68 mmol) and the reaction was degassed for 15 min. $Pd_2(dba)_3$ (81 mg, 0.089 mmol) and BINAP (55 mg, 0.089 mmol) were added and the reaction was allowed to heat at 120° C. in the microwave. The reaction was quenched with water and extracted with EtOAc (2×50 mL). The organic extracts were washed with brine, dried over sodium sulfate, concentrated under reduced pressure and purified by silica gel column chromatography to afford 3-(6-(3-(4-fluorophenoxy) azetidin-1-yl)pyridin-2-ylamino)-N-methylbenzamide (61 mg, 13%) as a solid. Observed mass (M+1): 393.1. The following compounds were prepared as described in Example V above using appropriate starting materials.

Example W
3-((6-(3-(4-chloro-2-fluorophenoxy)-1-azetidinyl)-2-pyridinyl)amino)-N-methylbenzamide
Example X
5-((6-(3-(4-chloro-2-fluorophenoxy)-1-azetidinyl)-2-pyridinyl)amino)-2-fluoro-N-methylbenzamide
Example Y
2-chloro-5-((6-(3-(4-chloro-2-fluorophenoxy)-1-azetidinyl)-2-pyridinyl)amino)-N-methylbenzamide
Example Z
3-((6-(3-(4-chloro-2-fluorophenoxy)-1-azetidinyl)-4-pyrimidinyl)amino)-N-methylbenzamide
Example AA
3-((2-(3-(4-chloro-2-fluorophenoxy)-1-azetidinyl)-4-pyridinyl)amino)-N-methylbenzamide
Example AB
3-((6-(3-(4-chloro-2-fluorophenoxy)-1-azetidinyl)-5-fluoro-4-pyrimidinyl)amino)-N-methylbenzamide Example AC N-methyl-3-((2-((3-(4-(trifluoromethoxy)phenoxy)propyl)amino)-4-pyrimidinyl)amino)benzamide

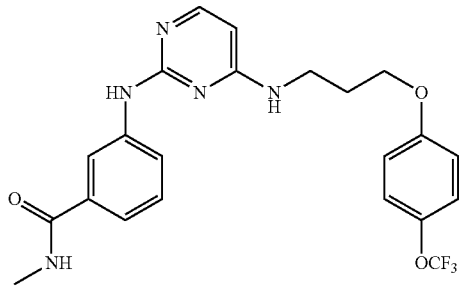 [SMILES: CNC(=O)c1cccc(Nc2nccc(NCCCOc3ccc(OC(F)(F)F)cc3)n2)c1]

Step 1

To a solution of 3-aminopropan-1-ol (1.0 g, 13.1 mmol) and isobenzofuran-1,3-dione (2.0 g, 13.1 mmol) in toluene (25 mL, 3 mL/mmol) was added Et$_3$N (2 mL, 13.1 mmol) and the reaction was heated at reflux for 24 h. Then reaction was quenched with water and extracted with EtOAc (2×40 mL). The organic extracts were washed with brine, dried over sodium sulfate and concentrated under reduced pressure to afford 2-(3-hydroxypropyl)isoindoline-1,3-dione (1.8 g, 87%). Observed mass (M+1): 206.1. This material was taken to the next step without further purification.

Step 2

To a solution of 2-(3-hydroxypropyl) isoindoline-1,3-dione (1.8 g, 8.77 mmol) in CH$_2$Cl$_2$ (30 mL, 3 mL/mmol) was added Et$_3$N (2 mL, 13.1 mmol). After stirring for 10 min at 0° C., tosylchloride (2 g, 10.5 mmol) was added and the reaction was stirred for 12 h at RT. The reaction was quenched with water and extracted with CH$_2$Cl$_2$ (2×50 mL). The organic extracts were washed with brine, dried over sodium sulfate and concentrated under reduced pressure. Purification by silica gel column chromatography provided 3-(1,3-dioxoisoindolin-2-yl)propyl 4-methylbenzenesulfonate (3 mg, 96%). Observed mass (M+1): 360.1.

Step 3

To a solution of 3-(1,3-dioxoisoindolin-2-yl)propyl 4-methylbenzenesulfonate (3 g, 8.35 mmol) in DMF (25 mL, 3 mL/mmol) was added potassium carbonate (1.8 g, 12.5 mmol) and 4-trifluoromethoxyphenol (1.5 g, 8.35 mmol) and the reaction was heated at 120° C. for 2 h. The reaction mixture was concentrated under reduced pressure and extracted with EtOAc (2×60 mL). The organic extracts were washed with brine, dried over sodium sulfate and concentrated under reduced pressure. Purification by silica gel column chromatography provided 2-(3-(4-(trifluoromethoxy)phenoxy) propyl) isoindoline-1,3-dione (1 g, 33%) as a solid. Observed mass (M+1): 366.0.

Step 4

To a solution of 2(3-(4-trifluoromethoxy)phenoxy)propyl) isoindoline-1,3-dione (700 mg, 1.91 mmol) in EtOH (6 mL, 3 mL/mmol) was added hydrazine hydrate (144 mg, 2.87 mmol) and the reaction was allowed to heat at reflux for 3 h. Then reaction mixture was filtered and concentrated under reduced pressure to provide 3-(4-(trifluoromethoxy)phenoxy) propan-1-amine (450 mg, 99%) as a solid. Observed mass (M+1): 236. This material was taken to the next step without further purification.

Step 5

To a solution of 3-(4-(trifluoromethoxy)phenoxy)propan-1-amine (450 mg, 1.91 mmol) in isopropanol (8 mL, 3 mL/mmol) was added DIPEA (0.5 mL, 2.86 mmol) and 2,4-dichloropyrimidine (340 mg, 2.29 mmol) and the mixture was stirred at 80° C. for 24 h. Then reaction mixture was concentrated under reduced pressure and extracted with EtOAc (2×30 mL) and water (2×30 mL). The EtOAc layer was washed with brine, dried over sodium sulfate and concentrated under reduced pressure. Purification by column chromatography provided 2-chloro-N-(3-(4-(trifluoromethoxy)phenoxy)propyl)pyrimidin-4-amine (400 mg, 60%) as a solid. Observed mass (M+1): 348.1.

Step 6

To a solution of 2-chloro-N-(3-(4-trifluoromethoxy) phenoxy)propyl)pyrimidin-4-amine (400 mg, 1.15 mmol) and 4-amino-N-methyl benzamide (172 mg, 1.15 mmol) in DMA (4 mL, 3 mL/mmol) was added cesium carbonate (562 mg, 1.72 mmol) and the mixture was degassed for 15 min. Pd$_2$(dba)$_3$ (52 mg, 0.057 mmoL) and BINAP (35 mg, 0.057 mmol) were added and the reaction was allowed to heat at 100° C. in the microwave for 0.5 h. The reaction was quenched with water and extracted with EtOAc (2×25 mL). The organic extracts were washed with brine, dried over sodium sulfate and concentrated under reduced pressure. Purification by silica gel column chromatography afforded N-methyl-3-(4-(3-(4-(trifluoromethoxy)phenoxy) propylamino)pyrimidin-2-ylamino)benzamide (260 mg, 13%) as a solid.

Example AD

N,2-dimethyl-3-((4-(4-((4-(trifluoromethoxy)benzyl)oxy)-1-piperidinyl)-1,3,5-triazin-2-yl)amino)benzamide

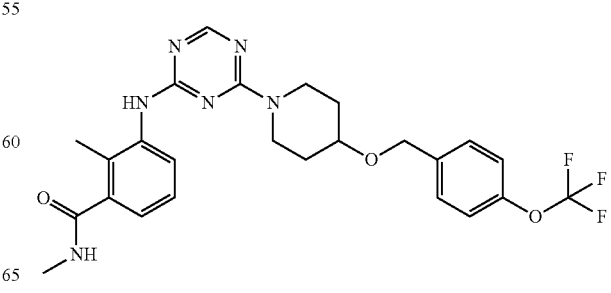

Step 1

To a solution of tert-butyl 4-hydroxypiperidine-1-carboxylate (1 g, 4.97 mmol) in DMF (15 mL, 3 mL/mmol) was added sodium hydride (143 mg, 5.95 mmol). After being stirred for 0.5 h at 0° C. 1-(bromomethyl)-4-(trifluoromethoxy)benzene (1.9 g, 7.97 mmol) was added and the reaction was stirred for 24 h at RT. The reaction was quenched with water and extracted with EtOAc (2×20 mL). The organic extracts were washed with brine, dried over sodium sulfate and concentrated under reduced pressure and purified by silica gel column chromatography to give tert-butyl 4-(4-(trifluoromethoxy)benzyloxy)piperidine-1-carboxylate (1.8 g) which was taken to the next reaction without further purification. Observed mass (M+1): 376.

Step 2

To a solution of tert-butyl 4-(4-(trifluoromethoxy)benzyloxy)piperidine-1-carboxylate (1.7 g, 4.53 mmol) in $CH_2Cl_2$ (15 mL, 3 mL/mmol) was added TFA (10 mL) and the mixture was stirred for 2 h at RT. The reaction mixture was concentrated under reduced pressure, taken up in chloroform, filtered and washed with diethyl ether to provide 4-(4-(trifluoromethoxy)benzyloxy) piperidine (1.2 g, 96%) as TFA salt. Observed mass (M+1): 276

Step 3

To a solution of 4-(4-(trifluoromethoxy)benzyloxy)piperidine (2.2 g, 8.00 mmol) in isopropanol (25 mL, 3 mL/mmol) was added DIPEA (3.6 mL, 0.02 mol) and 2,4-dichloro-1,3,5-triazine (1.2 g, 8.00 mmol) and the reaction was heated at 80° C. for 2 h. The reaction mixture was concentrated under reduced pressure and extracted with EtOAc (2×40 mL). The organic extracts were washed with brine, dried over sodium sulfate and concentrated under reduced pressure. Purification by silica gel column chromatography provided 2-chloro-4-(4-((4-(trifluoromethoxy)benzyl)oxy)piperidin-1-yl)-1,3,5-triazine (800 mg, 57%) as a solid. Observed mass (M+1): 389.0.

Step 4

To a solution of 2-chloro-4-(4-((4-(trifluoromethoxy)benzyl)oxy)piperidin-1-yl)-1,3,5-triazine (500 mg, 1.28 mmol) in isopropanol (4 mL, 3 mL/mmol) was added DIPEA (0.4 mL, 1.92 mmol) and 3-amino-N,2-dimethylbenzamide (211 mg, 1.29 mmol) and the reaction was stirred at 80° C. for 24 h. The reaction mixture was concentrated under reduced pressure and extracted with EtOAc (2×30 ml). The organic extracts were washed with brine, dried over sodium sulfate and concentrated under reduced pressure. Purification by silica gel column chromatography provided N,2-dimethyl-3-((4-(4-((4-(trifluoromethoxy)benzyl)oxy)piperidin-1-yl)-1,3,5-triazin-2-yl)amino)benzamide (100 mg, 16%) as a solid. Observed mass (M+1): 517.1.

Example AE 3-((4-(3-(4-chloro-2-fluorophenoxy)-1-azetidinyl)-1,3,5-triazin-2-yl)oxy)-N-methylbenzamide

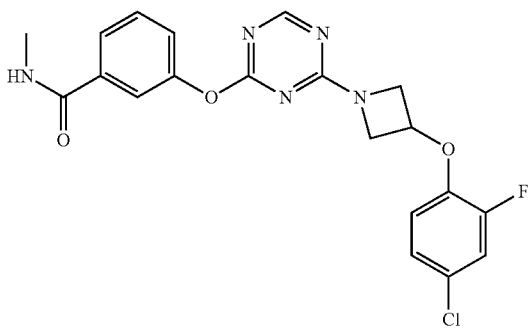 [SMILES: CNC(=O)c1cccc(Oc2ncnc(N3CC(Oc4ccc(Cl)cc4F)C3)n2)c1]

To a solution of 2-chloro-4-(3-(4-chloro-2-fluorophenoxy)azetidin-1-yl)-1,3,5-triazines (600 mg, 1.91 mmol) in $CH_3CN$ (6 mL, 3 mL/mmol) was added potassium tert-butoxide (320 mg, 2.86 mmol) and 3-hydroxy-N-methylbenzamide (288 mg, 1.91 mmol) was added and reaction was stirred at 80° C. for 24 h. The reaction mixture was concentrated under reduced pressure and extracted with EtOAc (2×30 mL). The organic extracts were washed with brine, dried over sodium sulfate and concentrated under reduced pressure. Purification by column chromatography provided 3-((4-(3-(4-chloro-2-fluorophenoxy)azetidin-1-yl)-1,3,5-triazin-2-yl)oxy)-N-methylbenzamide (500 mg, 62%) as a solid. Observed mass (M+1): 428.9.

Example AF 3-((3-(3-(4-fluorophenoxy)-1-azetidinyl)phenyl)amino)-N-methylbenzamide

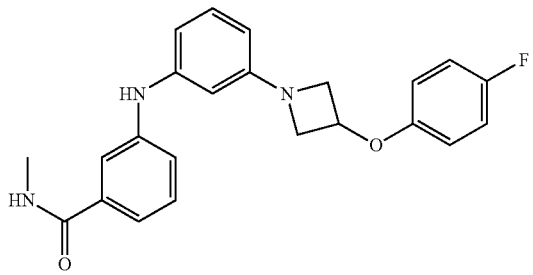 [SMILES: CNC(=O)c1cccc(Nc2cccc(N3CC(Oc4ccc(F)cc4)C3)c2)c1]

Step 1

To a solution of 1, 3-dibromobenzene (500 mg, 2.13 mmol) and 3-(4-fluorophenoxy)azetidine (357 mg, 2.13 mmol) in toluene (7 mL, 3 mmol) was added cesium carbonate (600 mg, 5.3 mmol) and degassed for 15 min. $Pd_2(dba)_3$ (97 mg, 0.106 mmol) and BINAP (66 mg, 0.106 mmol) were added and the mixture was heated in the microwave for 30 min at 100° C. The reaction mixture was concentrated under reduced pressure and extracted with EtOAc (2×30 mL). The organic extracts were washed with brine, dried over sodium sulfate and concentrated under reduced pressure. Purification by silica gel column chromatography provided 1-(3-bromophenyl)-3-(4-fluorophenoxy)azetidine (200 mg, 30%) as a solid. Observed mass (M+1): 322.1.

Step 2

To a solution of 1-(3-bromophenyl)-3-(4-fluorophenoxy)azetidine (400 mg, 1.24 mmol) and 3-amino-N-methylbenzamide (187 mg, 1.24 mmol) in toluene (4 mL, 3 mmoL) was added cesium carbonate (180 mg, 1.86 mmol) and degassed for 15 min. $Pd_2(dba)_3$ (56 mg, 0.062 mmol) and BINAP (38 mg, 0.062 mmol) were added and the mixture was heated in the microwave for 30 min at 100° C. The reaction mixture was concentrated under reduced pressure and extracted with EtOAc (2×30 mL) and water (2×30 mL). The organic extracts were washed with brine, dried over sodium sulfate and concentrated under reduced pressure then purified by silica gel column chromatography to provide 3-((3-(3-(4-fluorophenoxy)azetidin-1-yl)phenyl)amino)-N-methylbenzamide (113 mg, 23%) as a solid. Observed mass (M+1): 393.1

The following compound was prepared as described in Example AF above using appropriate starting materials.

Example AG
3-((3-(3-(4-chloro-2-fluorophenoxy)-1-azetidinyl)phenyl)amino)-N-methylbenzamide

Example AH
3-((5-fluoro-2-(3-(4-fluorophenoxy)-1-azetidinyl)-4-pyrimidinyl)amino)-N-methylbenzamide

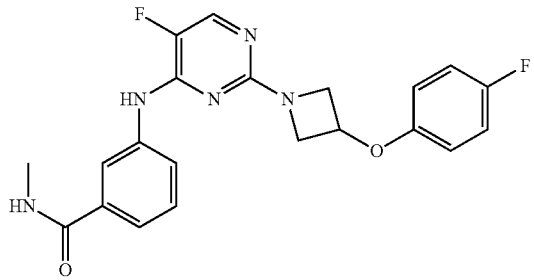 [SMILES: CNC(=O)c1cccc(Nc2nc(N3CC(Oc4ccc(F)cc4)C3)ncc2F)c1]

Step 1

To a solution of 2,4-dichloro-5-fluoropyrimidine (1 g, 5.98 mmol) in isopropanol (18 mL, 3 mL/mmol) was added DIPEA (1.6 mL, 8.9 mmol) and 3-amino-N-methylbenzamide (900 mg, 5.98 mmol) and the mixture was heated at 80° C. for 7 h. The reaction mixture was concentrated under reduced pressure and extracted with EtOAc (2×40 mL) and water (2×40 mL). The organic extracts were washed with brine, dried over sodium sulfate and concentrated under reduced pressure. Purification by column chromatography provided 3-((2-chloro-5-fluoropyrimidin-4-yl)amino)-N-methylbenzamide (800 mg, 50%) as a solid. Observed mass (M+1): 281.1

Step 2

To a solution of 3-((2-chloro-5-fluoropyrimidin-4-yl)amino)-N-methylbenzamide (500 mg, 1.78 mmoL) and 3-(4-fluorophenoxy)azetidine (298 mg, 1.78 mmol) in DMA (6 mL, 3 mL/mmoL) was added cesium carbonate (580 mg, 2.67 mmol) and the reaction was degassed for 15 min. Pd$_2$(dba)$_3$ (80 mg, 0.089 mmol) and BINAP (55 mg, 0.089 mmol) and the reaction was allowed to heat at 100° C. in the microwave. The reaction was quenched with water and extracted with EtOAc (2×25 mL). The organic extracts were washed with brine, dried over sodium sulfate and concentrated under reduced pressure then purified by silica gel column chromatography to give 3-((5-fluoro-2-(3-(4-fluorophenoxy)azetidin-1-yl)pyrimidin-4-yl)amino)-N-methylbenzamide (97 mg, 15%) as solid. Observed mass (M+1): 412.1

The following compounds were prepared as described in Example AH above using appropriate starting materials.

Example AI
N-methyl-3-((4-(6-(2,2,2-trifluoroethoxy)-3,4-dihydro-2(1H)-isoquinolinyl)-2-pyrimidinyl)amino)benzamide

Example AJ
3-((2-(3-(4-chloro-2-fluorophenoxy)-1-azetidinyl)-4-pyrimidinyl)amino)-N-methylbenzamide

Example AK
3-((2-(3-(4-chloro-2-fluorophenoxy)-1-azetidinyl)-5-fluoro-4-pyrimidinyl)amino)-N-methylbenzamide

BIOLOGICAL EXAMPLES

Cell-Based Assays

Compounds were tested on human Nav1.7 (hNav1.7) expressed stably in 293 cells, which have no endogenous sodium channels. Two forms of whole-cell patch-clamp assays were used. In both, peak current through Nav1.7 was evoked by a depolarizing voltage pulse, and currents were monitored as a function of time in response to exposure to several different concentrations of drug. Automated electrophysiology uses the PatchXpress 7000A system. Up to sixteen cells at a time were voltage-clamped in parallel, and the steady-state voltage dependence of inactivation was determined experimentally for each cell. For each cell, fractional inactivation was set at 20%, and peak current through Nav1.7 as a function of time was measured in response to increasing concentrations of test compound. Manual electrophysiology refers to conventional whole-cell patch-clamping (Hamill et al., 1981). After formation of the whole-cell clamp, cells were lifted off the bottom of the dish with the patch pipette and positioned directly in front of an array of glass microperfusion tubes each with internal diameter about 250 microns, with individual compound concentrations flowing from each tube. Current as a function of time in response to increasing drug concentrations was measured with Nav1.7 fully in the resting state (holding voltage set to −140 mV) and on the same cells with the holding voltage set to produce about 20% inactivation. Compounds were not applied for a prespecified time, but for as long as required to achieve a stable level of block. For both forms of electrophysiology, offline analysis was used to correct for rundown of channel current and to determine percent inhibition as a function of drug concentration. IC$_{50}$ were determined by fitting to the Hill equation.

Average IC$_{50}$ value of a representative number of compounds of Formula (I) in this assay is provided in the Table 1 above and Table 2 below.

TABLE 2

| Example | Structure | Mass Spec M, M + 1 or M − 1 | hNav1.7 IC$_{50}$ μM (Avg) |
|---|---|---|---|
| AAA | 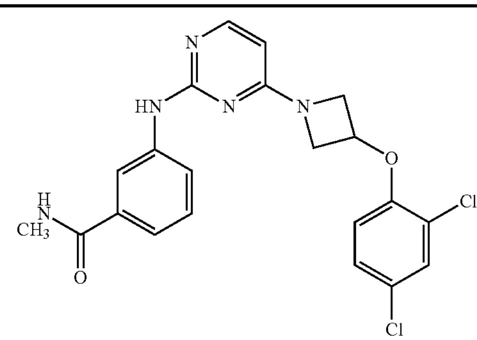 | 443.9 | 0.52 |

TABLE 2-continued

| Example | Structure | Mass Spec M, M + 1 or M − 1 | hNav1.7 IC$_{50}$ μM (Avg) |
|---|---|---|---|
| A | 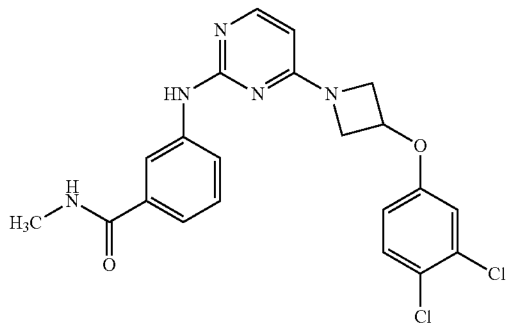 [SMILES: CNC(=O)c1cccc(Nc2nccc(N3CC(Oc4ccc(Cl)c(Cl)c4)C3)n2)c1] | 443.9 | 0.78 |
| B | 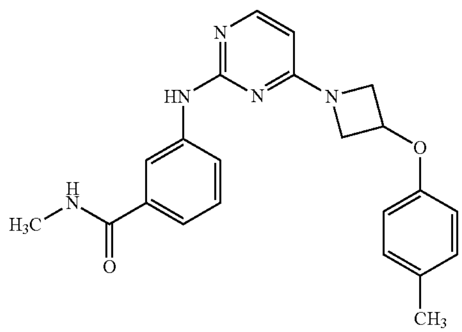 [SMILES: CNC(=O)c1cccc(Nc2nccc(N3CC(Oc4ccc(C)cc4)C3)n2)c1] | 390.3 | 2.00 |
| C | 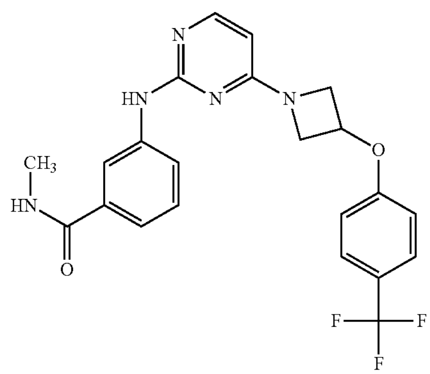 [SMILES: CNC(=O)c1cccc(Nc2nccc(N3CC(Oc4ccc(C(F)(F)F)cc4)C3)n2)c1] | 444.3 | 1.55 |
| D | 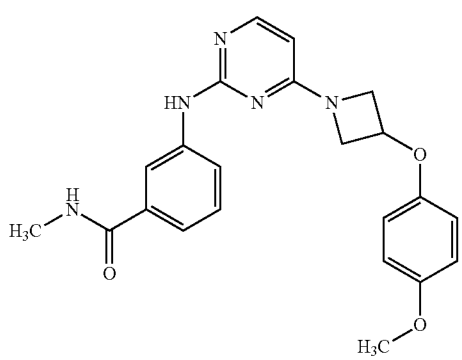 [SMILES: CNC(=O)c1cccc(Nc2nccc(N3CC(Oc4ccc(OC)cc4)C3)n2)c1] | 406.3 | 0.43 |

TABLE 2-continued

| Example | Structure | Mass Spec M, M + 1 or M − 1 | hNav1.7 IC$_{50}$ μM (Avg) |
|---|---|---|---|
| E | 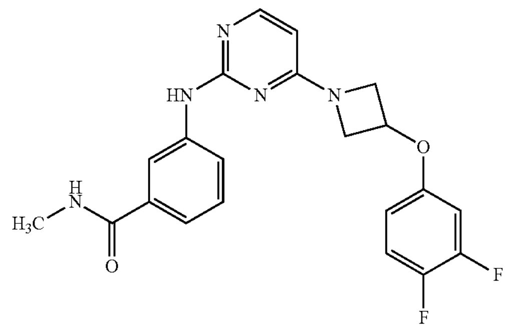 [SMILES: CNC(=O)c1cccc(Nc2nccc(N3CC(Oc4ccc(F)c(F)c4)C3)n2)c1] | 412.2 | 1.60 |
| F | 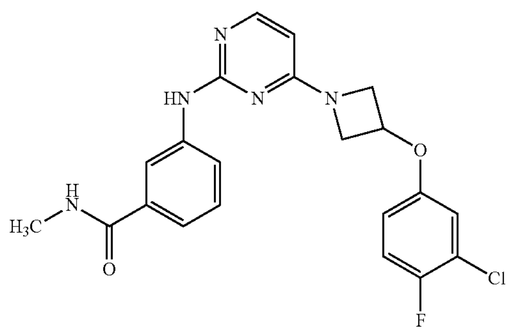 [SMILES: CNC(=O)c1cccc(Nc2nccc(N3CC(Oc4ccc(F)c(Cl)c4)C3)n2)c1] | 428.2 | 2.83 |
| G | 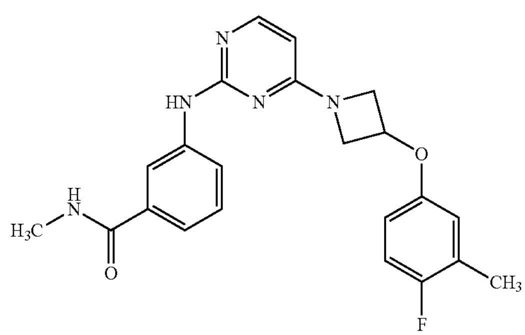 | 408.3 | 1.41 |
| H | 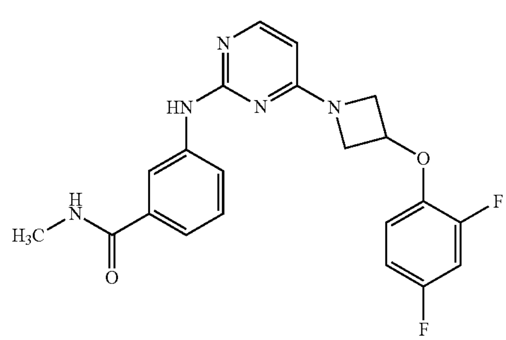 [SMILES: CNC(=O)c1cccc(Nc2nccc(N3CC(Oc4ccc(F)cc4F)C3)n2)c1] | 412.3 | 2.16 |

TABLE 2-continued

| Example | Structure | Mass Spec M, M + 1 or M − 1 | hNav1.7 IC$_{50}$ μM (Avg) |
|---|---|---|---|
| I | 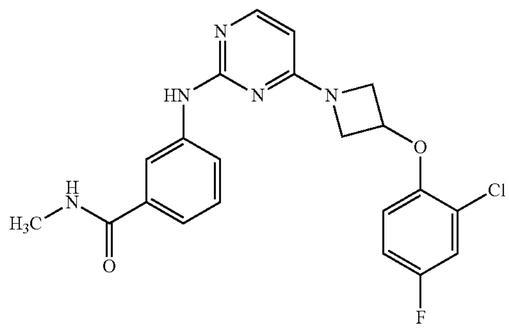 [SMILES: CNC(=O)c1cccc(Nc2nccc(N3CC(Oc4ccc(F)cc4Cl)C3)n2)c1] | 428.2 | 0.63 |
| J | 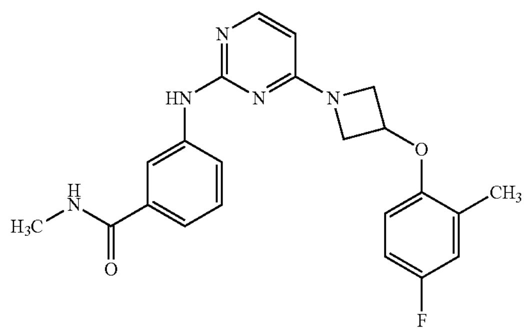 | 406.4 | 0.08 |
| K | 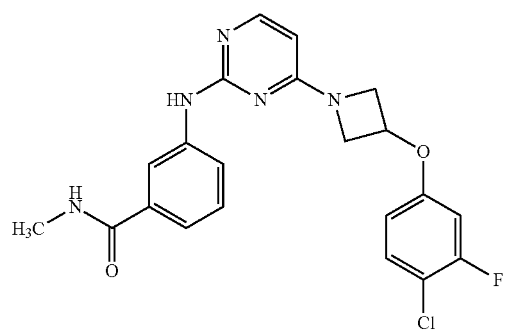 [SMILES: CNC(=O)c1cccc(Nc2nccc(N3CC(Oc4ccc(Cl)c(F)c4)C3)n2)c1] | 428.2 | 0.74 |
| L | 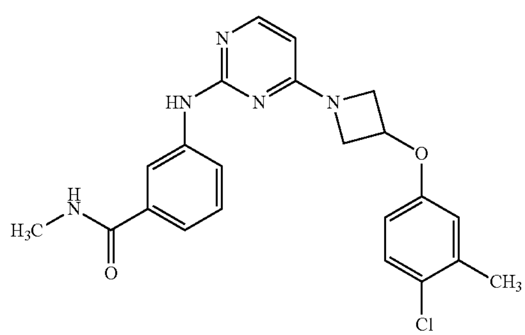 | 424.2 | 0.31 |

TABLE 2-continued

| Example | Structure | Mass Spec M, M + 1 or M − 1 | hNav1.7 IC$_{50}$ μM (Avg) |
|---|---|---|---|
| M | 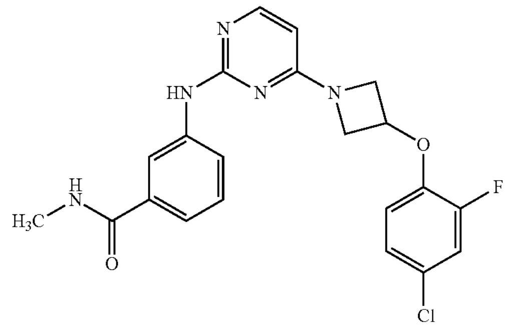 [SMILES: CNC(=O)c1cccc(Nc2nccc(N3CC(Oc4ccc(Cl)cc4F)C3)n2)c1] | 428.4 | 2.30 |
| N | 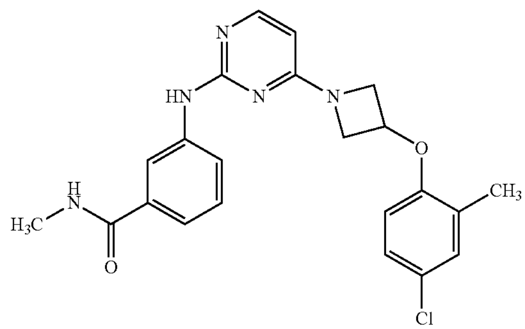 | 424.3 | 0.26 |
| O | 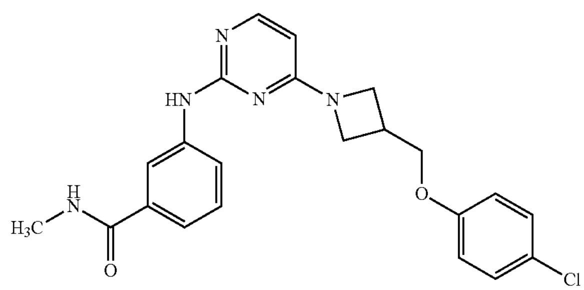 [SMILES: CNC(=O)c1cccc(Nc2nccc(N3CC(COc4ccc(Cl)cc4)C3)n2)c1] | 424.4 | 2.55 |
| P | 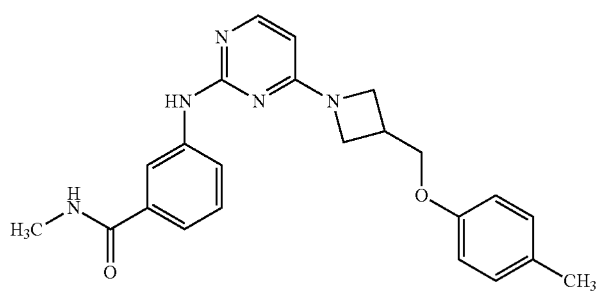 | 403 | 0.81 |
| Q | 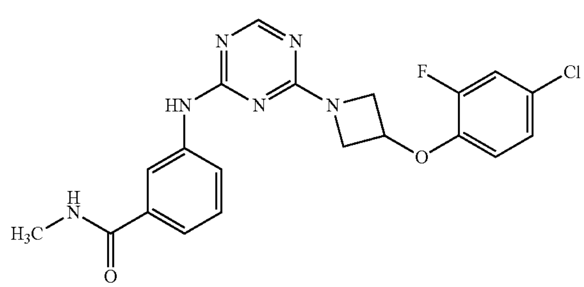 [SMILES: CNC(=O)c1cccc(Nc2ncnc(N3CC(Oc4ccc(Cl)cc4F)C3)n2)c1] | 428.9 | 2.99 |

TABLE 2-continued

| Example | Structure | Mass Spec M, M + 1 or M − 1 | hNav1.7 IC$_{50}$ μM (Avg) |
|---|---|---|---|
| R | 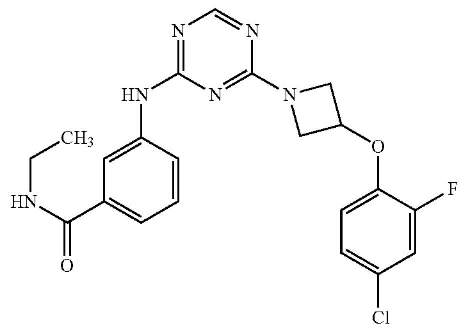 | 443 | 1.14 |
| S | 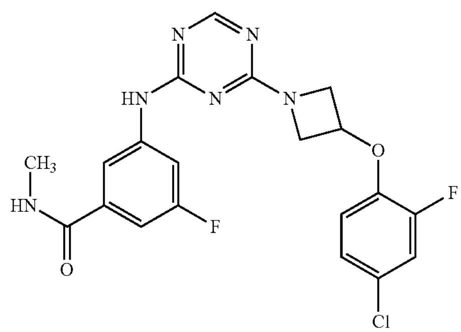 [SMILES: CNC(=O)c1cc(F)cc(Nc2ncnc(N3CC(Oc4ccc(Cl)cc4F)C3)n2)c1] | 446.8 | >30 |
| T | 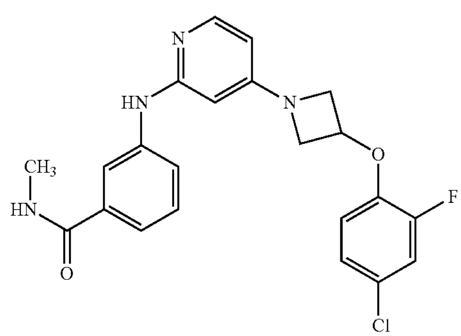 [SMILES: CNC(=O)c1cccc(Nc2cc(N3CC(Oc4ccc(Cl)cc4F)C3)ccn2)c1] | 427.1 | 4.50 |
| U | 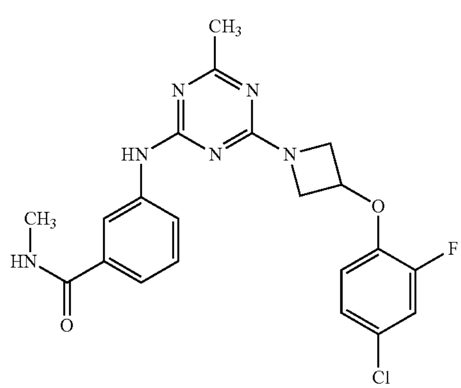 [SMILES: CNC(=O)c1cccc(Nc2nc(C)nc(N3CC(Oc4ccc(Cl)cc4F)C3)n2)c1] | 443.1 | >30 |

TABLE 2-continued

| Example | Structure | Mass Spec M, M + 1 or M − 1 | hNav1.7 IC$_{50}$ μM (Avg) |
|---|---|---|---|
| V | 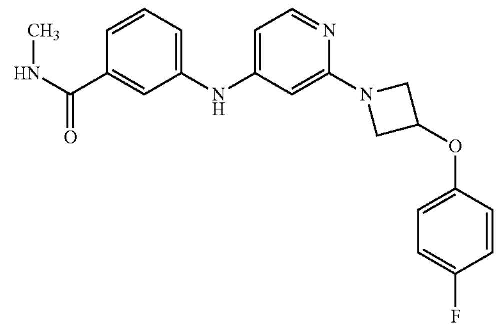 [SMILES: CNC(=O)c1cccc(Nc2ccnc(N3CC(Oc4ccc(F)cc4)C3)c2)c1] | 392.8 | 5.78 |
| W | 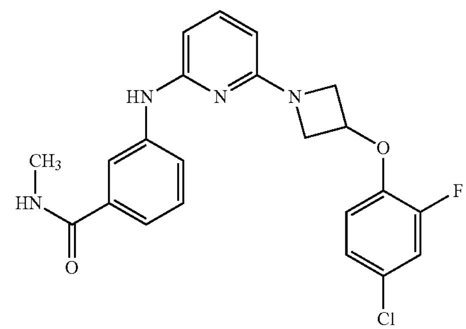 [SMILES: CNC(=O)c1cccc(Nc2cccc(N3CC(Oc4ccc(Cl)cc4F)C3)n2)c1] | 427.3 | 2.78 |
| X | 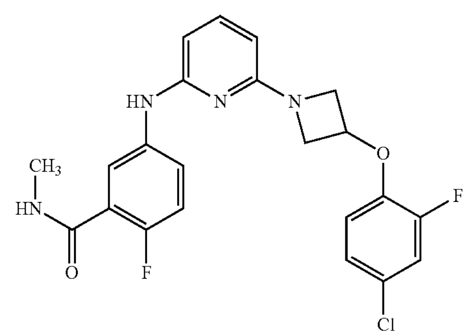 [SMILES: CNC(=O)c1cc(Nc2cccc(N3CC(Oc4ccc(Cl)cc4F)C3)n2)ccc1F] | 445.1 | 4.46 |
| Y | 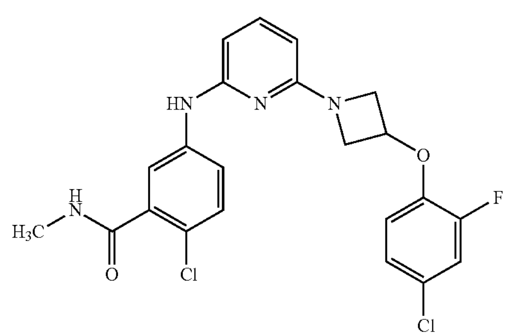 [SMILES: CNC(=O)c1cc(Nc2cccc(N3CC(Oc4ccc(Cl)cc4F)C3)n2)ccc1Cl] | 462 | >30 |

TABLE 2-continued

| Example | Structure | Mass Spec M, M + 1 or M − 1 | hNav1.7 IC$_{50}$ μM (Avg) |
|---|---|---|---|
| Z | 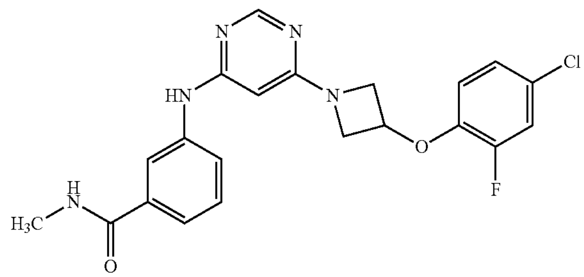 [SMILES: CNC(=O)c1cccc(Nc2cc(N3CC(Oc4ccc(Cl)cc4F)C3)ncn2)c1] | 428 | 12.71 |
| AA | 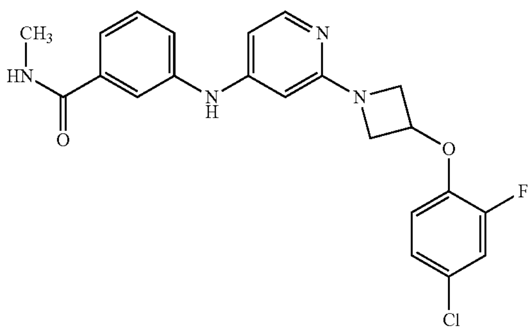 [SMILES: CNC(=O)c1cccc(Nc2ccnc(N3CC(Oc4ccc(Cl)cc4F)C3)c2)c1] | 427.2 | 7.15 |
| AB | 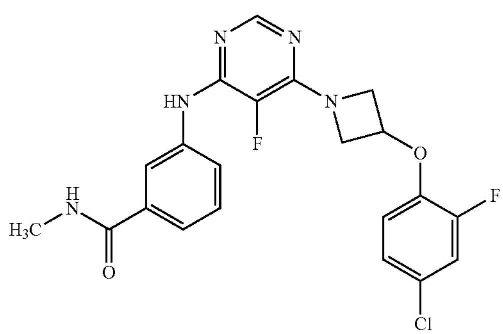 [SMILES: CNC(=O)c1cccc(Nc2ncnc(N3CC(Oc4ccc(Cl)cc4F)C3)c2F)c1] | 445.8 | >30 |
| AC | 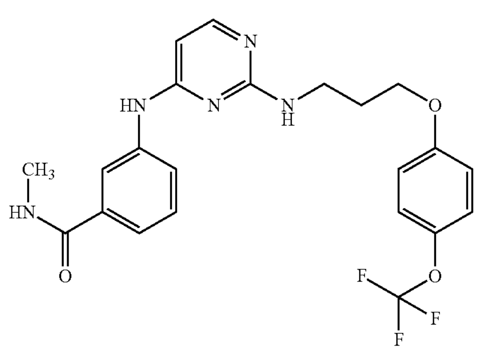 [SMILES: CNC(=O)c1cccc(Nc2ccnc(NCCCOc3ccc(OC(F)(F)F)cc3)n2)c1] | 462 | 1.17 |

TABLE 2-continued

| Example | Structure | Mass Spec M, M + 1 or M − 1 | hNav1.7 IC$_{50}$ µM (Avg) |
|---|---|---|---|
| AD | 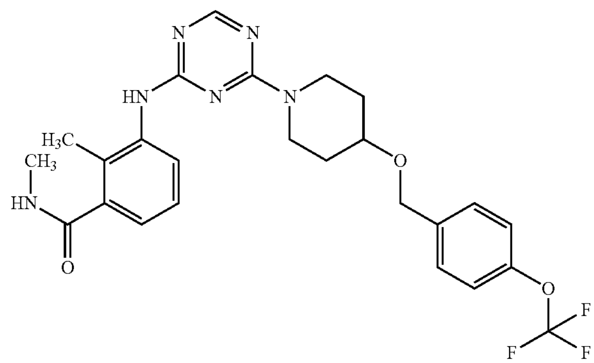 [SMILES: CNC(=O)c1cccc(Nc2ncnc(N3CCC(OCc4ccc(OC(F)(F)F)cc4)CC3)n2)c1C] | 517 | 28.56 |
| AE | 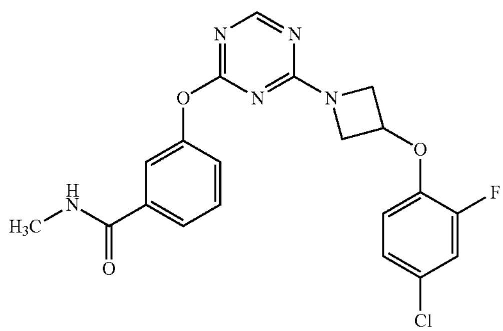 [SMILES: CNC(=O)c1cccc(Oc2ncnc(N3CC(Oc4ccc(Cl)cc4F)C3)n2)c1] | 429.9 | >30 |
| AF | 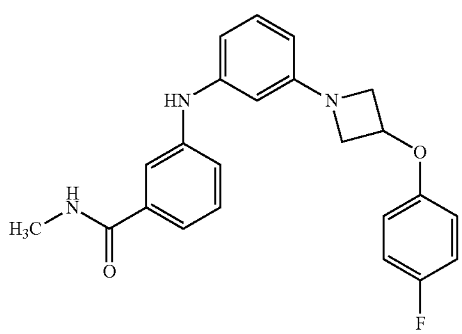 [SMILES: CNC(=O)c1cccc(Nc2cccc(N3CC(Oc4ccc(F)cc4)C3)c2)c1] | 392 | 9.53 |
| AG | 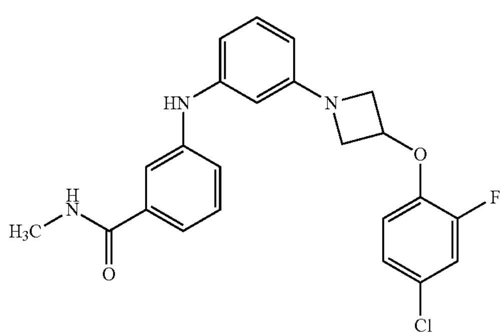 [SMILES: CNC(=O)c1cccc(Nc2cccc(N3CC(Oc4ccc(Cl)cc4F)C3)c2)c1] | 426.1 | >30 |

TABLE 2-continued

| Example | Structure | Mass Spec M, M + 1 or M − 1 | hNav1.7 IC$_{50}$ µM (Avg) |
|---|---|---|---|
| AH | 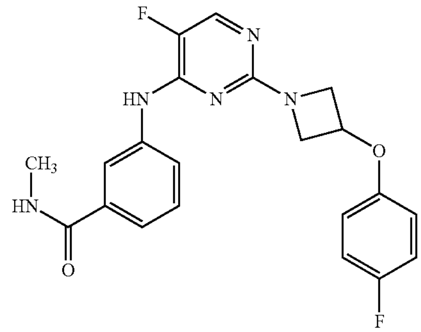 [SMILES: CNC(=O)c1cccc(Nc2nc(N3CC(Oc4ccc(F)cc4)C3)ncc2F)c1] | 412.1 | 0.34 |
| AI | 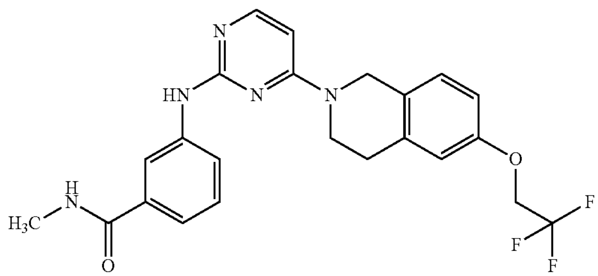 [SMILES: CNC(=O)c1cccc(Nc2nccc(N3CCc4cc(OCC(F)(F)F)ccc4C3)n2)c1] | 458 | 1.44 |
| AJ | 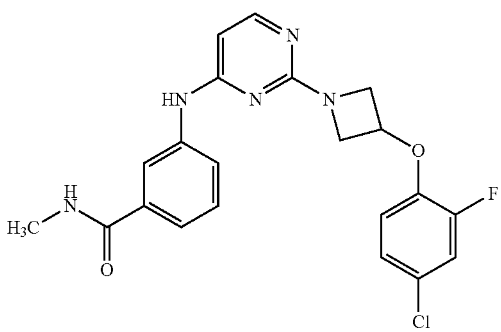 [SMILES: CNC(=O)c1cccc(Nc2ccnc(N3CC(Oc4ccc(Cl)cc4F)C3)n2)c1] | 428 | 2.26 |
| AK | 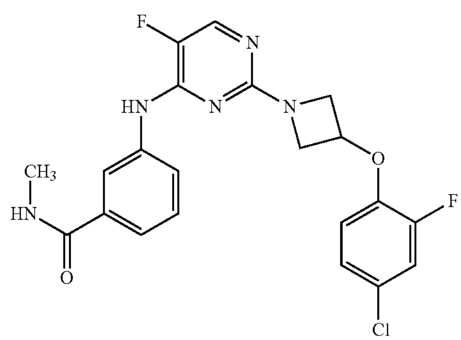 [SMILES: CNC(=O)c1cccc(Nc2nc(N3CC(Oc4ccc(Cl)cc4F)C3)ncc2F)c1] | 446 | 0.43 |

In Vivo Assays

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 500 µL with a 30 g needle. Immediately following injection, a small metal band can be affixed to the plantar side of the left hindpaw with a drop of loctite. Animals may be then placed into the testing chambers and the number of flinches can be recorded between 10-40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a maximal potential effect (% MPE) calculated with the following formula:

(−(Individual score−Vehicle average score)/Vehicle average score))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect

FORMULATION EXAMPLES

The following are representative pharmaceutical formulations containing a compound of Formula (I).

Tablet Formulation

The following ingredients may be mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients may be mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound of Formula (I):

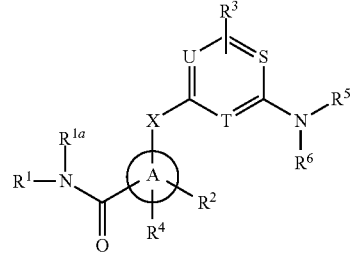

where:
X is —NH;
S, T and U are independently —CR$^3$— or —N—; selected from:

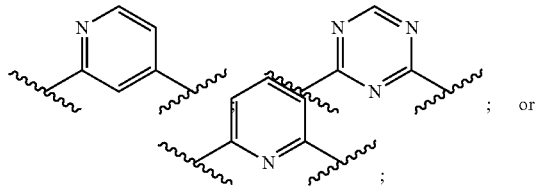

A is phenyl;
R$^1$ is hydrogen, alkyl, haloalkyl, substituted alkyl, or cycloalkyl, wherein said cycloalkyl is optionally substituted with one to three substituents-independently selected from alkyl, halo, haloalkyl, alkoxy, hydroxyl, or haloalkoxy;
R$^{1a}$ is hydrogen;
R$^2$ is hydrogen, alkyl, substituted alkyl, aryl, heteroaryl, cycloalkyl, halo, haloalkyl, haloalkoxy, alkoxy, alkoxyalkoxy, hydroxy, carboxy, alkoxycarbonyl, cyano, amino, monosubstituted or disubstituted amino, sulfonyl, or alkoxyalkyl;
each R$^3$ is hydrogen;
R$^4$ is hydrogen, alkyl, substituted alkyl, halo, alkoxy, hydroxy, carboxy, —CONH$_2$, —CONMe$_2$, cycloalkyl, or dialkylamino;
R$^5$ and R$^6$ together with the nitrogen atom to which they are attached form ring B having the formula:

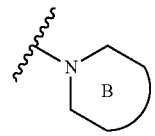

wherein ring B is a heterocyclyl ring-selected from:
a) azetidin-1-yl, pyrrolidin-1-yl, piperidin-1-yl or piperazin-1-yl;
b) 1,2,3,4-tetrahydroisoquinolin-2-yl substituted with R$^b$ at 6-position with haloalkoxy, cyano, cycloalkyl, halo, alkoxy, haloalkyl, or alkoxyalkoxy; or
c) 3,6-dihydro-1(2H)-pyridinyl;
wherein each aforementioned ring B is substituted with R$^a$, R$^b$ or R$^c$;
wherein R$^a$ is hydrogen, alkyl, halo, haloalkyl, haloalkoxy, alkylthio, haloalkylthio, cyano, hydroxy, alkoxy, amino, monosubstituted amino, disubstituted amino, sulfonyl, thio, acyl, carboxy, alkoxycarbonyl, hydroxyalkyl, alkoxyalkyl, aminoalkyl, hydroxyalkoxy, hydroxyalkoxyalkyl, alkoxyalkoxy, aminoalkoxy, aminosulfonyl, aminocarbonyl, or acylamino and $R^b$ and $R^c$ are independently selected from hydrogen, alkyl, substituted alkyl, substituted alkynyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, sulfonylamino, aryl, heteroaryl, cycloalkyl, cycloalkenyl, heterocyclyl, aralkyl, heteroaralkyl, heterocyclylalkyl, aryloxy, heteroaryloxy, cycloalkoxy, aryloxyalkyl, aralkyloxy, aralkyloxyalkyl, aralkylthio, heteroaralkyloxy, heterocyclylalkyloxy, cycloalkylalkyloxy or cycloalkylalkyloxyalkyl;

where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, cyanoalkyl, alkylthio, cyano, hydroxy, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, cycloalkyl, cycloalkenyl, phenyl, phenoxy, heteroaryl, heterocyclyl, heterocyclylalkyl, aralkyl, aralkyloxy or heteroaralkyl and where the aromatic or alicyclic ring in $R^d$, $R^e$ or $R^f$ is optionally substituted with one to three substituents independently selected from alkyl, halo, haloalkyl, haloalkyloxy, hydroxyl, alkoxy, acetylamino, alkylsulfonyl, or cyano; or a pharmaceutically acceptable salt thereof;

provided that the compound is not 3-((4-((3S)-3-benzyl-1-piperidinyl)-1,3,5-triazin-2-yl)amino)-N-methylbenzamide; 3-((4-((3R)-3-benzyl-1-piperidinyl)-1,3,5-triazin-2-yl)amino)-N-methylbenzamide; or N-methyl-3-((4-(4-(4-morpholinylcarbonyl)-1-piperidinyl)-1,3,5-triazin-2-yl)amino)benzamide.

2. The compound of claim 1 where $R^1$ is alkyl.

3. The compound of claim 1 where A is phenyl, $R^4$ is hydrogen or halo, and $R^2$ is hydrogen, alkyl, hydroxy, alkoxy, halo, haloalkyl, or dialkylamino.

4. The compound of claim 1 where —$NR^5R^6$ is wherein ring B is azetidinyl or piperidin-1-yl or wherein azetidin-1-yl is substituted at the 3-position of the ring and piperidin-1-yl is substituted at the 4-position of piperidin-1-yl ring, with $R^b$ where $R^b$ is aryloxy, aralkyloxy or aryloxyalkyl optionally substituted with $R^d$, $R^e$, or $R^f$.

5. The compound in accordance with claim 1, wherein the compound is selected from:
   3-((4-(3-(4-chlorophenoxy)-1-azetidinyl)-1,3,5-triazin-2-yl)amino)-N-methylbenzamide;
   2-fluoro-N-methyl-5-((4-(4-(4-phenyl-1,3-thiazol-2-yl)-1-piperidinyl)-1,3,5-triazin-2-yl)amino)benzamide;
   5-((4-(3-(4-chlorophenoxy)-1-azetidinyl)-1,3,5-triazin-2-yl)amino)-2-fluoro-N-methylbenzamide;
   N-methyl-3-((4-(3-((4-(trifluoromethyl)phenoxy)methyl)-1-azetidinyl)-1,3,5-triazin-2-yl)amino)benzamide;
   2-fluoro-N-methyl-5-((4-(3-(4-(trifluoromethyl)phenoxy)-1-azetidinyl)-1,3,5-triazin-2-yl)amino)benzamide;
   3-((4-(3-(4-chloro-3-methylphenoxy)-1-azetidinyl)-1,3,5-triazin-2-yl)amino)-N-methylbenzamide;
   2-chloro-N-methyl-5-((4-(6-(2,2,2-trifluoroethoxy)-3,4-dihydro-2(1H)-isoquinolinyl)-1,3,5-triazin-2-yl)amino)benzamide;
   3-((4-(3-(4-chloro-3-fluorophenoxy)-1-azetidinyl)-1,3,5-triazin-2-yl)amino)-N-methylbenzamide;
   5-((4-(3-(4-chloro-2-fluorophenoxy)-1-azetidinyl)-1,3,5-triazin-2-yl)amino)-2-fluoro-N-methylbenzamide;
   3-((4-(3-(3-chloro-4-fluorophenoxy)-1-azetidinyl)-1,3,5-triazin-2-yl)amino)-N-methylbenzamide;
   3-((4-(3-(4-fluoro-2-methylphenoxy)-1-azetidinyl)-1,3,5-triazin-2-yl)amino)-N-methylbenzamide;
   3-((4-(3-(3-ethylphenoxy)-1-azetidinyl)-1,3,5-triazin-2-yl)amino)-N-methylbenzamide;
   3-((4-(3-(2,5-dichlorophenoxy)-1-azetidinyl)-1,3,5-triazin-2-yl)amino)-N-methylbenzamide;
   3-((4-(3-(4-chloro-2-methylphenoxy)-1-azetidinyl)-1,3,5-triazin-2-yl)amino)-N-methylbenzamide;
   3-((4-(3-(4-chloro-2-fluorophenoxy)-1-azetidinyl)-1,3,5-triazin-2-yl)amino)-N-methylbenzamide;
   3-((4-(3-(2,3-dihydro-1H-inden-5-yloxy)-1-azetidinyl)-1,3,5-triazin-2-yl)amino)-N-methylbenzamide;
   N-methyl-3-((4-(4-(3-(trifluoromethoxy)phenyl)-1-piperazinyl)-1,3,5-triazin-2-yl)amino)benzamide;
   N-methyl-3-((4-(4-(4-phenyl-1,3-thiazol-2-yl)-1-piperidinyl)-1,3,5-triazin-2-yl)amino)benzamide;
   3-((4-(3-(3-chlorophenoxy)-1-azetidinyl)-1,3,5-triazin-2-yl)amino)-N-methylbenzamide;
   N-methyl-3-((4-(4-(4-(2-phenyl-1,3-thiazol-4-yl)-1-piperidinyl)-1,3,5-triazin-2-yl)amino)benzamide;
   2-chloro-N-methyl-5-((4-(4-(4-phenyl-1,3-thiazol-2-yl)-1-piperidinyl)-1,3,5-triazin-2-yl)amino)benzamide;
   3-((4-(3-(4-chlorophenoxy)-1-azetidinyl)-1,3,5-triazin-2-yl)amino)-N-(2-methoxyethyl)benzamide;
   3-((4-(3-(2-chlorophenoxy)-1-azetidinyl)-1,3,5-triazin-2-yl)amino)-N-methylbenzamide;
   3-((4-(3-(2-chloro-4-methylphenoxy)-1-azetidinyl)-1,3,5-triazin-2-yl)amino)-N-methylbenzamide;
   N-methyl-3-((4-(3-phenoxy-1-azetidinyl)-1,3,5-triazin-2-yl)amino)benzamide;
   N-methyl-3-((4-(4-(4-methylphenyl)-1-piperazinyl)-1,3,5-triazin-2-yl)amino)benzamide;
   N-methyl-3-((4-(3-(4-(trifluoromethyl)phenoxy)-1-azetidinyl)-1,3,5-triazin-2-yl)amino)benzamide;
   3-((4-(4-(4-chlorophenyl)carbonyl)-1-piperidinyl)-1,3,5-triazin-2-yl)amino)-N-methylbenzamide;
   3-((4-(3-(4-chlorophenoxy)-1-azetidinyl)-1,3,5-triazin-2-yl)amino)-5-fluoro-N-methylbenzamide;
   3-((4-(3-(4-fluorophenoxy)-1-azetidinyl)-1,3,5-triazin-2-yl)amino)-N-(2-methoxyethyl)benzamide;
   3-((4-(3-(3,4-dichlorophenoxy)-1-azetidinyl)-1,3,5-triazin-2-yl)amino)-N-methylbenzamide;
   3-((4-(3-((4-chlorophenoxy)methyl)-1-azetidinyl)-1,3,5-triazin-2-yl)amino)-N-methylbenzamide;
   N-methyl-3-((4-(6-(2,2,2-trifluoroethoxy)-3,4-dihydro-2(1H)-isoquinolinyl)-1,3,5-triazin-2-yl)amino)benzamide;
   N-methyl-3-((4-(3-(4-(1-methylethyl)phenoxy)-1-azetidinyl)-1,3,5-triazin-2-yl)amino)benzamide;

N-methyl-3-((4-(4-(3-(trifluoromethyl)phenyl)-1-piperazinyl)-1,3,5-triazin-2-yl)amino)benzamide;
3-((4-(4-(3-methoxyphenyl)-1-piperazinyl)-1,3,5-triazin-2-yl)amino)-N-methylbenzamide;
N-methyl-3-((4-(4-phenoxy-1-piperidinyl)-1,3,5-triazin-2-yl)amino)benzamide;
N-methyl-3-((4-(4-(2-phenyl-1,3-thiazol-4-yl)-3,6-dihydro-1(2H)-pyridinyl)-1,3,5-triazin-2-yl)amino)benzamide;
3-((4-(3-((4-chlorophenoxy)methyl)-1-azetidinyl)-1,3,5-triazin-2-yl)amino)-N-(2-methoxyethyl)benzamide;
3-((4-(4-(3-fluorophenoxy)-1-piperidinyl)-1,3,5-triazin-2-yl)amino)-N-methylbenzamide;
N-methyl-3-((4-(3-(3-methylphenoxy)-1-azetidinyl)-1,3,5-triazin-2-yl)amino)benzamide;
5-((4-(3-(4-chlorophenoxy)-1-azetidinyl)-1,3,5-triazin-2-yl)amino)-2-(dimethylamino)-N-methylbenzamide;
3-((4-(3-(2,4-dichlorophenoxy)-1-azetidinyl)-1,3,5-triazin-2-yl)amino)-N-methylbenzamide;
N-methyl-3-((4-(4-(4-phenyl-1,3-thiazol-2-yl)-3,6-dihydro-1(2H)-pyridinyl)-1,3,5-triazin-2-yl)amino)benzamide;
3-((4-(4-(3,4-dimethylphenyl)-1-piperazinyl)-1,3,5-triazin-2-yl)amino)-N-methylbenzamide;
3-((4-(3-(2-chloro-4-fluorophenoxy)-1-azetidinyl)-1,3,5-triazin-2-yl)amino)-N-methylbenzamide;
3-((6-(3-(4-fluorophenoxy)-1-azetidinyl)-2-pyridinyl)amino)-N-methylbenzamide;
2-fluoro-5-((4-(3-(4-fluorophenoxy)-1-azetidinyl)-1,3,5-triazin-2-yl)amino)-N-methylbenzamide;
N-methyl-3-((4-(4-(4-(trifluoromethoxy)phenoxy)-1-piperidinyl)-1,3,5-triazin-2-yl)amino)benzamide;
3-((4-(4-(3-fluorophenyl)-1-piperazinyl)-1,3,5-triazin-2-yl)amino)-N-methylbenzamide;
3-((4-(3-(4-fluorophenoxy)-1-azetidinyl)-1,3,5-triazin-2-yl)amino)-N-methylbenzamide;
N-methyl-3-((4-(3-(3-(trifluoromethyl)phenoxy)-1-azetidinyl)-1,3,5-triazin-2-yl)amino)benzamide;
3-((4-(3-(2, 6-dichlorophenoxy)-1-azetidinyl)-1,3,5-triazin-2-yl)amino)-N-methylbenzamide;
N-methyl-3-((4-(4-phenyl-1-piperidinyl)-1,3,5-triazin-2-yl)amino)benzamide;
3-((4-(3-(2-chloro-5-methylphenoxy)-1-azetidinyl)-1,3,5-triazin-2-yl)amino)-N-methylbenzamide;
N-methyl-3-((4-(3-((4-(trifluoromethoxy)phenoxy)methyl)-1-azetidinyl)-1,3,5-triazin-2-yl)amino)benzamide;
3-((4-(4-(3-fluoro-4-(trifluoromethoxy)phenoxy)-1-piperidinyl)-1,3,5-triazin-2-yl)amino)-N-methylbenzamide;
3-((4-(4-(3-chlorophenyl)-1-piperazinyl)-1,3,5-triazin-2-yl)amino)-N-methylbenzamide;
5-((4-(3-((4-chlorophenoxy)methyl)-1-azetidinyl)-1,3,5-triazin-2-yl)amino)-2-fluoro-N-methylbenzamide;
3-((4-(5-cyano-3,4-dihydro-2(1H)-isoquinolinyl)-1,3,5-triazin-2-yl)amino)-N-methylbenzamide;
3-((4-(3-((4-chloro-2-methylphenoxy)methyl)-1-azetidinyl)-1,3,5-triazin-2-yl)amino)-N-methylbenzamide;
N-methyl-3-((4-(4-(4-(trifluoromethyl)phenyl)-1-piperazinyl)-1,3,5-triazin-2-yl)amino)benzamide;
N-methyl-3-((4-(4-(6-methyl-2-pyridinyl)-1-piperazinyl)-1,3,5-triazin-2-yl)amino)benzamide;
N-methyl-3-((4-(6-(3,3,3-trifluoropropoxy)-3,4-dihydro-2(1H)-isoquinolinyl)-1,3,5-triazin-2-yl)amino)benzamide;
3-((4-(3-(3-ethynylphenoxy)-1-azetidinyl)-1,3,5-triazin-2-yl)amino)-N-methylbenzamide;
2-chloro-5-((4-(3-(4-chloro-2-fluorophenoxy)-1-azetidinyl)-1,3,5-triazin-2-yl)amino)-N-methylbenzamide;
3-((4-(3-(3-methoxyphenoxy)-1-azetidinyl)-1,3,5-triazin-2-yl)amino)-N-methylbenzamide;
3-((4-(4-(2,3-dimethylphenyl)-1-piperazinyl)-1,3,5-triazin-2-yl)amino)-N-methylbenzamide;
N-methyl-3-((4-(4-(4-(trifluoromethoxy)phenyl)-1-piperazinyl)-1,3,5-triazin-2-yl)amino)benzamide;
N-methyl-3-((4-(3-(4-((trifluoromethyl)sulfanyl)phenoxy)-1-azetidinyl)-1,3,5-triazin-2-yl)amino)benzamide;
3-((4-(4-(4-chloro-3-fluorophenoxy)-1-piperidinyl)-1,3,5-triazin-2-yl)amino)-N-methylbenzamide;
3-((4-(4-(2-chlorophenoxy)-1-piperidinyl)-1,3,5-triazin-2-yl)amino)-N-methylbenzamide;
3-((4-(3-(3-fluorophenoxy)-1-azetidinyl)-1,3,5-triazin-2-yl)amino)-N-methylbenzamide;
3-((4-(3-(4-methoxyphenoxy)-1-azetidinyl)-1,3,5-triazin-2-yl)amino)-N-methylbenzamide;
N-methyl-3-((4-(4-(phenylcarbonyl)-1-piperidinyl)-1,3,5-triazin-2-yl)amino)benzamide;
N-methyl-3-((4-(4-(2-methylphenyl)-1-piperazinyl)-1,3,5-triazin-2-yl)amino)benzamide;
2-chloro-5-((4-(3-((4-chlorophenoxy)methyl)-1-azetidinyl)-1,3,5-triazin-2-yl)amino)-N-methylbenzamide;
3-((4-(3-((4-chloro-3-fluorophenoxy)methyl)-1-azetidinyl)-1,3,5-triazin-2-yl)amino)-N-methylbenzamide;
3-((4-(6-cyclopropyl-3,4-dihydro-2(1H)-isoquinolinyl)-1,3,5-triazin-2-yl)amino)-N-methylbenzamide;
3-((4-(4-((3,4-difluorophenoxy)methyl)-1-piperidinyl)-1,3,5-triazin-2-yl)amino)-N-methylbenzamide;
N-methyl-3-((4-(3-((4-(trifluoromethoxy)benzyl)oxy)-1-azetidinyl)-1,3,5-triazin-2-yl)amino)benzamide;
3-((4-(4-(2-fluorophenyl)-1-piperazinyl)-1,3,5-triazin-2-yl)amino)-N-methylbenzamide;
2-chloro-N-methyl-5-((4-(3-((4-(trifluoromethyl)phenoxy)methyl)-1-azetidinyl)-1,3,5-triazin-2-yl)amino)benzamide;
2-chloro-5-((4-(3-(3-chloro-4-fluorophenoxy)-1-azetidinyl)-1,3,5-triazin-2-yl)amino)-N-methylbenzamide;
3-fluoro-5-((4-(3-(4-fluorophenoxy)-1-azetidinyl)-1,3,5-triazin-2-yl)amino)-N-methylbenzamide;
3-((4-(4-(4-cyanophenyl)-3,6-dihydro-1(2H)-pyridinyl)-1,3,5-triazin-2-yl)amino)-N-methylbenzamide;
mixture of N-methyl-3-((4-(((1R)-1-methyl-3-phenylpropyl)amino)-1,3,5-triazin-2-yl)amino)benzamide; and N-methyl-3-((4-(((1 S)-1-methyl-3-phenylpropyl)amino)-1,3,5-triazin-2-yl)amino)benzamide;
N-methyl-3-((4-(4-(4-(2,2,2-trifluoroethoxy)phenoxy)-1-piperidinyl)-1,3,5-triazin-2-yl)amino)benzamide;
N-ethyl-3-((4-(3-(4-fluorophenoxy)-1-azetidinyl)-1,3,5-triazin-2-yl)amino)benzamide;
3-fluoro-N-methyl-5-((4-(4-(4-phenyl-1,3-thiazol-2-yl)-1-piperidinyl)-1,3,5-triazin-2-yl)amino)benzamide;
3-((4-(3-(2,3-dichlorophenoxy)-1-azetidinyl)-1,3,5-triazin-2-yl)amino)-N-methylbenzamide;
3-((4-(3-((4-chloro-2-fluorophenoxy)methyl)-1-azetidinyl)-1,3,5-triazin-2-yl)amino)-N-methylbenzamide;
3-((4-(4-(5-chloro-2-pyridinyl)-1-piperazinyl)-1,3,5-triazin-2-yl)amino)-N-methylbenzamide;
N-methyl-3-((4-(4-(2-phenylethyl)-1-piperazinyl)-1,3,5-triazin-2-yl)amino)benzamide;
N-methyl-3-((4-(6-(trifluoromethoxy)-3,4-dihydro-2(1H)-isoquinolinyl)-1,3,5-triazin-2-yl)amino)benzamide;
N-methyl-3-((4-(3-(3-(trifluoromethoxy)phenoxy)-1-azetidinyl)-1,3,5-triazin-2-yl)amino)benzamide;

3-fluoro-N-methyl-5-((4-(3-((4-(trifluoromethyl)phenoxy)methyl)-1-azetidinyl)-1,3,5-triazin-2-yl)amino)benzamide;
3-((4-(3-(4-chlorobenzyl)oxy)-1-azetidinyl)-1,3,5-triazin-2-yl)amino)-N-methylbenzamide;
N-methyl-3-((4-(4-(3-methylphenyl)-1-piperazinyl)-1,3,5-triazin-2-yl)amino)benzamide;
N-methyl-3-((4-(4-phenyl-1-piperazinyl)-1,3,5-triazin-2-yl)amino)benzamide;
3-fluoro-N-methyl-5-((4-(4-(6-methyl-2-pyridinyl)-1-piperazinyl)-1,3,5-triazin-2-yl)amino)benzamide;
3-((4-(4-(3,4-dimethylphenyl)-1-piperidinyl)-1,3,5-triazin-2-yl)amino)-N-methylbenzamide;
N-methyl-3-((4-(4-(4-(trifluoromethyl)phenoxy)-1-piperidinyl)-1,3,5-triazin-2-yl)amino)benzamide;
N-methyl-3-((4-(4-(3-(trifluoromethoxy)phenoxy)-1-piperidinyl)-1,3,5-triazin-2-yl)amino)benzamide;
3-((4-(3-(3-chloro-4-fluorophenoxy)-1-azetidinyl)-1,3,5-triazin-2-yl)amino)-5-fluoro-N-methylbenzamide;
3-((4-(4-(3-chlorophenoxy)-1-piperidinyl)-1,3,5-triazin-2-yl)amino)-N-methylbenzamide;
N-methyl-3-((4-(5-(trifluoromethoxy)-3,4-dihydro-2(1H)-isoquinolinyl)-1,3,5-triazin-2-yl)amino)benzamide;
N-methyl-3-((4-(4-(phenylethynyl)-1-piperidinyl)-1,3,5-triazin-2-yl)amino)benzamide;
N-methyl-3-((4-(4-(4-(trifluoromethoxy)phenyl) sulfonyl)-1-piperazinyl)-1,3,5-triazin-2-yl)amino)benzamide;
3-((4-(3-(3-chloro-4-cyanophenoxy)-1-azetidinyl)-1,3,5-triazin-2-yl)amino)-N-methylbenzamide;
4-chloro-3-((4-(3-(4-fluorophenoxy)-1-azetidinyl)-1,3,5-triazin-2-yl)amino)-N-methylbenzamide;
3-((4-(6-chloro-3,4-dihydro-2(1H)-isoquinolinyl)-1,3,5-triazin-2-yl)amino)-N-methylbenzamide;
N-methyl-3-((4-(4-(4-(trifluoromethoxy)benzyl)oxy)-1-piperidinyl)-1,3,5-triazin-2-yl)amino)benzamide;
3-((4-(3-((2,4-dichlorophenoxy)methyl)-1-azetidinyl)-1,3,5-triazin-2-yl)amino)-N-methylbenzamide;
3-((4-(4-(3,4-dimethylphenyl)-3,6-dihydro-1(2H)-pyridinyl)-1,3,5-triazin-2-yl)amino)-N-methylbenzamide;
3-((4-(3-(3-tert-butylphenoxy)-1-azetidinyl)-1,3,5-triazin-2-yl)amino)-N-methylbenzamide;
N-methyl-3-((4-(4-(4-(trifluoromethoxy)phenyl)-1-piperidinyl)-1,3,5-triazin-2-yl)amino)benzamide;
N-methyl-3-((4-(4-(4-(trifluoromethoxy)phenyl)-3,6-dihydro-1(2H)-pyridinyl)-1,3,5-triazin-2-yl)amino)benzamide;
N-methyl-3-((4-(5-(2,2,2-trifluoroethoxy)-3,4-dihydro-2(1H)-isoquinolinyl)-1,3,5-triazin-2-yl)amino)benzamide;
3-((4-(5-methoxy-3,4-dihydro-2(1H)-isoquinolinyl)-1,3,5-triazin-2-yl)amino)-N-methylbenzamide;
N-methyl-3-((4-(4-(4-phenyl-1H-pyrazol-1-yl)-1-piperidinyl)-1,3,5-triazin-2-yl)amino)benzamide;
N-methyl-3-((4-(4-(3-phenyl-1,2,4-oxadiazol-5-yl)-1-piperidinyl)-1,3,5-triazin-2-yl)amino)benzamide;
N-methyl-3-((4-(3-(2-(trifluoromethyl)phenoxy)-1-azetidinyl)-1,3,5-triazin-2-yl)amino)benzamide;
3-((4-(5-chloro-3,4-dihydro-2(1H)-isoquinolinyl)-1,3,5-triazin-2-yl)amino)-N-methylbenzamide;
N-methyl-3-((4-(4-(phenoxymethyl)-1-piperidinyl)-1,3,5-triazin-2-yl)amino)benzamide;
3-((4-(4-(4-chlorophenoxy)-1-piperidinyl)-1,3,5-triazin-2-yl)amino)-N-methylbenzamide;
3-fluoro-N-methyl-5-((4-(4-(4-(trifluoromethoxy)phenoxy)-1-piperidinyl)-1,3,5-triazin-2-yl)amino)benzamide;
3-((4-(4-(4-chlorophenyl)-4-cyano-1-piperidinyl)-1,3,5-triazin-2-yl)amino)-N-methylbenzamide;
3-((4-(3-(2,4-difluorophenoxy)-1-azetidinyl)-1,3,5-triazin-2-yl)amino)-N-methylbenzamide;
3-((4-(3-(4-tert-butylphenoxy)-1-azetidinyl)-1,3,5-triazin-2-yl)amino)-N-methylbenzamide;
N-methyl-3-((4-(4-(4-(trifluoromethyl)benzyl)oxy)-1-piperidinyl)-1,3,5-triazin-2-yl)amino)benzamide;
3-((4-(4-(3,4-difluorobenzyl)-1-piperidinyl)-1,3,5-triazin-2-yl)amino)-N-methylbenzamide;
3-((4-(3-(4-chloro-2,6-difluorophenoxy)-1-azetidinyl)-1,3,5-triazin-2-yl)amino)-N-methylbenzamide;
mixture of N-methyl-3-((4-((3S)-3-(4-(trifluoromethoxy)phenoxy)-1-pyrrolidinyl)-1,3,5-triazin-2-yl)amino)benzamide; and N-methyl-3-((4-((3R)-3-(4-(trifluoromethoxy)phenoxy)-1-pyrrolidinyl)-1,3,5-triazin-2-yl)amino)benzamide;
3-((4-(3-(2-fluoro-5-methylphenoxy)-1-azetidinyl)-1,3,5-triazin-2-yl)amino)-N-methylbenzamide;
3-((4-(4-(4-chlorophenyl)-1-piperazinyl)-1,3,5-triazin-2-yl)amino)-N-methylbenzamide;
3-((4-(3-((3,4-dichlorophenoxy)methyl)-1-azetidinyl)-1,3,5-triazin-2-yl)amino)-N-methylbenzamide;
3-((4-(4-(4-methoxyphenyl)-1-piperazinyl)-1,3,5-triazin-2-yl)amino)-N-methylbenzamide;
3-((4-(3-(4-fluorophenoxy)-1-azetidinyl)-1,3,5-triazin-2-yl)amino)-N,4-dimethylbenzamide;
3-((4-(3-((4-chlorophenoxy)methyl)-1-azetidinyl)-1,3,5-triazin-2-yl)amino)-2,6-difluoro-N-methylbenzamide;
2-chloro-5-((4-(3-(4-chlorophenoxy)-1-azetidinyl)-1,3,5-triazin-2-yl)amino)-N-methylbenzamide;
3-((4-(3-(4-fluorophenoxy)methyl)-1-azetidinyl)-1,3,5-triazin-2-yl)amino)-N-methylbenzamide;
4-fluoro-3-((4-(3-(4-fluorophenoxy)-1-azetidinyl)-1,3,5-triazin-2-yl)amino)-N-methylbenzamide;
3-((4-(4-(4-chloro-3-(trifluoromethoxy)phenoxy)-1-piperidinyl)-1,3,5-triazin-2-yl)amino)-N-methylbenzamide;
3-((4-(4-(4-chlorophenyl)-1H-pyrazol-1-yl)-1-piperidinyl)-1,3,5-triazin-2-yl)amino)-N-methylbenzamide;
N-methyl-3-((4-(4-(5-methyl-4-phenyl-1,3-thiazol-2-yl)-1-piperidinyl)-1,3,5-triazin-2-yl)amino)benzamide;
3-((4-(4-(4-cyanophenyl)-1-piperidinyl)-1,3,5-triazin-2-yl)amino)-N-methylbenzamide;
N-methyl-3-((4-(3-((3-(trifluoromethoxy)phenoxy)methyl)-1-azetidinyl)-1,3,5-triazin-2-yl)amino)benzamide;
N-methyl-3-((4-(4-(2-(trifluoromethoxy)phenyl)-1-piperazinyl)-1,3,5-triazin-2-yl)amino)benzamide;
3-((4-(3-((4-chlorophenoxy)methyl)-1-azetidinyl)-1,3,5-triazin-2-yl)amino)-5-fluoro-N-methylbenzamide;
3-((4-(3-(4-fluorophenoxy)-1-azetidinyl)-1,3,5-triazin-2-yl)amino)-N-(2,2,2-trifluoroethyl)benzamide;
N-methyl-3-((4-(4-(2-pyridinyloxy)-1-piperidinyl)-1,3,5-triazin-2-yl)amino)benzamide;
3-((4-(6-fluoro-3,4-dihydro-2(1H)-isoquinolinyl)-1,3,5-triazin-2-yl)amino)-N-methylbenzamide;
3-((4-(3-(2,5-difluorophenoxy)-1-azetidinyl)-1,3,5-triazin-2-yl)amino)-N-methylbenzamide;
N-methyl-3-((4-(4-(2-(trifluoromethyl)phenyl)-1-piperazinyl)-1,3,5-triazin-2-yl)amino)benzamide;
3-((4-(3-(4-fluorophenoxy)-1-azetidinyl)-2-pyridinyl)amino)-N-methylbenzamide;

N-methyl-3-((4-(4-(4-(trifluoromethoxy)benzyl)-1-piperazinyl)-1,3,5-triazin-2-yl)amino)benzamide;
N-methyl-3-((4-(3-(2-(trifluoromethoxy)phenoxy)-1-azetidinyl)-1,3,5-triazin-2-yl)amino)benzamide;
N-methyl-3-((4-(3-methyl-3-(4-methylphenoxy)-1-azetidinyl)-1,3,5-triazin-2-yl)amino)benzamide;
3-((4-(3-(4-chlorophenoxy)-1-azetidinyl)-1,3,5-triazin-2-yl)amino)-2,6-difluoro-N-methylbenzamide;
3-((4-(3-(4-chlorophenyl)-1-azetidinyl)-1,3,5-triazin-2-yl)amino)-N-methylbenzamide;
N-methyl-3-((4-(6-methyl-3,4-dihydro-2(1H)-isoquinolinyl)-1,3,5-triazin-2-yl)amino)benzamide;
mixture of 3-((4-(3-((1R)-1-(4-chlorophenoxy)ethyl)-1-azetidinyl)-1,3,5-triazin-2-yl)amino)-N-methylbenzamide; and 3-((4-(3-((1S)-1-(4-chlorophenoxy)ethyl)-1-azetidinyl)-1,3,5-triazin-2-yl)amino)-N-methylbenzamide;
3-((4-(3-(3,5-difluorophenoxy)-1-azetidinyl)-1,3,5-triazin-2-yl)amino)-N-methylbenzamide;
N-methyl-3-((4-(3-((3-(trifluoromethyl)phenoxy)methyl)-1-azetidinyl)-1,3,5-triazin-2-yl)amino)benzamide;
N-methyl-3-((4-(3-(((4-(trifluoromethyl)benzyl)oxy)methyl)-1-azetidinyl)-1,3,5-triazin-2-yl)amino)benzamide;
3-((4-(4-(4-(2-chlorophenyl)-1H-pyrazol-1-yl)-1-piperidinyl)-1,3,5-triazin-2-yl)amino)-N-methylbenzamide;
N-methyl-3-((4-(4-(2-(trifluoromethoxy)benzyl)-1-piperazinyl)-1,3,5-triazin-2-yl)amino)benzamide;
3-((4-(3-(2-fluorophenoxy)-1-azetidinyl)-1,3,5-triazin-2-yl)amino)-N-methylbenzamide;
3-((4-(4-(4-fluoro-3-(trifluoromethoxy)phenoxy)-1-piperidinyl)-1,3,5-triazin-2-yl)amino)-N-methylbenzamide;
3-((4-(3-(2-chloro-4-(trifluoromethyl)phenoxy)-1-azetidinyl)-1,3,5-triazin-2-yl)amino)-N-methylbenzamide;
3-((4-(4-(4-cyanophenyl)-1-piperazinyl)-1,3,5-triazin-2-yl)amino)-N-methylbenzamide;
3-((4-(4-(4-fluorobenzyl)-1-piperidinyl)-1,3,5-triazin-2-yl)amino)-N-methylbenzamide;
3-((4-(4-(4-fluorophenyl)-1-piperazinyl)-1,3,5-triazin-2-yl)amino)-N-methylbenzamide;
3-((4-(3-(3-biphenylyloxy)-1-azetidinyl)-1,3,5-triazin-2-yl)amino)-N-methylbenzamide;
3-((4-(4-((4-(trifluoromethoxy)benzyl)oxy)-1-piperidinyl)-1,3,5-triazin-2-yl)amino)benzamide;
3-((4-(3-((3-chlorophenoxy)methyl)-1-azetidinyl)-1,3,5-triazin-2-yl)amino)-N-methylbenzamide;
N,2-dimethyl-3-((4-(4-(4-(trifluoromethoxy)phenyl)-1-piperazinyl)-1,3,5-triazin-2-yl)amino)benzamide;
3-((4-(3-(2-methoxyphenoxy)-1-azetidinyl)-1,3,5-triazin-2-yl)amino)-N-methylbenzamide;
N-cyclopropyl-3-((4-(3-(4-fluorophenoxy)-1-azetidinyl)-1,3,5-triazin-2-yl)amino)benzamide;
3-((4-(4-(benzyloxy)-1-piperidinyl)-1,3,5-triazin-2-yl)amino)-N-methylbenzamide;
3-((4-(3-(4-(cyanomethyl)phenoxy)-1-azetidinyl)-1,3,5-triazin-2-yl)amino)-N-methylbenzamide;
3-((4-(3-((4-chloro-3-(trifluoromethyl)phenoxy)methyl)-1-azetidinyl)-1,3,5-triazin-2-yl)amino)-N-methylbenzamide;
N-methyl-3-((4-(4-(2-(trifluoromethoxy)phenoxy)-1-piperidinyl)-1,3,5-triazin-2-yl)amino)benzamide;
3-((4-(3-(4-cyanophenoxy)-1-azetidinyl)-1,3,5-triazin-2-yl)amino)-N-methylbenzamide;
3-((4-(2-((4-chlorophenoxy)methyl)-1-azetidinyl)-1,3,5-triazin-2-yl)amino)-N-methylbenzamide;
3-((4-(3-(2-chlorophenoxy)-1-piperidinyl)-1,3,5-triazin-2-yl)amino)-N-methylbenzamide;
N-tert-butyl-3-((4-(4-(4-fluorophenoxy)-1-azetidinyl)-1,3,5-triazin-2-yl)amino)benzamide;
3-((4-(3-(4-(benzyloxy)phenoxy)-1-azetidinyl)-1,3,5-triazin-2-yl)amino)-N-methylbenzamide;
3-((4-(4-(4-cyano-3-(trifluoromethyl)phenyl)-1-piperidinyl)-1,3,5-triazin-2-yl)amino)-N-methylbenzamide;
N-methyl-3-((4-(6-(trifluoromethyl)-3,4-dihydro-2(1H)-isoquinolinyl)-1,3,5-triazin-2-yl)amino)benzamide;
3-((4-(3-(2-biphenylyloxy)-1-azetidinyl)-1,3,5-triazin-2-yl)amino)-N-methylbenzamide;
5-((4-(3-(4-chlorophenoxy)-1-azetidinyl)-1,3,5-triazin-2-yl)amino)-2-hydroxy-N-methylbenzamide;
3-((4-(7-methoxy-3,4-dihydro-2(1H)-isoquinolinyl)-1,3,5-triazin-2-yl)amino)-N-methylbenzamide;
3-((4-(6-bromo-3,4-dihydro-2(1H)-isoquinolinyl)-1,3,5-triazin-2-yl)amino)benzamide;
3-((4-(6-methoxy-3,4-dihydro-2(1H)-isoquinolinyl)-1,3,5-triazin-2-yl)amino)-N-methylbenzamide;
3-((4-(3-((4-methoxyphenoxy)methyl)-1-azetidinyl)-1,3,5-triazin-2-yl)amino)-N-methylbenzamide;
3-((4-(3-(3,5-dichlorophenoxy)-1-azetidinyl)-1,3,5-triazin-2-yl)amino)-N-methylbenzamide;
3-((4-(5-fluoro-3,4-dihydro-2(1H)-isoquinolinyl)-1,3,5-triazin-2-yl)amino)-N-methylbenzamide;
N-methyl-3-((4-(3-(2,3,4-trifluorophenoxy)-1-azetidinyl)-1,3,5-triazin-2-yl)amino)benzamide;
2-chloro-5-((4-(4-(3,4-dimethylphenyl)-1-piperazinyl)-1,3,5-triazin-2-yl)amino)benzamide;
3-((4-(4-((3,4-difluorobenzyl)oxy)-1-piperidinyl)-1,3,5-triazin-2-yl)amino)-N-methylbenzamide;
N-methyl-3-((4-(3-((2-(trifluoromethoxy)phenoxy)methyl)-1-azetidinyl)-1,3,5-triazin-2-yl)amino)benzamide;
3-((4-(4-benzyl-1-piperidinyl)-1,3,5-triazin-2-yl)amino)-N-methylbenzamide;
N-methyl-3-((4-(4-(3-(1-methylethyl)-1,2,4-oxadiazol-5-yl)-1-piperidinyl)-1,3,5-triazin-2-yl)amino)benzamide;
3-((4-(6-(2-methoxyethoxy)-3,4-dihydro-2(1H)-isoquinolinyl)-1,3,5-triazin-2-yl)amino)-N-methylbenzamide;
N-methyl-3-((4-(3-((2-naphthalenyloxy)methyl)-1-azetidinyl)-1,3,5-triazin-2-yl)amino)benzamide;
3-((4-(3,4-dihydro-2(1H)-isoquinolinyl)-1,3,5-triazin-2-yl)amino)benzamide;
3-((4-(3-(4-fluorophenoxy)-1-azetidinyl)-1,3,5-triazin-2-yl)amino)benzamide;
3-((4-(4-(2-fluorophenoxy)-1-piperidinyl)-1,3,5-triazin-2-yl)amino)-N-methylbenzamide;
N-methyl-3-((4-(4-((3-(trifluoromethyl)benzyl)oxy)-1-piperidinyl)-1,3,5-triazin-2-yl)amino)benzamide;
N,N-dimethyl-3-((4-(4-((4-(trifluoromethoxy)benzyl)oxy)-1-piperidinyl)-1,3,5-triazin-2-yl)amino)benzamide;
3-((4-(3-(((4-chlorobenzyl)oxy)methyl)-1-azetidinyl)-1,3,5-triazin-2-yl)amino)-N-methylbenzamide;
3-((4-(3-((3-fluorophenoxy)methyl)-1-azetidinyl)-1,3,5-triazin-2-yl)amino)-N-methylbenzamide;
3-((4-(3,4-dihydro-2(1H)-isoquinolinyl)-1,3,5-triazin-2-yl)amino)-N-methylbenzamide;
3-((4-(3-((3-methoxyphenoxy)methyl)-1-azetidinyl)-1,3,5-triazin-2-yl)amino)-N-methylbenzamide;
3-((4-(4-cyano-4-(4-fluorophenyl)-1-piperidinyl)-1,3,5-triazin-2-yl)amino)-N-methylbenzamide;

N-methyl-3-((4-(4-(3-propyl-1,2,4-oxadiazol-5-yl)-1-piperidinyl)-1,3,5-triazin-2-yl)amino)benzamide;
3-((4-(3-((2-chlorophenoxy)methyl)-1-azetidinyl)-1,3,5-triazin-2-yl)amino)-N-methylbenzamide;
3-((4-(4-(4-cyano-3-(trifluoromethoxy)phenyl)-1-piperidinyl)-1,3,5-triazin-2-yl)amino)-N-methylbenzamide;
3-((4-(4-(4-chlorophenyl)-1-piperidinyl)-1,3,5-triazin-2-yl)amino)-N-methylbenzamide;
N-methyl-3-((4-(4-(4-methylphenyl)sulfanyl)-1-piperidinyl)-1,3,5-triazin-2-yl)amino)benzamide;
3-((4-(3-((2-fluorophenoxy)methyl)-1-azetidinyl)-1,3,5-triazin-2-yl)amino)-N-methylbenzamide;
3-((4-(5-(2-methoxyethoxy)-3,4-dihydro-2(1H)-isoquinolinyl)-1,3,5-triazin-2-yl)amino)-N-methylbenzamide;
N-methyl-3-((4-(3-((1-naphthalenyloxy)methyl)-1-azetidinyl)-1,3,5-triazin-2-yl)amino)benzamide;
3-((4-(3-(((5-chloro-8-quinolinyl)oxy)methyl)-1-azetidinyl)-1,3,5-triazin-2-yl)amino)-N-methylbenzamide;
3-((4-(3-(2-fluoro-3-(trifluoromethyl)phenoxy)-1-azetidinyl)-1,3,5-triazin-2-yl)amino)-N-methylbenzamide;
N-methyl-3-((4-(4-(phenylamino)-1-piperidinyl)-1,3,5-triazin-2-yl)amino)benzamide;
3-((4-(3-((4-cyanophenoxy)methyl)-1-azetidinyl)-1,3,5-triazin-2-yl)amino)-N-methylbenzamide;
3-((4-(4-((cyclopropylmethoxy)methyl)-1-piperidinyl)-1,3,5-triazin-2-yl)amino)-N-methylbenzamide;
3-chloro-5-((4-(3-(4-fluorophenoxy)-1-azetidinyl)-1,3,5-triazin-2-yl)amino)-N-methylbenzamide;
N-methyl-3-((4-(3-methyl-3-phenoxy-1-azetidinyl)-1,3,5-triazin-2-yl)amino)benzamide;
3-((4-(3-(4-cyclopentylphenoxy)-1-azetidinyl)-1,3,5-triazin-2-yl)amino)-N-methylbenzamide;
5-((4-(3-(4-fluorophenoxy)-1-azetidinyl)-1,3,5-triazin-2-yl)amino)-N,2-dimethylbenzamide;
2-methyl-3-((4-(4-((4-(trifluoromethoxy)benzyl)oxy)-1-piperidinyl)-1,3,5-triazin-2-yl)amino)benzamide;
N-methyl-3-((4-(8-(trifluoromethyl)-3,4-dihydro-2(1H)-isoquinolinyl)-1,3,5-triazin-2-yl)amino)benzamide;
2-fluoro-3-((4-(3-(4-fluorophenoxy)-1-azetidinyl)-1,3,5-triazin-2-yl)amino)-N-methylbenzamide;
3-((4-(4-(3-chloro-4-fluorophenyl)-1-piperazinyl)-1,3,5-triazin-2-yl)amino)-N-methylbenzamide;
3-((4-(3-((4-fluorobenzyl)oxy)-1-azetidinyl)-1,3,5-triazin-2-yl)amino)-N-methylbenzamide;
N-methyl-3-((4-(3-methyl-3-(phenoxymethyl)-1-azetidinyl)-1,3,5-triazin-2-yl)amino)benzamide;
3-((4-(3-(2,6-difluorophenoxy)-1-azetidinyl)-1,3,5-triazin-2-yl)amino)-N-methylbenzamide;
N,2-dimethyl-3-((4-(6-(2,2,2-trifluoroethoxy)-3,4-dihydro-2(1H)-isoquinolinyl)-1,3,5-triazin-2-yl)amino)benzamide;
N-methyl-3-((4-(3-((2-(trifluoromethyl)phenoxy)methyl)-1-azetidinyl)-1,3,5-triazin-2-yl)amino)benzamide;
N-methyl-3-((4-(4-(((3-(trifluoromethoxy)benzyl)oxy)-1-piperidinyl)-1,3,5-triazin-2-yl)amino)benzamide;
3-((4-(3-(3-chlorophenoxy)-1-piperidinyl)-1,3,5-triazin-2-yl)amino)-N-methylbenzamide;
3-((4-(7-chloro-3,4-dihydro-2(1H)-isoquinolinyl)-1,3,5-triazin-2-yl)amino)-N-methylbenzamide;
3-((4-(8-methoxy-3,4-dihydro-2(1H)-isoquinolinyl)-1,3,5-triazin-2-yl)amino)-N-methylbenzamide;
3-((4-(3-(4-chlorophenoxy)-1-azetidinyl)-1,3,5-triazin-2-yl)amino)-4-methoxy-N-methylbenzamide;
3-((4-(3-(4-fluorophenoxy)-1-azetidinyl)-6-methyl-1,3,5-triazin-2-yl)amino)-N-methylbenzamide;
2-fluoro-5-((4-(3-(4-fluorophenoxy)-1-azetidinyl)-1,3,5-triazin-2-yl)amino)benzamide;
N-methyl-3-((4-(6-(2,2,2-trifluoro-1-hydroxyethyl)-3,4-dihydro-2(1H)-isoquinolinyl)-1,3,5-triazin-2-yl)amino)benzamide;
3-((4-(6-bromo-3,4-dihydro-2(1H)-isoquinolinyl)-1,3,5-triazin-2-yl)amino)-2-methylbenzamide;
N-methyl-3-((4-(4-(3-phenylpropyl)-1-piperidinyl)-1,3,5-triazin-2-yl)amino)benzamide;
5-((4-(4-(3,4-dimethylphenyl)-1-piperazinyl)-1,3,5-triazin-2-yl)amino)-2-fluorobenzamide;
N-methyl-3-((4-(4-(2-methylpropoxy)-1-piperidinyl)-1,3,5-triazin-2-yl)amino)benzamide;
3-((4-(3-(2-cyanophenoxy)-1-azetidinyl)-1,3,5-triazin-2-yl)amino)-N-methylbenzamide;
N-methyl-3-((4-(7-(trifluoromethyl)-3,4-dihydro-2(1H)-isoquinolinyl)-1,3,5-triazin-2-yl)amino)benzamide; or
3-((4-(6-cyano-3,4-dihydro-2(1H)-isoquinolinyl)-1,3,5-triazin-2-yl)amino)-N-methylbenzamide; or a pharmaceutically acceptable salt thereof.

6. A pharmaceutical composition comprising a compound of any one of claim 1 or 5 and a pharmaceutically acceptable excipient.

* * * * *